United States Patent
Shahparnia et al.

(10) Patent No.: US 11,918,381 B2
(45) Date of Patent: Mar. 5, 2024

(54) VITAL SIGNS MONITORING SYSTEM

(71) Applicant: Apple Inc., Cupertino, CA (US)

(72) Inventors: Shahrooz Shahparnia, Monte Sereno, CA (US); Erno H. Klaassen, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/855,440

(22) Filed: Jun. 30, 2022

(65) Prior Publication Data

US 2022/0330893 A1 Oct. 20, 2022

Related U.S. Application Data

(63) Continuation of application No. 16/551,602, filed on Aug. 26, 2019, now Pat. No. 11,375,957, which is a continuation of application No. 15/675,478, filed on Aug. 11, 2017, now Pat. No. 10,512,432.

(60) Provisional application No. 62/374,615, filed on Aug. 12, 2016.

(51) Int. Cl.
*A61B 5/01* (2006.01)
*A61B 5/00* (2006.01)
(Continued)

(52) U.S. Cl.
CPC ............... *A61B 5/6892* (2013.01); *A61B 5/01* (2013.01); *A61B 5/02055* (2013.01);
(Continued)

(58) Field of Classification Search
None
See application file for complete search history.

(56) References Cited

U.S. PATENT DOCUMENTS 3,816,774 A 6/1974 Ohnuki
4,056,742 A 11/1977 Tibbetts
(Continued)

FOREIGN PATENT DOCUMENTS

AU PN304895 5/1995
CN 1795815 7/2006
(Continued)

OTHER PUBLICATIONS

Bischoff, "Quantified Sleep: A New Gadget From China Wants to Get in Bed With You," located at https://www.techinasia.com/quantified-sleep-gadget-china-bed/, accessed on Nov. 27, 2014, pp. 1-6.

(Continued)

*Primary Examiner* — Ankit D Tejani
(74) *Attorney, Agent, or Firm* — Brownstein Hyatt Farber Schreck, LLP

(57) ABSTRACT

This relates to a monitoring system capable of measuring a plurality of vital signs. The monitoring system can include a plurality of sensors including, but not limited to, electrodes, piezoelectric sensors, temperature sensors, and accelerometers. The monitoring system can be capable of operating in one or more operation modes such as, for example: capacitance measurement mode, electrical measurement mode, piezoelectric measurement mode, temperature measurement mode, acceleration measurement mode, impedance measurement mode, and standby mode. Based on the measured values, the monitoring system can analyze the user's sleep, provide feedback and suggestions to the user, and/or can adjust or control the environmental conditions to improve the user's sleep. The monitoring system can further be capable of analyzing the sleep of the user(s) without directly contacting or attaching uncomfortable probes to the user(s) and without having to analyze the sleep in an unknown environment (e.g., a medical facility).

21 Claims, 30 Drawing Sheets

(51) Int. Cl.
*A61B 5/0205* (2006.01)
*A61B 5/024* (2006.01)
*A61B 5/053* (2021.01)
*A61B 5/113* (2006.01)
*A61B 5/282* (2021.01)
*A61B 5/327* (2021.01)
*A61B 5/08* (2006.01)
*A61B 5/103* (2006.01)
*A61B 5/11* (2006.01)

(52) U.S. Cl.
CPC .......... *A61B 5/02444* (2013.01); *A61B 5/053* (2013.01); *A61B 5/113* (2013.01); *A61B 5/282* (2021.01); *A61B 5/327* (2021.01); *A61B 5/4815* (2013.01); *A61B 5/7278* (2013.01); *A61B 5/02405* (2013.01); *A61B 5/02438* (2013.01); *A61B 5/0816* (2013.01); *A61B 5/1036* (2013.01); *A61B 5/1102* (2013.01); *A61B 5/1126* (2013.01); *A61B 5/6843* (2013.01); *A61B 2560/0242* (2013.01); *A61B 2560/0252* (2013.01); *A61B 2562/0214* (2013.01); *A61B 2562/0247* (2013.01); *A61B 2562/046* (2013.01)

(56) References Cited

U.S. PATENT DOCUMENTS

| | | | |
|---|---|---|---|
| 5,479,939 | A | 1/1996 | Ogino |
| 5,483,261 | A | 1/1996 | Yasutake |
| 5,488,204 | A | 1/1996 | Mead et al. |
| 5,571,973 | A | 11/1996 | Taylot |
| 5,825,352 | A | 10/1998 | Bisset et al. |
| 5,835,079 | A | 11/1998 | Shieh |
| 5,880,411 | A | 3/1999 | Gillespie et al. |
| 6,107,726 | A | 8/2000 | Near |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,425,861 | B1 | 7/2002 | Haberland et al. |
| 6,468,234 | B1 | 10/2002 | Van der Loos et al. |
| 6,646,556 | B1 * | 11/2003 | Smith ............... A61B 5/6892 340/666 |
| 6,690,387 | B2 | 2/2004 | Zimmerman et al. |
| 6,833,656 | B2 | 12/2004 | Hooley et al. |
| 7,015,894 | B2 | 3/2006 | Morohoshi |
| 7,164,941 | B2 | 1/2007 | Misczynski et al. |
| 7,166,952 | B2 | 1/2007 | Topliss et al. |
| 7,184,064 | B2 | 2/2007 | Zimmerman et al. |
| 7,351,206 | B2 | 4/2008 | Suzuki et al. |
| 7,396,331 | B2 | 7/2008 | Mack et al. |
| 7,427,270 | B2 | 9/2008 | Izumi et al. |
| 7,442,107 | B1 | 10/2008 | Ueda et al. |
| 7,486,004 | B2 | 2/2009 | Allan et al. |
| 7,652,581 | B2 | 1/2010 | Gentry et al. |
| 7,654,948 | B2 | 2/2010 | Kaplan et al. |
| 7,656,299 | B2 | 2/2010 | Gentry et al. |
| 7,663,607 | B2 | 2/2010 | Hotelling et al. |
| 7,717,848 | B2 | 5/2010 | Heruth et al. |
| 8,002,553 | B2 | 8/2011 | Hallestad et al. |
| 8,003,982 | B2 | 8/2011 | Wang et al. |
| 8,161,826 | B1 | 4/2012 | Taylor |
| 8,262,582 | B2 | 9/2012 | Kortelainen |
| 8,348,840 | B2 | 1/2013 | Heit et al. |
| 8,355,769 | B2 | 1/2013 | Westbrook et al. |
| 8,398,538 | B2 | 3/2013 | Dothie et al. |
| 8,406,438 | B2 | 3/2013 | Ihl et al. |
| 8,479,122 | B2 | 7/2013 | Hotelling et al. |
| 8,532,737 | B2 | 9/2013 | Cervantes |
| 8,585,607 | B2 | 11/2013 | Klap et al. |
| 8,608,655 | B2 | 12/2013 | Izumi |
| 8,611,828 | B2 | 12/2013 | Richter et al. |
| 8,627,716 | B2 | 1/2014 | Son |
| 8,698,511 | B2 | 4/2014 | Wendt et al. |
| 8,768,520 | B2 | 7/2014 | Oexman et al. |
| 8,870,764 | B2 | 10/2014 | Rubin |
| 9,119,566 | B2 | 9/2015 | Sakai et al. |
| 9,247,831 | B2 | 2/2016 | Miles et al. |
| 9,310,779 | B2 | 4/2016 | Huh et al. |
| 9,314,583 | B2 | 4/2016 | Gavish |
| 9,344,546 | B2 | 5/2016 | Choudhary et al. |
| 9,345,404 | B2 | 5/2016 | Proud |
| 9,478,728 | B2 | 10/2016 | Capobianco et al. |
| 9,498,137 | B2 | 11/2016 | Kovacs |
| 9,592,005 | B2 | 3/2017 | Oakhill |
| 9,596,998 | B2 | 3/2017 | Muehlsteff et al. |
| 9,649,043 | B2 | 5/2017 | Meftah et al. |
| 9,693,696 | B2 | 7/2017 | Kovacs et al. |
| 9,750,415 | B2 | 9/2017 | Breslow et al. |
| 9,788,791 | B2 | 10/2017 | Brauers et al. |
| 9,808,202 | B2 | 11/2017 | Wu et al. |
| 9,814,410 | B2 | 11/2017 | Kostic et al. |
| 9,883,809 | B2 | 2/2018 | Klap et al. |
| 9,981,420 | B2 | 5/2018 | Benaissa et al. |
| 10,004,454 | B2 | 6/2018 | Krans et al. |
| 10,136,853 | B2 | 11/2018 | Heinrich et al. |
| 10,149,549 | B2 | 12/2018 | Erko et al. |
| 10,278,638 | B2 | 5/2019 | Dusanter et al. |
| 10,300,230 | B2 | 5/2019 | Flower et al. |
| 10,368,799 | B2 | 8/2019 | Sannholm |
| 10,376,155 | B2 | 8/2019 | Yang et al. |
| 10,376,214 | B2 | 8/2019 | Hayes et al. |
| 10,463,300 | B2 | 11/2019 | Kahn et al. |
| 10,512,432 | B2 | 12/2019 | Shahparnia et al. |
| 10,610,153 | B2 | 4/2020 | Auphan et al. |
| 11,275,405 | B2 | 3/2022 | Hotelling |
| 11,311,197 | B2 | 4/2022 | Yang et al. |
| 11,349,063 | B2 | 5/2022 | Han et al. |
| 11,375,957 | B2 | 7/2022 | Shahparnia et al. |
| 2005/0257822 | A1 | 11/2005 | Smith et al. |
| 2007/0118054 | A1 | 5/2007 | Pinhas et al. |
| 2008/0208063 | A1 * | 8/2008 | Brauers ............... A61B 5/282 600/481 |
| 2009/0121826 | A1 | 5/2009 | Song et al. |
| 2010/0331632 | A1 | 12/2010 | Chou |
| 2011/0230790 | A1 | 9/2011 | Kozlov |
| 2012/0092171 | A1 | 4/2012 | Hwang et al. |
| 2012/0283979 | A1 | 11/2012 | Bruekers et al. |
| 2013/0030257 | A1 | 1/2013 | Nakata et al. |
| 2013/0066168 | A1 * | 3/2013 | Yang ............... A61B 5/0537 600/301 |
| 2013/0245502 | A1 * | 9/2013 | Lange ............... A61B 5/411 600/595 |
| 2013/0261404 | A1 | 10/2013 | Sato et al. |
| 2014/0039351 | A1 | 2/2014 | Mix et al. |
| 2014/0213878 | A1 | 7/2014 | Banet et al. |
| 2014/0275829 | A1 | 9/2014 | Berezhnyy et al. |
| 2014/0276245 | A1 | 9/2014 | Tsutsumi et al. |
| 2014/0288385 | A1 | 9/2014 | Amurthur et al. |
| 2015/0011899 | A1 | 1/2015 | Shigeto et al. |
| 2015/0323388 | A1 * | 11/2015 | Kostic ............... A61B 5/11 5/425 |
| 2016/0038035 | A1 * | 2/2016 | Tseng ............... A61B 5/6892 600/549 |
| 2016/0106339 | A1 | 4/2016 | Behzadi et al. |
| 2016/0136385 | A1 * | 5/2016 | Scorcioni ............... A61B 5/4812 600/26 |
| 2016/0157780 | A1 | 6/2016 | Rimminen et al. |
| 2018/0028111 | A1 | 2/2018 | Waris et al. |

FOREIGN PATENT DOCUMENTS

| | | |
|---|---|---|
| CN | 1809315 | 7/2006 |
| CN | 101095612 | 1/2008 |
| CN | 101188969 | 5/2008 |
| CN | 101212354 | 7/2008 |
| CN | 101896120 | 11/2010 |
| CN | 101977544 | 2/2011 |
| CN | 102274009 | 12/2011 |
| CN | 102283654 | 12/2011 |
| CN | 102300499 | 12/2011 |
| CN | 102579020 | 7/2012 |

(56) References Cited

FOREIGN PATENT DOCUMENTS

| | | |
|---|---|---|
| CN | 104138260 | 11/2014 |
| CN | 104239415 | 12/2014 |
| CN | 105705093 | 6/2016 |
| CN | 105723307 | 6/2016 |
| CN | 106037140 | 10/2016 |
| DE | 102010063385 | 6/2012 |
| EP | 2278507 | 1/2011 |
| EP | 2301429 | 3/2011 |
| EP | 2644087 | 10/2013 |
| EP | 2432391 | 2/2014 |
| EP | 2783725 | 10/2014 |
| EP | 1890594 | 11/2014 |
| EP | 2870914 | 5/2015 |
| EP | 2976993 | 1/2016 |
| JP | 63016237 | 1/1988 |
| JP | 2000163031 | 6/2000 |
| JP | 2002342033 | 11/2002 |
| JP | 2004113618 | 4/2004 |
| JP | 2008082952 | 4/2008 |
| JP | 2008183181 | 8/2008 |
| JP | 2009233027 | 10/2009 |
| JP | 2012170471 | 9/2012 |
| TW | 2004058803 | 4/2004 |
| WO | WO 05/043443 | 5/2005 |
| WO | WO 06/131855 | 12/2006 |
| WO | WO 11/020299 | 2/2011 |
| WO | WO 12/122002 | 9/2012 |
| WO | WO 13/179189 | 12/2013 |
| WO | WO 14/151577 | 9/2014 |
| WO | WO 15/008285 | 1/2015 |
| WO | WO 15/075692 | 5/2015 |
| WO | WO 16/087709 | 6/2016 |
| WO | WO 16/120518 | 8/2016 |
| WO | WO 16/124817 | 8/2016 |
| WO | WO 18/217585 | 11/2018 |

OTHER PUBLICATIONS

Dagdeviren et al., "Recent Progress in Flexible and Stretchable Piezoelectric Devices for Mechanical Energy Harvesting, Sensing and Actuation," *Extreme Mechanics Letters*, Dec. 1, 2016, vol. 9, pp. 269-281.

Feng et al., "Stretchable Ferroelectric Nanoribbons with Wavy Configurations on Elastomeric Substrates," *ACS NANO*, Mar. 23, 2011, vol. 5, No. 4, pp. 3326-3332, pp. 3329, col. 1, paragraph 2 to col. 2, paragraph 1, figure 3.

Kortelainen et al. (Jun. 20-22, 2007). "PCA Model for Recording Respiration and Posture with Multichannel BCG Sensor in Bed Mattress," presented at the 4th pHealth Conference, Porto Carras, Greece, pp. 1-5.

Kortelainen et al. (May 2010). "Sleep Staging Based on Signals Acquired Through Bed Sensor," *IEEE Transactions on Information Technology in Biomedicine*, vol. 14, No. 3, pp. 776-785.

Lee et al. (Apr. 1985). "A Multi-Touch Three Dimensional Touch-Sensitive Tablet," Proceedings of CHI: ACM Conference on Human Factors in Computing Systems, pp. 21-25.

Paalasmaa (2014). "Monitoring Sleep with Force Sensor Measurement," University of Helsinki, Department of Computer Science, Series of Publication A, Report A—Feb. 2014, 69 pages.

Paalasmaa et al. (Aug. 28, 2012) "Unobtrusive Online Monitoring of Sleep at Home," Conference Proceeding Article, 34th Annual International Conference of the IEEE EMBS, p. 3784-3788.

Rubine (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Song et al. (Oct. 15, 2014). "Health Sensing by Wearable Sensors and Mobile Phones: A Survey," Conference Proceedings Article of the 16th International Conference on e-Health Networking, Applications and Services (Healthcom), p. 453-459.

Tikotzky et al., "Sleep and physical growth in infants during the first 6 months," *J. Sleep Res.*, 2010, vol. 19, pp. 103-110.

Westerman (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

Zeng et al., "Effects of Obstructive Sleep Apnea-Hypopnea Syndrome (OSAHS) on Height and Weight of Children," *Journal of Clinical Otorhinolaryngology Head and Neck Surgery*, Apr. 2013, vol. 27, No. 4, pp. 210-211.

\* cited by examiner

VITAL SIGNS MONITORING SYSTEM

CROSS-REFERENCE TO RELATED APPLICATIONS

This application is a continuation of U.S. patent application Ser. No. 16/551,602, filed Aug. 26, 2019, which is a continuation of U.S. patent application Ser. No. 15/675,478, filed Aug. 11, 2017, now U.S. Pat. No. 10,512,432, which claims priority to U.S. Provisional Patent Application No. 62/374,615, filed Aug. 12, 2016, which are hereby incorporated by reference in their entirety.

FIELD

This relates generally to monitoring systems and methods for measuring vital signs of one or more users.

BACKGROUND

Traditionally, monitoring a person's sleep or vital signs has required expensive and bulky equipment. Some systems require that the monitoring be performed away from home in a medical facility and/or require the equipment to attach to or directly contact the person, which can lead to discomfort and can lead to inaccurate analysis due to disruption of the person's sleep. Furthermore, these systems are configured to determine the vital signs based on one type of measurement or mode of operation. Moreover, these systems are configured for monitoring only a single person; these systems lack the capability of not only monitoring multiple users, but also incorporating the analysis of a first user into the analysis of a second user, whose sleep may be affected by the first user.

SUMMARY

This relates to a monitoring system capable of measuring a plurality of vital signs for one or more users. The monitoring system can include a plurality of sensors including, but not limited to, electrodes, piezoelectric sensors, temperature sensors, and accelerometers. The monitoring system can be capable of operating in one or more operation modes such as, for example: capacitance measurement mode, electrical measurement mode, piezoelectric measurement mode, temperature measurement mode, acceleration measurement mode, impedance measurement mode, and standby mode. Based on the measured values, the monitoring system can perform functions such as analyze the user's sleep, provide feedback and suggestions to the user, and/or can adjust or control the environmental conditions to improve the user's sleep. The monitoring system can be further capable of dynamically partitioning the system into multiple sections to account for multiple users. Each section can be tailored to the corresponding user with independent control and independent measurements to provide separate sleep analysis unique to the user. The monitoring system can utilize the information from one user in its assessment of the sleep of another user. The monitoring system can be utilized at home or can be portable, giving the user flexibility with locations where the monitoring system can be used. The monitoring system can further be capable of analyzing the sleep of the user(s) without directly contacting or attaching uncomfortable probes to the user(s) and without having to analyze the sleep in an unknown environment (e.g., a medical facility).

BRIEF DESCRIPTION OF THE DRAWINGS

FIGS. 3D-1 and 3D-2 illustrate an exemplary process flow for dynamically switching one or more electrodes utilized for capacitance measurements according to examples of the disclosure.

FIGS. 4D-1 and 4D-2 illustrate an exemplary process flow for capacitive and electrical measurements according to examples of the disclosure.

FIGS. 5B-1 to 5B-3 illustrate an exemplary process flow for dynamically partitioning the mat into multiple sections according to examples of the disclosure.

FIGS. 6E-1 and 6E-2 illustrate an exemplary process flow for capacitive, electrical, and piezoelectric measurements according to examples of the disclosure.

DETAILED DESCRIPTION

In the following description of examples, reference is made to the accompanying drawings in which it is shown by way of illustration specific examples that can be practiced. It is to be understood that other examples can be used and structural changes can be made without departing from the scope of the various examples.

Figure 1:
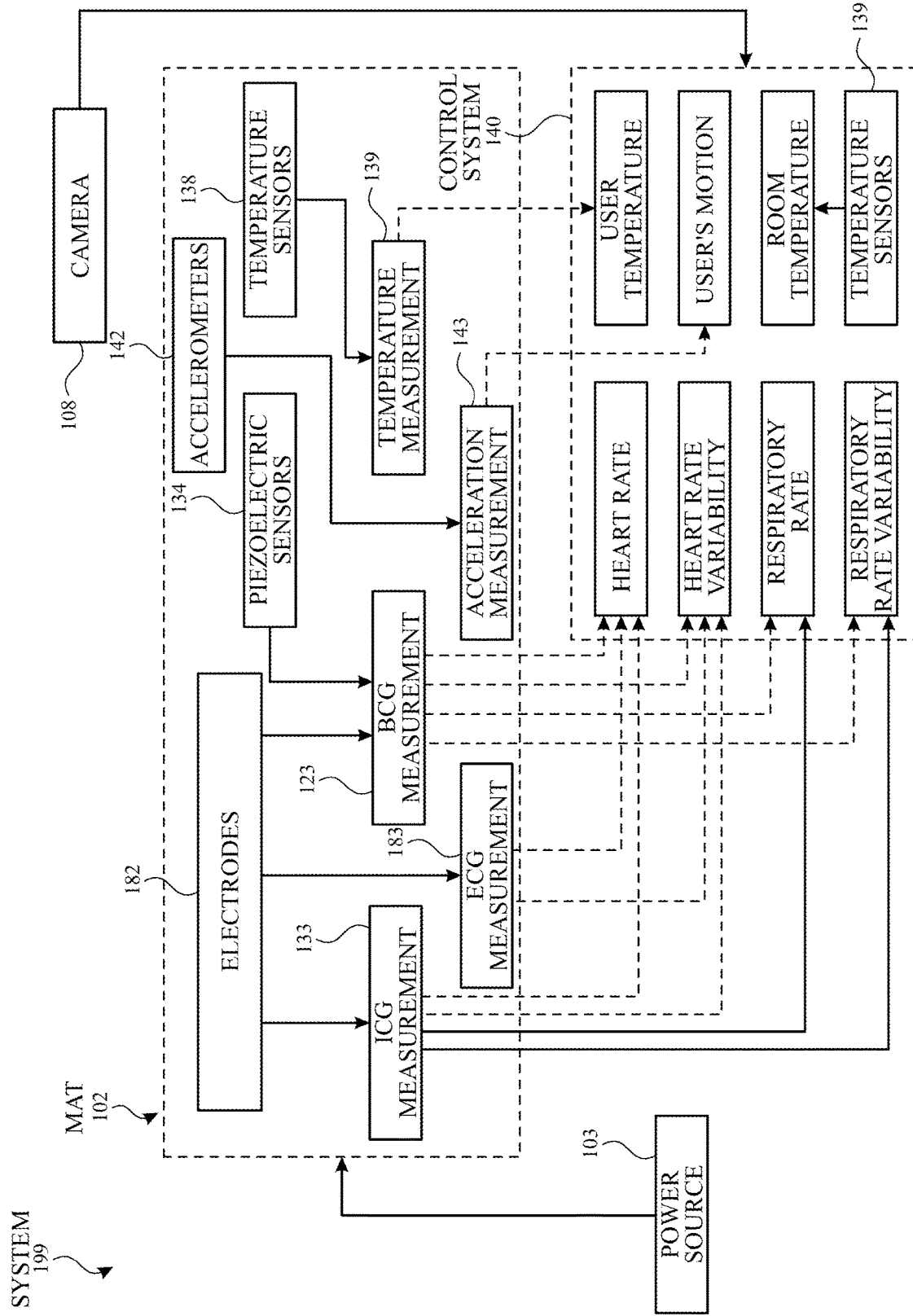
FIG. 1 illustrates an exemplary block diagram of the monitoring system according to examples of the disclosure.

FIG. 1 illustrates an exemplary block diagram of the monitoring system according to examples of the disclosure. System 199 can include mat 102, power source 103, camera 108, and control system 140. Mat 102 can be resting on, attached to, or in contact with a bed (not shown) or any type of apparatus configured to support one or more human users, one or more pets, or the like. Mat 102 can be configured to cover all or a portion of a mattress, for example, that can be resting, attached to, or supported by one or more frames of the bed. In some examples, mat 102 can be flexible. In some examples, mat 102 can be at least partially rigid. Mat 102 can include one or more of a sheet, blanket, duvet, pillow or pillowcase, or insert. Mat 102 can be a stand-alone unit that can be placed on a bed or can be incorporated into the fabric or textile used as part of a sleeping/resting arrangement.

Power source 103 can be configured to provide power to system 199. In some examples, the power source can be configured to couple to a power outlet. In some examples, the power source can be coupled to a battery and a charging station or power supply. In some examples, the power source can be configured to receive power from a charging element, such as a magnetic puck. In some examples, the charging element can include an inductive coil, and power can be transferred to the monitoring system via an electromagnetic field.

System 199 can include camera 108 and control system 140. Camera 108 can be a video camera configured to perform one or more functionalities, including, but not limited to, determining the position of the user's body, determining the location of the user's body, determining the temperature of the user's body, and determining the temperature of the local ambient. The monitoring system can be configured to utilize the information from camera 108 in conjunction with the information from the one or more sensors (e.g., electrodes 182, piezoelectric sensors 134, temperature sensors 138, accelerometers 142, and electrical sensors 182) for sleep analysis and feedback.

Control system 140 can be configured to control one or more parameters. For example, control system 140 can include temperature sensors 139, which can measure and provide information to the control system about the room temperature. In some examples, control system 140 can be configured to communicate with mat 102 through wired (e.g., using a cable) or wireless communications. Control panel 140 can include a touch panel and/or a display and can be configured to interface with the user and/or a computer. For example, control panel 140 can display heart rate, heart rate variability, respiratory rate, respiratory rate variability, user's motion, and user's temperature. In some examples, control panel 140 can display analysis regarding the user's sleep and/or can provide suggestions to improve the user's sleep.

Mat 102 can include one or more electrodes 182, one or more piezoelectric sensors 134, plurality of temperature sensors 138, and one or more accelerometers 142. The electrodes and sensors included in system 199 can include one or more functionalities and configurations discussed below. System 199 can include a controller configured to determine one or more measurements, such as BCG measurement 123, ECG measurement 183, acceleration measurement 143, temperature measurement 139, and ICG measurement 133. Although FIG. 1 illustrates mat 102 as including four different types of sensors, examples of the disclosure can include a monitoring system that includes one or more of the different types of sensors.

While control system 140 can be included in system 199, examples of the disclosure can include an arrangement where control system 140 is separate and distinct from system 199. System 199 can be communicate information (e.g., temperature measurement, acceleration measurement, ICG measurement, ECG measurement, and BCG measurement) to control system 140 through wired or wireless (e.g., local area network) communication means. In some examples, control system 140 can include a transceiver to receive the information from system 199 and a controller or processor to process the information for the analysis (e.g., to determine heart rate, heart rate variability, respiratory rate, and respiratory rate variability).

Figure 2A:
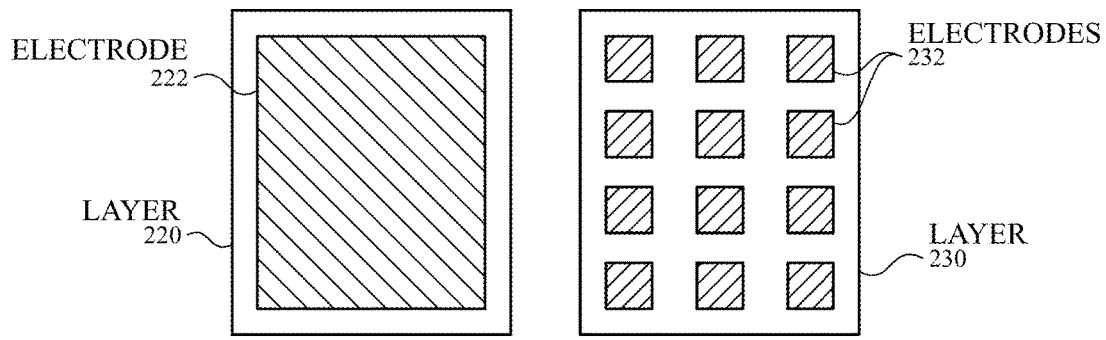
FIGS. 2A-2B illustrate top and perspective views of layers included in an exemplary mat according to examples of the disclosure.
Figure 2B:
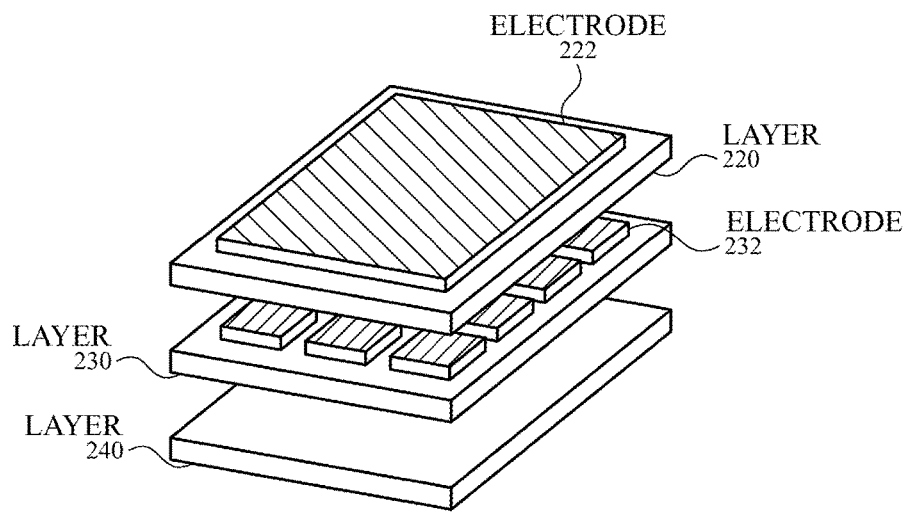

FIGS. 2A-2B illustrate top and perspective views of layers included in an exemplary mat according to examples of the disclosure. The exemplary mat can include layer 220 and layer 230. Layer 220 can include electrode 222. "Electrodes," referred to herein, can be a conductive unit individually connected for driving or sensing purposes. In some examples, electrode 222 can be configured to cover a substantial (e.g., more than 75%) area of layer 222 and can be continuous (i.e., a discrete piece of material). Layer 230 can include a plurality of electrodes 232. Electrode 222, plurality of electrodes 232, or both can include any conductive material including, but not limited to, silver, copper, gold, aluminum, steel, brass, bronze, and graphite. In some examples, electrode 222 and plurality of electrodes 232 can include the same materials. In some examples, the exemplary mat can include layer 240. Layer 240 can be configured to provide support or electrical insulation from one or more materials or layers (e.g., the mattress), for example. In some examples, layer 240 can include one or more electrodes (not shown). Although FIGS. 2A-2B illustrate layer 220 as including one electrode and layer 230 as including a plurality of electrodes, each layer can include any number of electrodes.

Figure 2C:
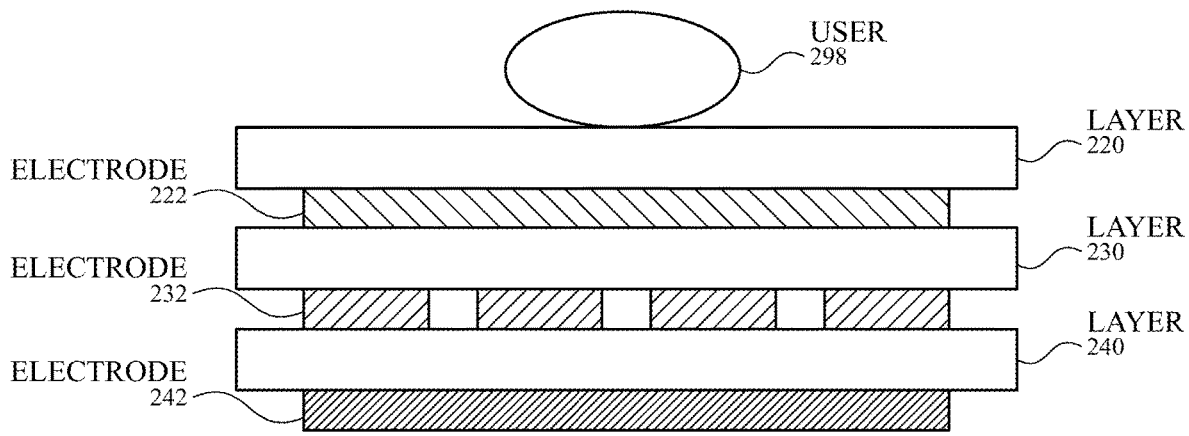
FIGS. 2C-2F illustrate cross-sectional views of an exemplary mat according to examples of the disclosure.

FIGS. 2C-2F illustrate cross-sectional views of an exemplary mat according to examples of the disclosure. The exemplary mat can be configured with any numbers of layers and/or arrangement of the layers relative to the other layers. For example, as illustrated in FIG. 2C, layer 220 can be located on one side of layer 230, and layer 240 can be located on the other side of layer 230. Electrode 222 disposed on layer 220 can be located on the side opposite of layer 220 than user 298. Electrode 232 can be located between layer 230 and layer 240. Electrode 242 can be located on the side of layer 240 opposite electrode 232.

Figure 2D:
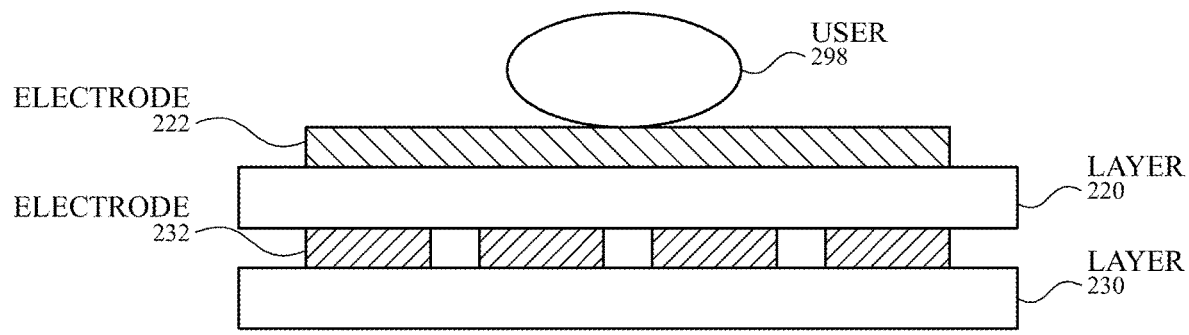
Figure 2E:
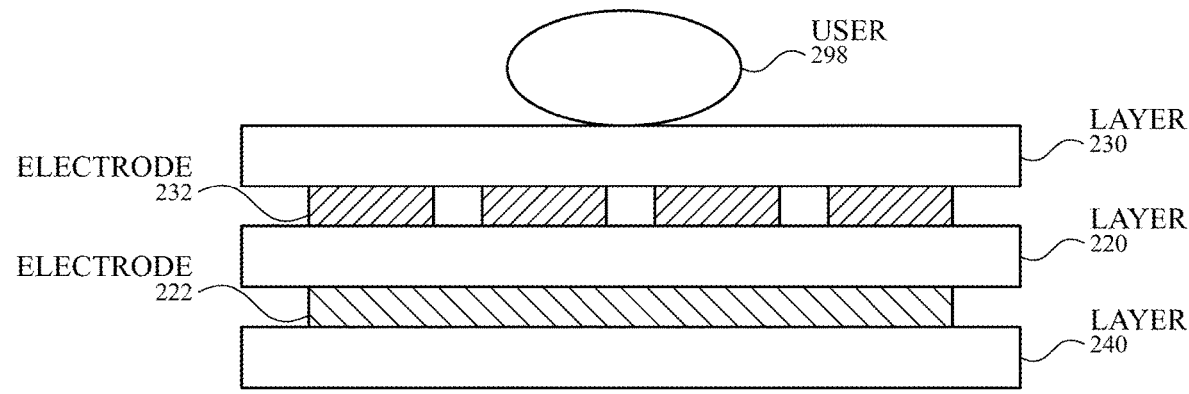
Figure 2F:
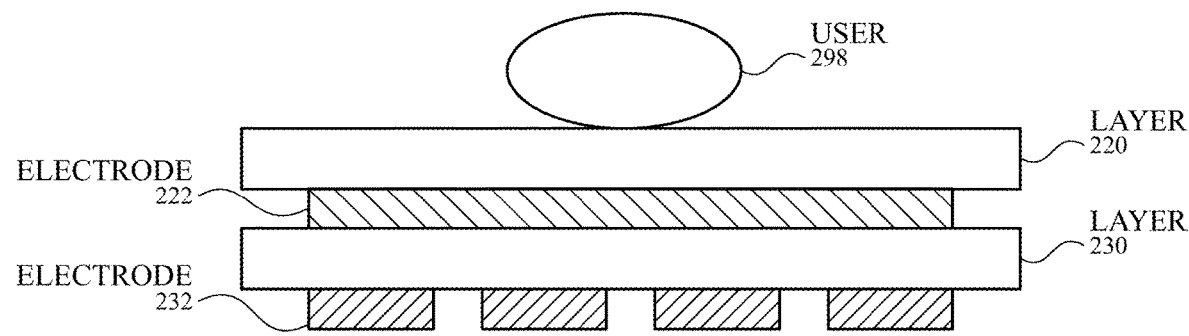

In some examples, as illustrated in FIG. 2D, electrode 222 can be located on one side of layer 220 closer to user 298 than layer 220. Electrode 232 can be located on the opposite side of layer 220 than user 298 and between layer 220 and layer 230. In some examples, as illustrated in FIG. 2E, electrode 232 can be located closer to user 298 than electrode 222. Electrode 232 can be disposed on layer 230, and electrode 222 can be disposed on layer 220. Layer 230 can be located closer to user 298 than electrode 232. Additionally, the exemplary mat can include layer 240 located on the opposite side of electrode 222 than layer 220. In some examples, as illustrated in FIG. 2F, layer 220 and electrode 222 can be located closer to the user than layer 230 and electrode 232. Although the figures illustrate one or more electrodes disposed on the corresponding layer, examples of the disclosure can include one or more electrodes embedded entirely or partially within the layer or disposed at least partially on the layer. Although the figures illustrate user 298 located on one side the exemplary mat, examples of the disclosure can include the exemplary mat being capable of functioning as a monitoring system regardless of the side user 298 is located. Furthermore, the exemplary monitoring system can be capable of functioning when user 298 is located in the center or edges of the mat.

Electrode 222, electrode 232, and/or electrode 242 can be configured with one or more functionalities. For example, electrode 222 and electrode 232 can be configured to measure a plurality of capacitance values. Electrode 222 can be configured as a sense electrode, and the plurality of electrodes 232 can be configured as drive electrodes. In some examples, electrode 222 can be configured as a drive electrode, and the plurality of electrodes 232 can be configured as sense electrodes. When an external force is applied, e.g., by the body weight of user 298, electrode 222 can move closer to electrode 232, which in turn, can cause a change (e.g., increase) in the mutual capacitance between the electrodes (i.e., sense and drive electrodes). In some examples, electrodes included in the plurality of electrodes 232 can be stimulated one at a time, and the capacitance associated with the stimulated electrode 222 can be measured by sense circuitry. In some examples, electrode 222 can include one or more sections of conductive material electrically coupled together. In some examples, the change in capacitance can be related to the distance between electrode 232 and electrode 222. One or more images of the strength or intensity of force applied by user 298 can be obtained based on the changes in capacitance.

In some examples, capacitance sensing can include measuring the capacitance at electrode 222, plurality of electrodes 232, or both relative to some reference, such as ground or a ground plane. The capacitance relative to the reference ground can be changed due to at least in part the presence of the user's body. In some examples, sensing can include resistive sensing, where the user's force or body weight can cause the electrodes to electrically contact. The electrodes can be driven and can cause conductive paths; electrically contacting the electrodes can cause a change in resistance (that can be measured as a change in current).

In some examples, electrode 242 (illustrated in FIG. 2C) can be configured as a shielding layer to shield the monitoring system from ambient noise. In some examples, electrode 242 can be coupled to drive circuitry, and drive circuitry can drive electrode 242 to a given voltage. In some examples, electrode 242 can be coupled to ground. Although electrode 242 and layer 240 are not illustrated in FIGS. 2D-2F, examples of the disclosure can include any number of substrates and any number of layers configured for shielding.

Figure 2G:
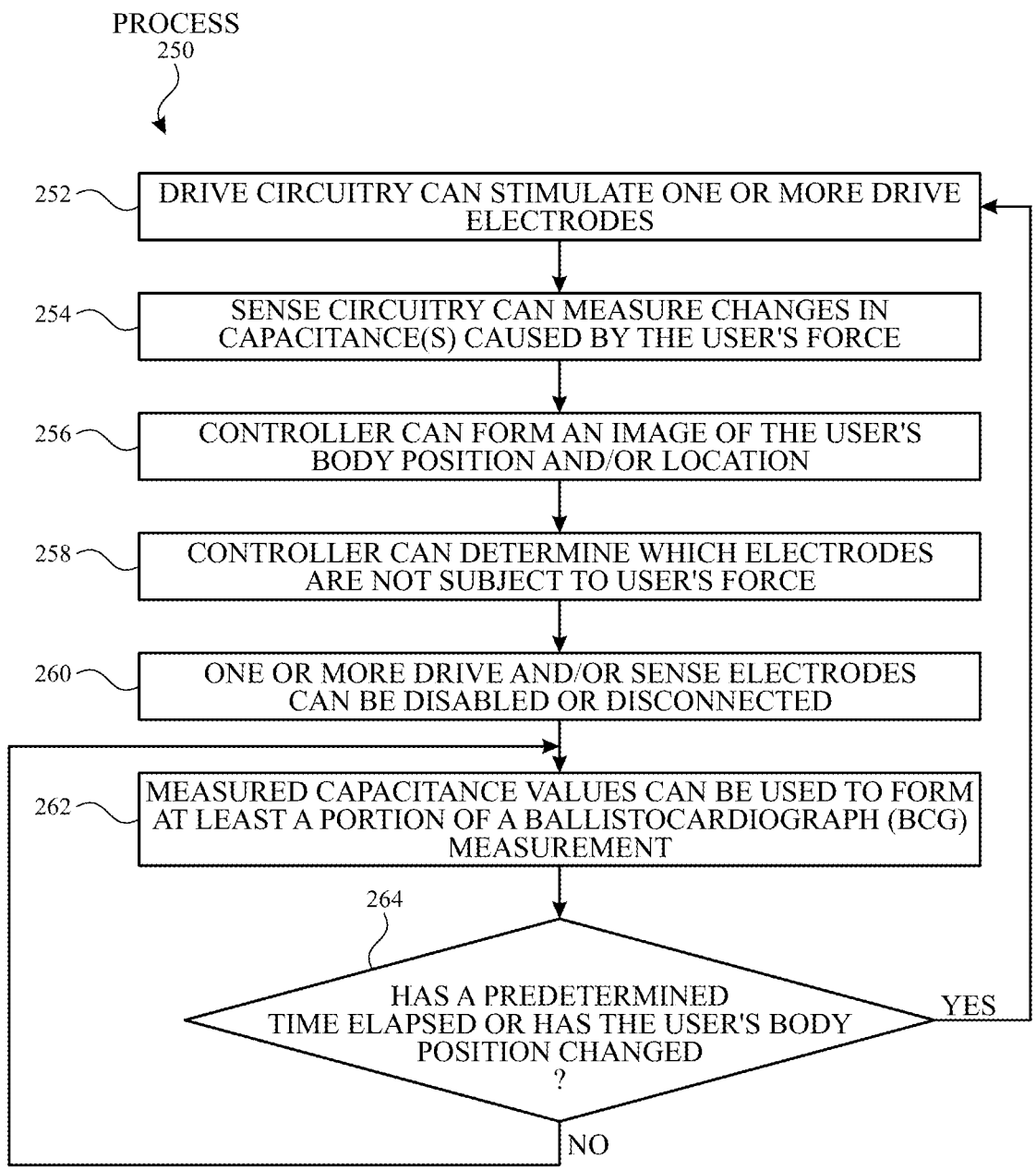
FIG. 2G illustrates an exemplary process flow for capacitive measurements according to examples of the disclosure.

The capacitance measurements can be used for detecting the position, location, and/or movement of the body of the user on the mat. FIG. 2G illustrates an exemplary process flow for capacitive measurements according to examples of the disclosure. Drive circuitry can stimulate one or more drive electrodes, creating a mutual capacitance with one or more sense electrodes (step 252 of process 250). Sense circuitry can be coupled to one or more sense electrodes. Sense circuitry can measure any changes in capacitance at the sense electrodes, where the changes in capacitance can be due to the user's force or body weight changing the distance between the electrodes (step 254 of process 250). A controller or processor coupled to sense circuitry can form an image of the user's position and/or location on the mat (step 256 of process 250). The controller or processor can determine which drive and/or sense electrodes are not affected by the user's force or body weight (step 258 of process 250). When the capacitance measurements are below a pre-determined threshold, the controller can disable or disconnect the drive and/or sense electrodes to conserve power, for example (step 260 of process 250). The measured capacitance values can be used to form at least a portion of a ballistocardiography (BCG) measurement (step 262 of process 250). In some examples, the measured capacitance values can be used to measure displacement of the user's body. The process can be repeated after a predetermined time interval and/or when the user's body position and/or location change (step 264 of process 250).

The BCG measurement, taken in step 262 of process 250, can include changes in electrodes properties due to fine body movement (e.g., caused by the flow of the user's blood with each heartbeat). As blood is being pumped, the user's body can move back and forth (e.g., in a longitudinal direction), and this back and forth movement can be measured by recording or monitoring the changes in capacitance over time. In some examples, the monitoring system can be configured such that measurements from the electrodes located in the immediate periphery (i.e., adjacent to the electrodes located directly under the body of the user) of the user are included in the BCG measurement; since electrodes located in the immediate periphery can be more sensitive to body movement than the electrodes located directly underneath the user's body (e.g., where measurements can be influenced by gross motion). The BCG measurement can be used at least partially to measure the heart rate, heart rate variability, respiratory rate, and/or respiratory rate variability.

Figure 2H:
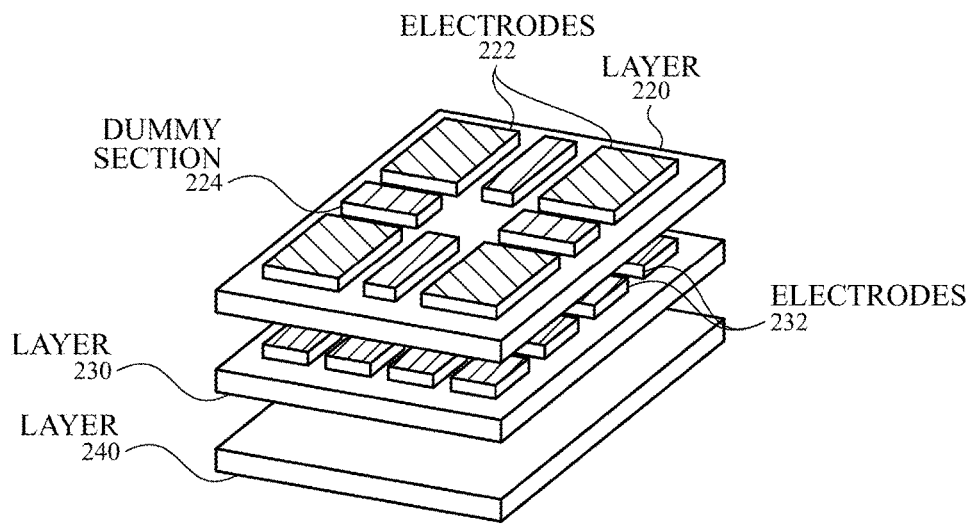
FIG. 2H illustrates an exemplary perspective view of layers included in an exemplary mat according to examples of the disclosure.

In some examples, the mat can include one or more dummy sections. FIG. 2H illustrates an exemplary perspective view of layers included in an exemplary mat according to examples of the disclosure. In some examples, layer 220 can include one or more dummy sections 224. Dummy sections 224 can be configured to prevent neighboring electrodes from capacitively coupling to each other. In some examples, dummy sections 224 can be floating. In some examples, dummy sections 224 can be coupled to ground or drive circuitry. In some examples, layer 230 can, additionally or alternatively, include dummy sections (not shown).

Figure 3A:
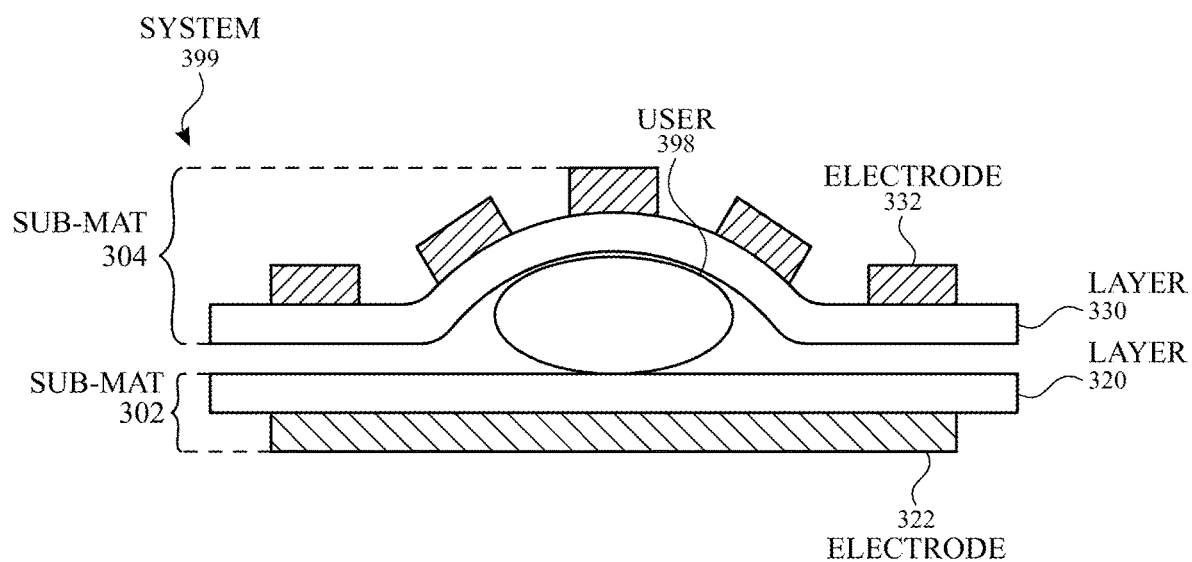
FIG. 3A illustrates a cross-sectional view of an exemplary monitoring system including a mat according to examples of the disclosure.

In some examples, the layers included in the mat can be spatially separated. FIG. 3A illustrates a cross-sectional view of an exemplary monitoring system including a mat according to examples of the disclosure. System 399 can include sub-mat 302 and sub-mat 304. In some examples, user 398 can be located between sub-mat 302 and sub-mat 304. Sub-mat 302 and sub-mat 304 can be configured with any number of layers and/or arrangement of the layers relative to the other layers. For example, sub-mat 302 can include layer 320 and electrode 322. Although the figure illustrates layer 320 located closer to user 398 than electrode 322 and layer 330 located closer to user 398 than electrode 332, examples of the disclosure can include electrode 332 located closer to user 398 than layer 330, electrode 322 located closer to user 398 than layer 320, or both. The design and/or operation of layer 330, plurality of electrodes 332, and electrode 322 can include the design and/or operation of layer 230, plurality of electrodes 232, and electrode 222, respectively, as discussed above. Sub-mat 304 can include layer 330 and plurality of electrodes 332.

With user 398 located between sub-mat 302 and sub-mat 304, one or more parts of user 398 can cause a change in the distance between plurality of electrodes 322 and electrode 332. The change in distance between electrodes can be caused by physical properties (e.g., size) of the user's body parts and/or the user's position (e.g., the user can be laying on the user's side). For example, a lower mutual capacitance in one or more regions compared to other regions can be indicative of the presence of one or more user's body parts located between sub-mat 302 and sub-mat 304. In some examples, system 399 can be configured to approximate the location of one or more user's body parts based on the capacitance value. For example, if the user is sleeping on his or her back (as illustrated in FIG. 3A), regions with lower mutual capacitance can be associated with body parts (e.g., arms or legs) having a lower profile. Regions with higher mutual capacitance can be associated with body parts (e.g., chest) having a higher profile. Alternatively, a lower mutual capacitance can be associated with the user lying on the user's back, and a higher mutual capacitance can be associated with the user lying on the user's side, for example. The capacitance measurements can include process 250 (illustrated in FIG. 2G) or self-capacitance measurements, discussed above.

In one or more regions where sub-mat 302 and sub-mat 304 can be contacting, electrode 322 can be in close proximity to electrode 332 and the mutual capacitance can be larger than in regions where sub-mat 302 and sub-mat 304 can be contacting. In some examples, plurality of electrodes 332 can be stimulated one at a time and the capacitance associated with the stimulated electrode 332 can be measured by circuitry coupled to electrode 322. In some examples, electrode 322 can include one or more sections of conductive material electrically coupled together.

Figure 3B:
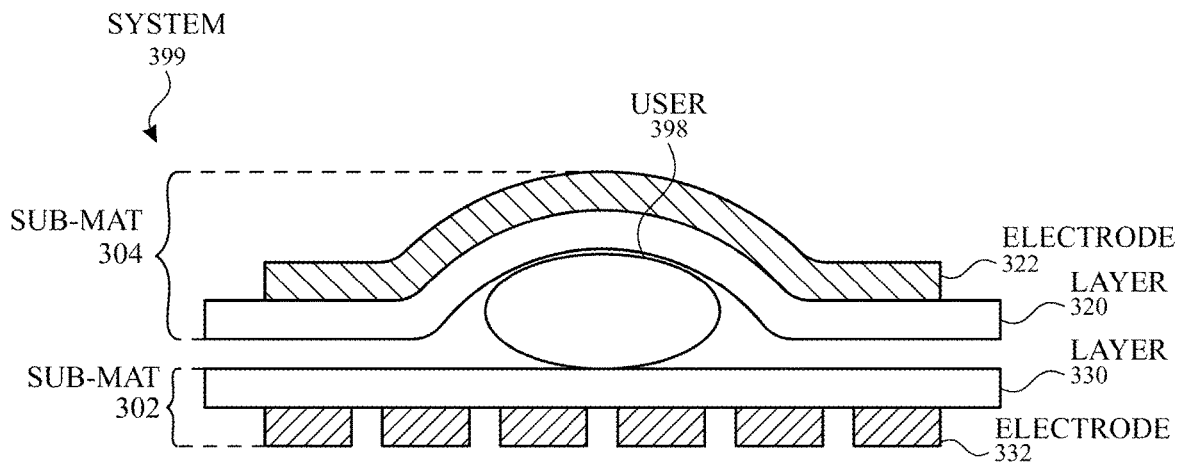
FIGS. 3B-3C illustrate cross-sectional views of exemplary mats according to examples of the disclosure.
Figure 3C:
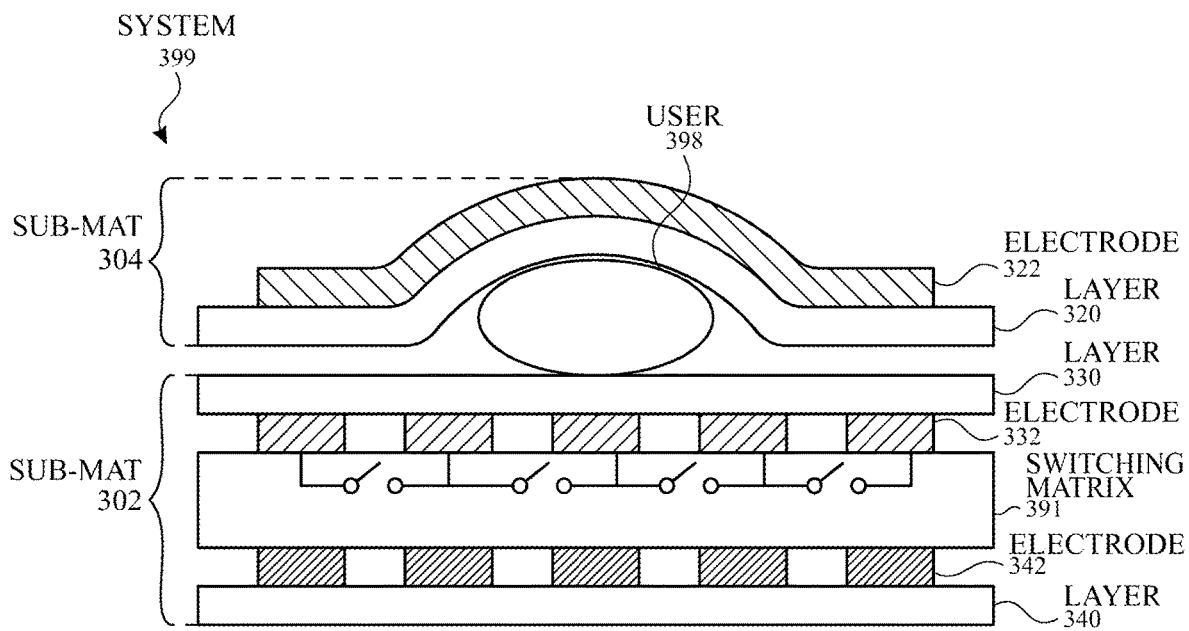

FIGS. 3B-3C illustrate cross-sectional views of exemplary mats according to examples of the disclosure. In some examples, as illustrated in FIG. 3C, system 399 can be configured with the plurality of electrodes 332 included in sub-mat 302 and electrode 322 included in sub-mat 304. Although FIG. 3C illustrates layer 320 located closer to user 398 than electrode 322 and layer 330 located closer to user 398 than electrode 332, examples of the disclosure can include plurality of electrodes 332 located closer to user 398 than layer 330, electrode 322 located closer to user 398 than layer 320, or both.

In some examples, sub-mat 302 can include a switching matrix 391, as illustrated in FIG. 3C. Sub-mat 302 can include a plurality of layers of electrodes, such as plurality of electrodes 332 disposed on layer 330 and plurality of electrodes 342 disposed on layer 340. Switching matrix 391 can be configured to electrically couple one or more electrodes included in the plurality of electrodes 332 together. System 399 can be capable of dynamically switching one or more electrodes utilized for the capacitance measurements. For example, in a first mode, user 398 can be located between sub-mat 302 and sub-mat 304. Electrode 322 can be configured as a sense electrode, and the plurality of electrodes 332 can be configured as drive electrodes. Changes in capacitance values can be due to the user's body parts increasing the separations between the sense and drive electrodes. In a second mode, sub-mat 304 can be removed from system 399 or located a certain distance away. The separation between sub-mat 304 from sub-mat 302 can prevent electrode 322 from capacitively coupling to plurality of electrodes 332, or the measured capacitance values can be below a predetermined threshold.

Switching matrix 391 can electrically couple together the plurality of electrodes 332. The electrically coupled electrodes 332 can be configured as a sense electrode, and the plurality of electrodes 342 can be configured as drive electrodes. Changes in capacitance values can be due to the user's body weight applying a force that can change the distance between the sense and drive electrodes. When sub-mat 304 is returned back to system 399 and located a close enough distance such that electrode 322 can capacitively couple to electrode 332 (or the measured capacitance values can become greater than the predetermined threshold), system 399 can either remain in the second mode or switch to the first mode.

In some examples, drive circuitry can drive two or more electrodes differently. For examples, one or more electrodes can be driven by the drive circuitry, whereas other electrodes may not. The system can switch which electrodes to capacitively couple. For example, in a first operation mode, the system can drive electrodes located in sub-mat 302 (or sub-mat 304) to capacitively couple with sense electrodes also located in sub-mat 302 (or sub-mat 304). In a second operation mode, the system can drive electrodes located in sub-mat 302 (or sub-mat 304) to capacitively couple with sense electrodes located in sub-mat 304 (or sub-mat 302). In some examples, the system can alternate (e.g., time multiplex) between the first and second operation modes. In some examples, the electrodes can be driven with different stimulation signals.

Figures 1, 3D:
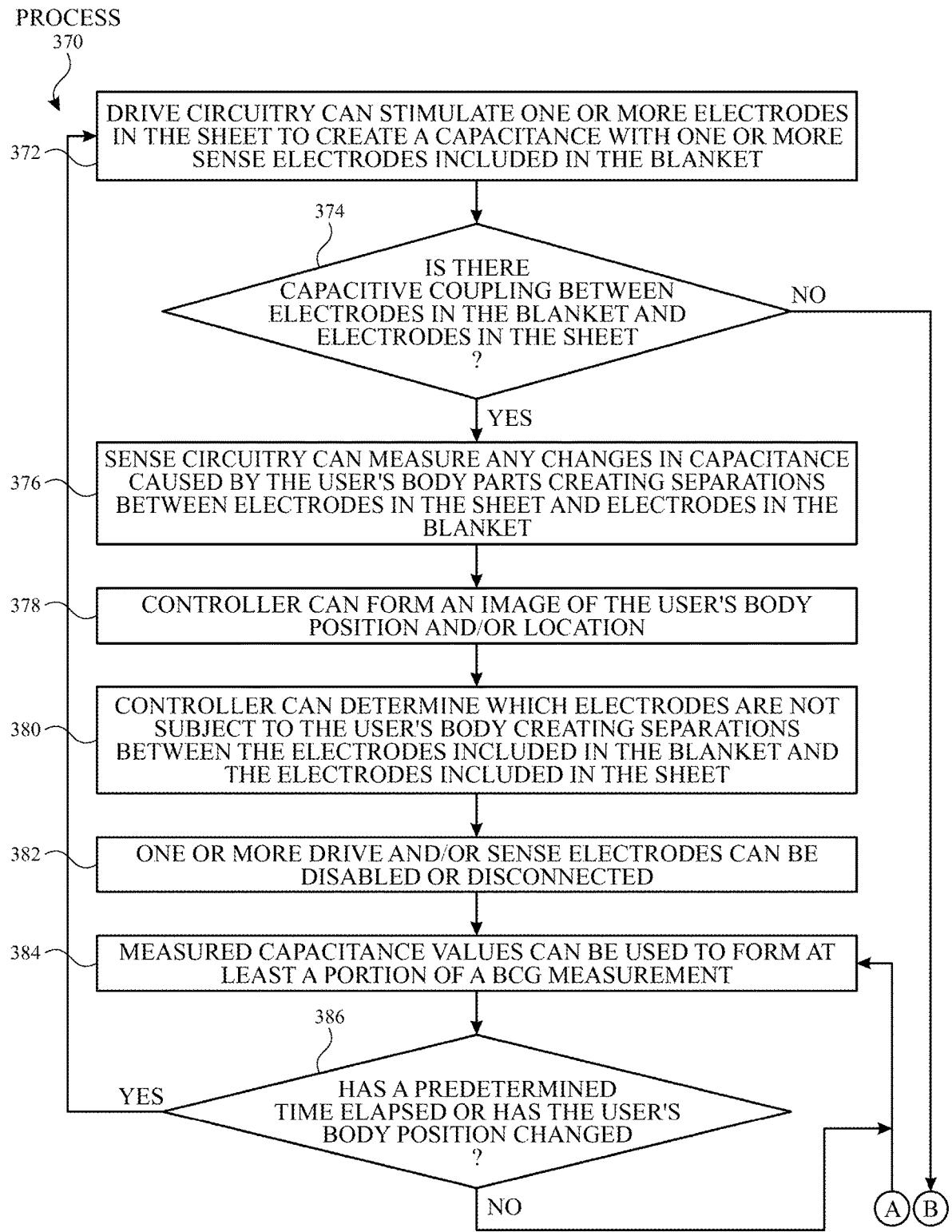
Figures 2, 3D:
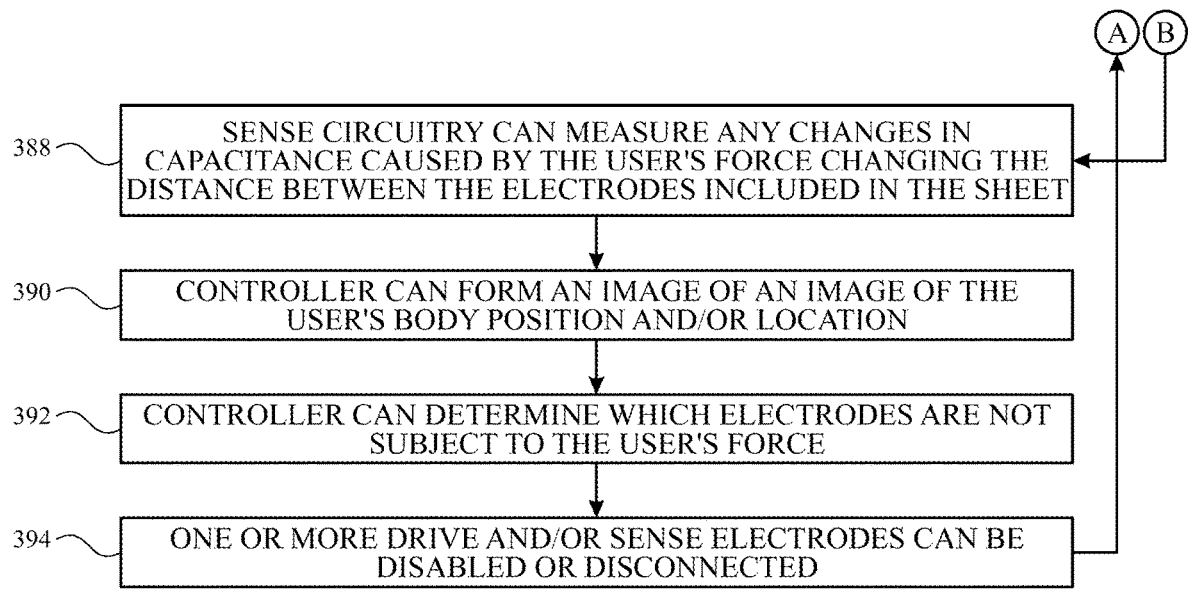

FIGS. 3D-1 and 3D-2 illustrate an exemplary process flow for dynamically switching one or more electrodes utilized for capacitance measurements according to examples of the disclosure. Drive circuitry can stimulate one or more drive electrodes included in the mat to create a capacitance with one or more sense electrodes (step 372 of process 370). Sense circuitry can be coupled to one or more sense electrodes. Sense circuitry can determine whether the drive electrodes can capacitively couple to the electrodes (step 374 of process 370). If there is capacitive coupling (or whether the measured capacitance values are greater than a predetermined threshold), the system can switch to the first mode of measuring capacitance values. Sense circuitry can measure any changes in capacitance caused by the user's body parts creating separations or changes in distances between the drive electrodes and the sense electrodes (step 376 of process 370). A controller or processor coupled to sense circuitry can form an image of the user's body position and/or location (step 378 of process 370). The image can comprise matrix of capacitance values. The controller or processor can determine which drive and/or sense electrodes are not affected by the presence of the user's body (e.g., creating separations or reducing the gap between drive and sense electrodes) (step 380 of process 370) and can disable or disconnect the drive and/or sense electrodes to conserve power, for example (step 382 of process 370). The measured capacitance values can be used to form at least a portion of a BCG measurement (step 384 of process 370). The process can be repeated after a predetermined time interval and/or when the user's body position and/or location change (step 386 of process 370).

If there is no capacitively coupling or if the measured capacitance values are below a pre-determined threshold (determined in step 374 of process 370), the system can switch to the second mode of measuring capacitance values. Sense circuitry can measure any changes in capacitance caused by the user's force changing the distance between the drive and sense electrodes (step 388 in process 370). A controller or processor coupled to sense circuitry can form an image of the user's body position and/location on the mat (step 390 of process 370). The controller or processor can determine which drive and/or sense electrodes are not affected by the user's force or body weight (step 392 of process 370) and can disable or disconnect the drive and/or sense electrodes to conserve power, for example (step 394 of process 370). The measured capacitance values can be used to form at least a portion of a BCG measurement (step 384 of process 370). The process can be repeated after a predetermined time interval and/or when the user's body position and/or location change (step 386 of process 370). Although FIGS. 3D-1 and 3D-2 illustrate process 370 as including the determination of whether there is capacitively coupling between the electrodes in the sub-mats after or while stimulating the drive electrodes, examples of the disclosure can include this determination at any time. For example, the system can be configured to periodically determine whether there is capacitive coupling regardless of what step in the process the system is in.

Figure 3E:
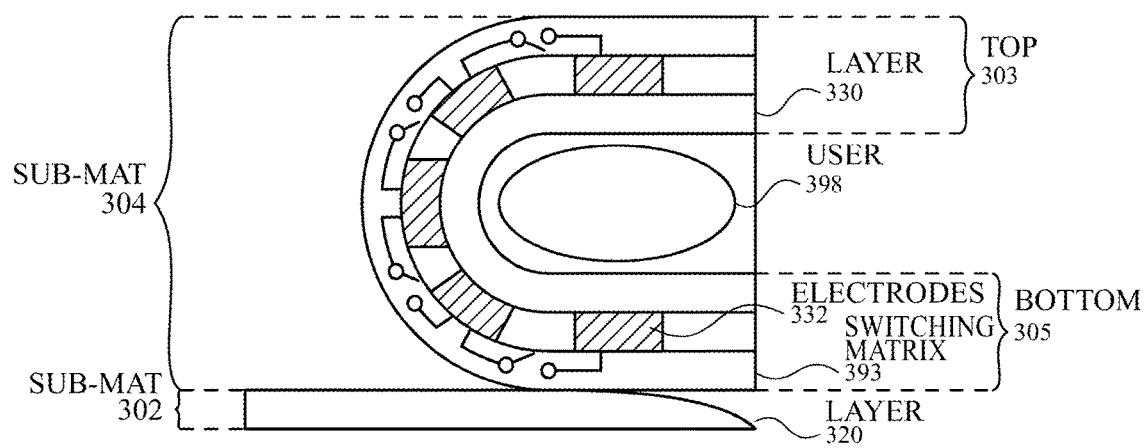
FIG. 3E illustrates a cross-sectional view of an exemplary mat including a switching matrix according to examples of the disclosure.

In some examples, the sub-mat can be capable of being folded and can include a switching matrix to dynamically reconfigure the measurements for such a situation. FIG. 3E illustrates a cross-sectional view of an exemplary mat including a switching matrix according to examples of the disclosure. Sub-mat 304 can include layer 330, plurality of electrodes 332, and switching matrix 393. In some examples, sub-mat 304 can be folded over such that user 398 can be located between top 303 of sub-mat 304 and bottom 305 of sub-mat 304. Sub-mat 304 can be configured to measure the capacitance between the plurality of electrodes 332 located in top 303 of sub-mat 304 and the plurality of electrodes 332 located in bottom 305 of sub-mat 304. Switching matrix 393 can be configured to couple together some of the plurality of electrodes 332 located in one portion (e.g., bottom 305) of sub-mat 304. The electrically coupled electrodes located in the one portion (e.g., bottom 305) can form a mutual capacitance to one or more of the plurality of electrodes 332 located in another portion (e.g., top 303) of sub-mat 304.

To determine whether sub-mat 304 is folded and/or located in close proximity to sub-mat 302, a test scan can be performed. The test scan can include coupling one or more electrodes 332 (or electrodes included in sub-mat 302) to drive circuitry and coupling other electrodes (e.g., other electrodes 332) to sense circuitry. In some examples, the test can include multiple combinations of different electrodes coupled to drive circuitry and different electrodes coupled to sense circuitry. Based on the combination of drive electrodes and sense electrodes where a capacitance value is greater than a pre-determined threshold, the location and/or configuration of sub-mat 302 and sub-mat 304 can be determined.

Figure 4A:
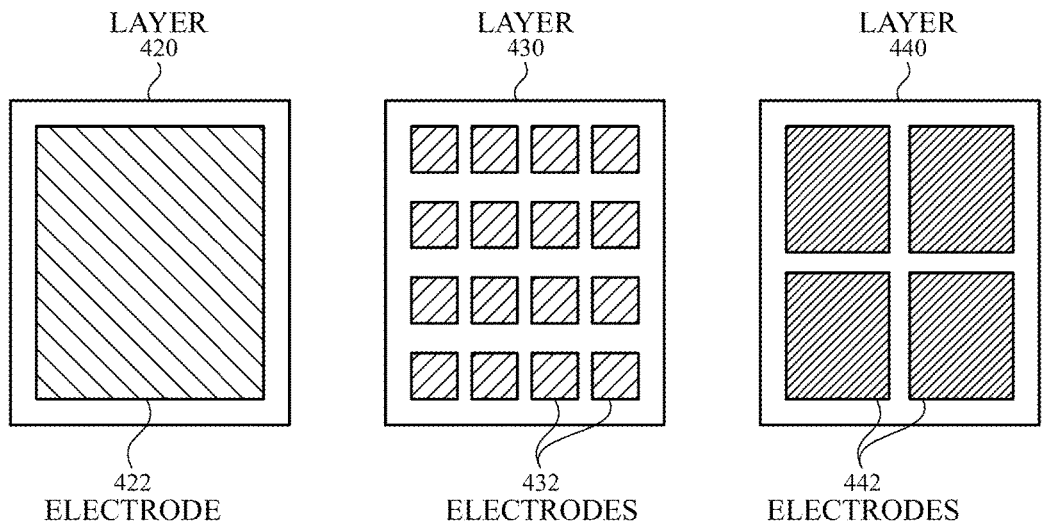
FIGS. 4A-4C illustrate top, perspective, and cross-sectional views of layers included in an exemplary mat according to examples of the disclosure.
Figure 4B:
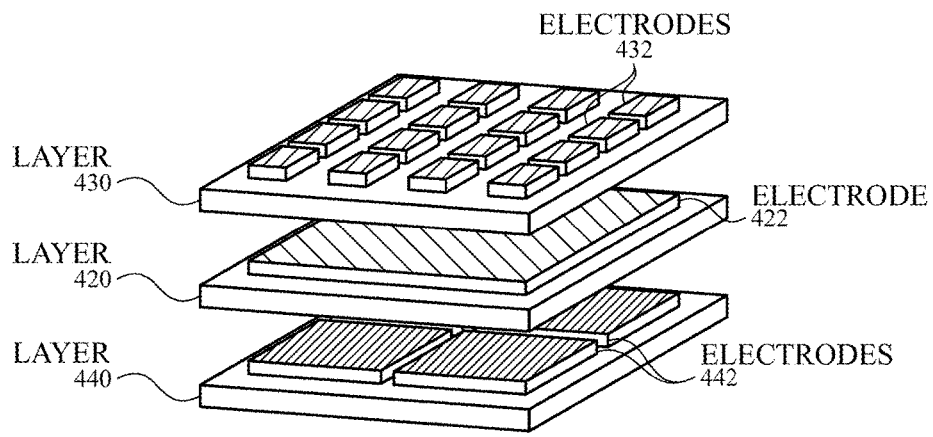
Figure 4C:
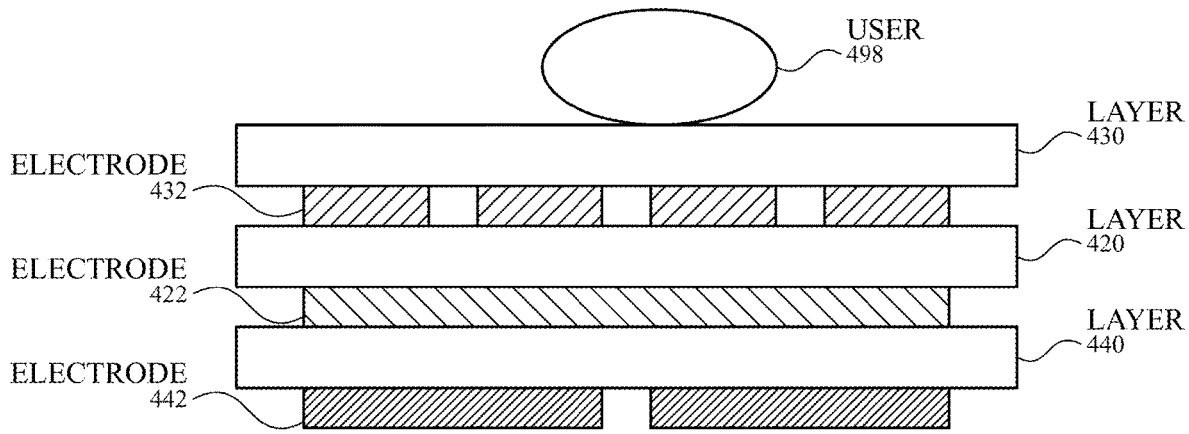

FIGS. 4A-4C illustrate top, perspective, and cross-sectional views of layers included in an exemplary mat according to examples of the disclosure. The exemplary mat can include layer 420, layer 430, and layer 440. Layer 420 can include electrode 422, and layer 430 can include a plurality of electrodes 432. The design and/or operation of layer 420, layer 430, layer 440, electrode 422, and plurality of electrodes 432 can include the design and/or operation of layer 220, layer 230, layer 240, electrode 222, and plurality of electrodes 232, respectively, as discussed above.

In some examples, plurality of electrodes 442 can be configured with a higher granularity than electrode 422 and/or plurality of electrodes 432. Changes in granularity can be obtained in one or more ways including, but not limited to, different materials and/or material properties, different configurations of coupled electrodes, and different size electrodes. In some examples, electrode 422 and/or plurality of electrodes 432 can be configured with a higher granularity than plurality of electrodes 442. In some examples, the number of electrodes 432 disposed on layer 430 can be greater than the number of electrodes 442 disposed on layer 440. In some examples, the number of electrodes 432 disposed on layer 430 can be less than or equal to the number of electrodes 442 disposed on layer 440 (not shown). In some examples, two or more of electrode 422, plurality of electrodes 432, and plurality of electrodes 442 can include any conductive material including, but not limited to, silver, copper, gold, aluminum, steel, brass, bronze, and graphite. In some examples, two or more of electrode 422, plurality of electrodes 432, and plurality of electrode 442 can include the same materials.

In some examples, the exemplary mat can include an additional layer (not shown) configured to provide support or electrical insulation from one or more materials or layers (e.g., the mattress). In some examples, the additional layer can include one or more electrodes (not shown).

In some examples, the monitoring system can include one or more shielding electrodes to limit capacitive coupling of the system with external sources. In some examples, the one or more shielding electrodes can be a separate layer in the system. In some examples, one or more of the plurality of electrodes 432, plurality of electrodes 442, or both can be configured as shielding electrodes. In some examples, one or more of the plurality of electrodes 432 (and/or plurality of electrodes 442) can be configured to measure electrical signals and one or more adjacent electrodes 432 (and/or plurality of electrodes 442) can be configured for shielding.

The exemplary mat can be configured with any number of layers and/or arrangement of layers relative to the other layers. For example, as illustrated in FIG. 4C, layer 430 can be located on one side of layer 420, and layer 440 can be located on the other side of layer 420. Plurality of electrodes 432 disposed on layer 430 can be located on the opposite side of layer 430 than user 498. Electrode 422 can be located between layer 420 and layer 440, and plurality of electrodes 442 can be located on the opposite side of layer 440 than electrode 422.

In additional to measuring changes in capacitance to form one or more images of the user's position and form at least a portion of a BCG measurement, the plurality of electrodes 442 can be configured for sensing electrical signals. The measured electrical signals can be used to form at a least a portion of an electrocardiogram (ECG) measurement. The ECG measurement can include changes in electrical impulses due to heart contractions and blood flow. In some examples, the monitoring system can be configured such that measurements from the electrodes located directly underneath the user's body are included in the ECG measurement, since these electrodes can have higher coupling to the user's electrical impulses. In some examples, the electrodes located directly under the user's body can be effected by less movement than electrodes located in the immediate periphery (i.e., adjacent to the electrodes located directly under the body of the user) of the user's body. The ECG measurement can be used at least partially to measure the heart rate, heart rate variability, respiratory rate, and/or respiratory rate variability.

Figures 1, 4D:
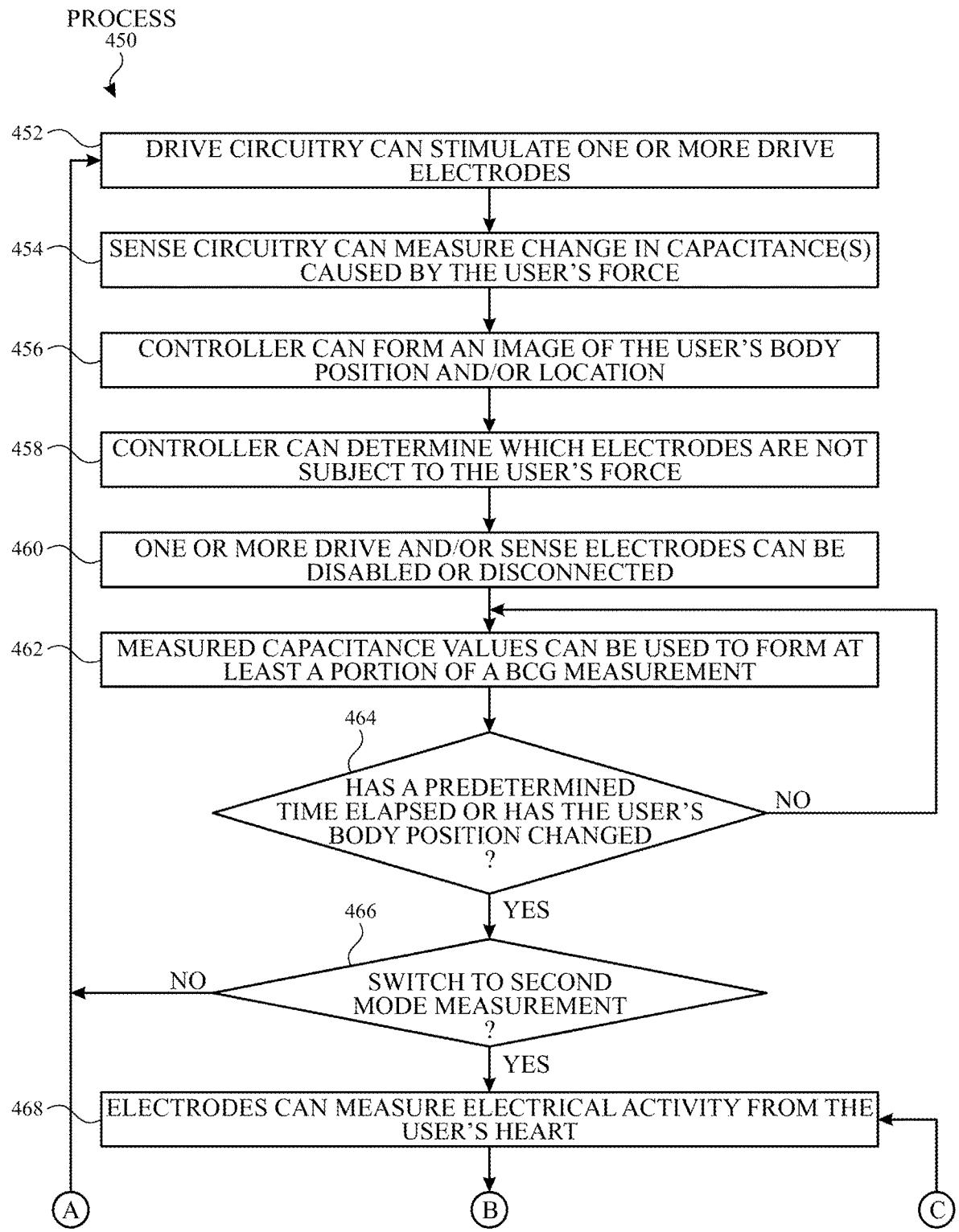
Figures 2, 4D:
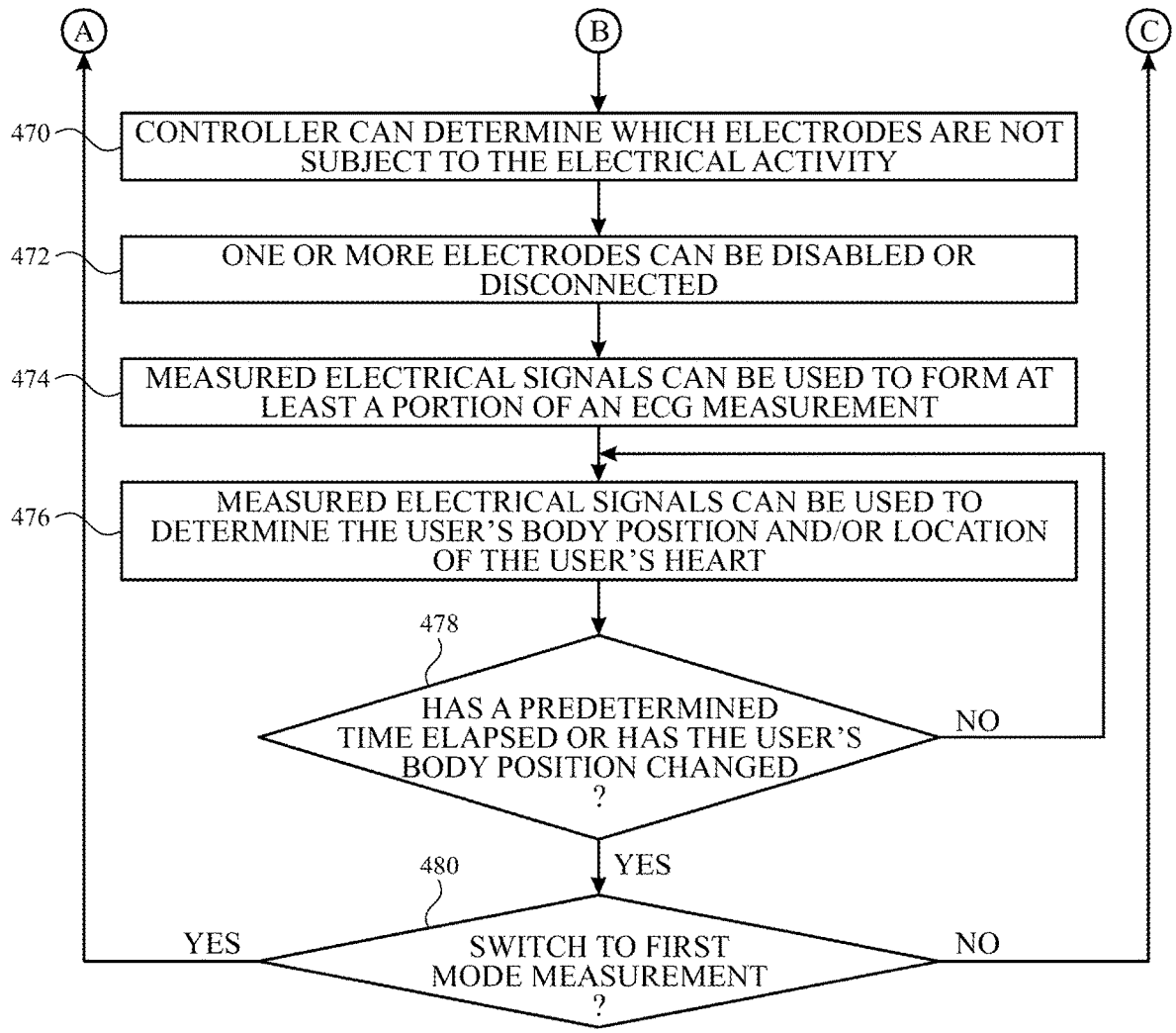

FIGS. 4D-1 and 4D-2 illustrate an exemplary process flow for capacitive and electrical measurements according to examples of the disclosure. In some examples, the monitoring system can operate in multiple modes: one mode (i.e., first mode) for measuring capacitance values and another mode (i.e., second mode) for measuring electrical signals. During the first mode, drive circuitry can stimulate one or more drive electrodes creating a mutual capacitance with one or more sense electrodes (step 452 of process 450). Sense circuitry can be coupled to one or more sense electrodes. Sense circuitry can measure any changes in capacitance caused by the user's force that can change the distance between the drive and sense electrodes (step 454 of process 450). A controller or processor coupled to sense circuitry can form an image of the user's body position and/or location on the mat (step 456 of process 450). The controller or processor can determine which drive and/or sense electrodes are not affected by the user's force or body weight (step 458 of process 450) and can disable or disconnect the drive and/or sense electrodes to conserve power, for example (step 460 of process 450). In some examples, the controller can select the drive and/or sense electrodes that are located in the immediate periphery of the user's body or the periphery of the mat for the capacitive measurements. The measured capacitance values can be used to form at least a portion of a BCG measurement (step 462 of process 450). The first mode can be repeated after a predetermined time interval and/or when the user's body position and/or location change (step 464 of process 450). In some examples, the first mode can be repeated after the second mode has been completed (step 466 of process 450).

During the second mode, one or more electrodes can be configured to measure the electrical impulses from the user's heart (step 468 of process 450). In some examples, the difference in electrical potential between multiple electrodes can be measured. The controller or processor can determine which electrodes are not affected by the electrical signals of the user's heart (step 470 of process 450) and can disable or disconnect the electrodes to conserve power, for example (step 472 of process 450). In some examples, the controller can select the electrodes located underneath the user's body for electrical measurements. The measured electrical signals can be used to form at least a portion of an ECG measurement (step 474 of process 450). In some examples, the electrical signals can be used to determine the user's body position, user's body location, the location of the user's heart, or a combination thereof (step 476 of process 450). In some examples, step 456 can be used to form a rough estimate or coarse image of the user's body position and/or location, and step 474 can be used to form a more detailed or finer imager of the user's body position and/or location. The second mode can be repeated after a predetermined time interval and/or when the user's body position and/or location change (step 478 of process 450). In some examples, the second mode can be repeated after the first mode has been completed (step 480 of process 450).

Although FIGS. 4D-1 and 4D-2 illustrate the controller beginning with the first mode measurement, examples of the disclosure can include beginning with the second mode measurement or beginning with both the first and second mode measurements. Although FIG. 4D illustrates the controller performing the first and second mode measurements sequentially, examples of the disclosure can include performing the first and second mode measurements concurrently. Moreover, examples of the disclosure can include using information measured during one mode (e.g., first mode) for and/or in conjunction with another mode (e.g., second mode).

Figure 4E:
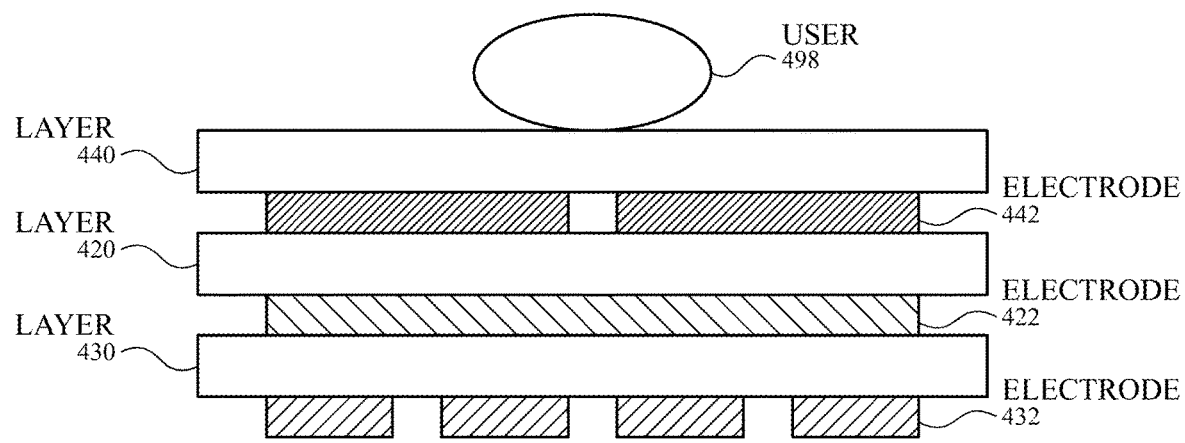
FIG. 4E illustrates a cross-sectional view of an exemplary mat according to examples of the disclosure.

FIG. 4E illustrates a cross-sectional view of an exemplary mat according to examples of the disclosure. In some examples, the plurality of electrodes 442 can be configured to measure the electrical signals from the heart of user 498. Configuring the monitoring system such that the plurality of electrodes 442 are located at or near the surface of user 498 can lead to more accurate measurements of the electrical signals. In some examples, layer 440 can be located on one side of layer 420, and layer 430 can be located on the opposite side of layer 420. Plurality of electrodes 442 can be located on one side of layer 440, and user 498 can be located either on the same side of layer 440 (not shown) or on the opposite side of layer 440. Electrode 422 can be located between layer 420 and layer 430. Plurality of electrodes 432 can be located on the opposite side of layer 430 than the side that electrode 422 is located on.

Figure 4F:
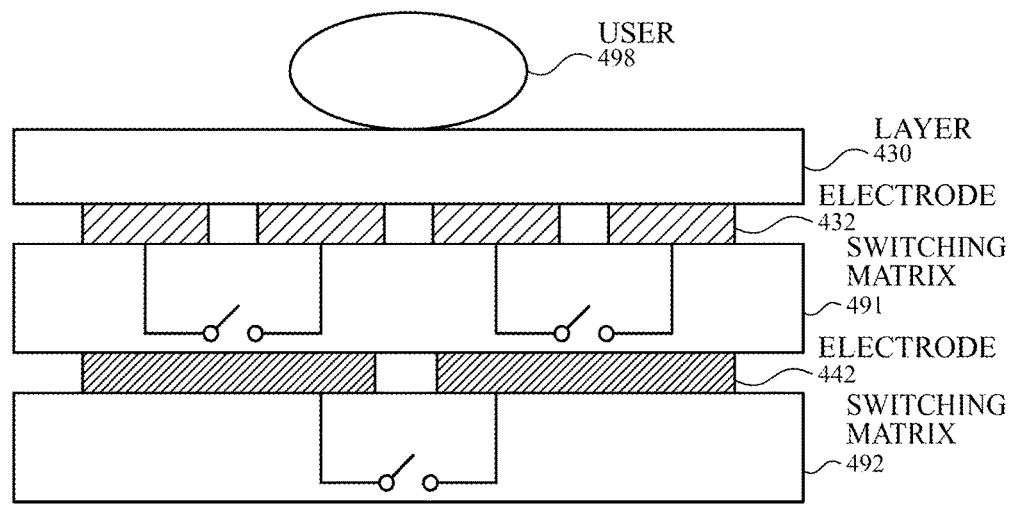
FIG. 4F illustrates a cross-sectional view of an exemplary mat according to examples of the disclosure.

FIG. 4F illustrates a cross-sectional view of an exemplary mat according to examples of the disclosure. In some examples, the number of layers including electrodes can be reduced and/or the functionality of one or more electrodes can be dynamically switched by including one or more switching matrices, such as switching matrix 491 and switching matrix 492. Switching matrix 491 can be configured to couple or decouple one or more of the plurality of electrodes 432, and switching matrix 492 can be configured to couple or decouple one or more of the plurality of electrodes 442.

In some examples, switching matrix 491 and switching matrix 492 can be configured for capacitive measurements. Switches included in switching matrix 491 can be configured such that the plurality of electrodes 432 can be electrically isolated from one another and coupled to drive circuitry. Switches included in switching matrix 492 can be configured such that the electrodes in the plurality of electrodes 442 can be electrically coupled together and coupled to sense circuitry.

In some examples, switching matrix 491 and switching matrix 492 can be configured for ECG measurements and (optional) shielding. Switches included in switching matrix 491 can be configured such that the plurality of electrodes 432 can be electrically isolated from one another. The plurality of electrodes 432 can be configured to measure the electrical signals of user 498. The switches included in switching matrix 491 can be configured such that the electrodes in the plurality of electrodes 442 are electrically coupled together and function as a shielding layer.

In some examples, switching matrix 491 and switching matrix 492 can be configured to have different granularities in the mat based on the user's body position and/or location. For example, the switching matrix can decouple electrodes for more granularity in locations where the user's body parts may require a more sensitive measurement (e.g., the area corresponding to the user's heart), or couple electrodes for less granularity in locations where less sensitive measurements are acceptable (e.g., areas where the user's body may not be present).

Figure 5A:
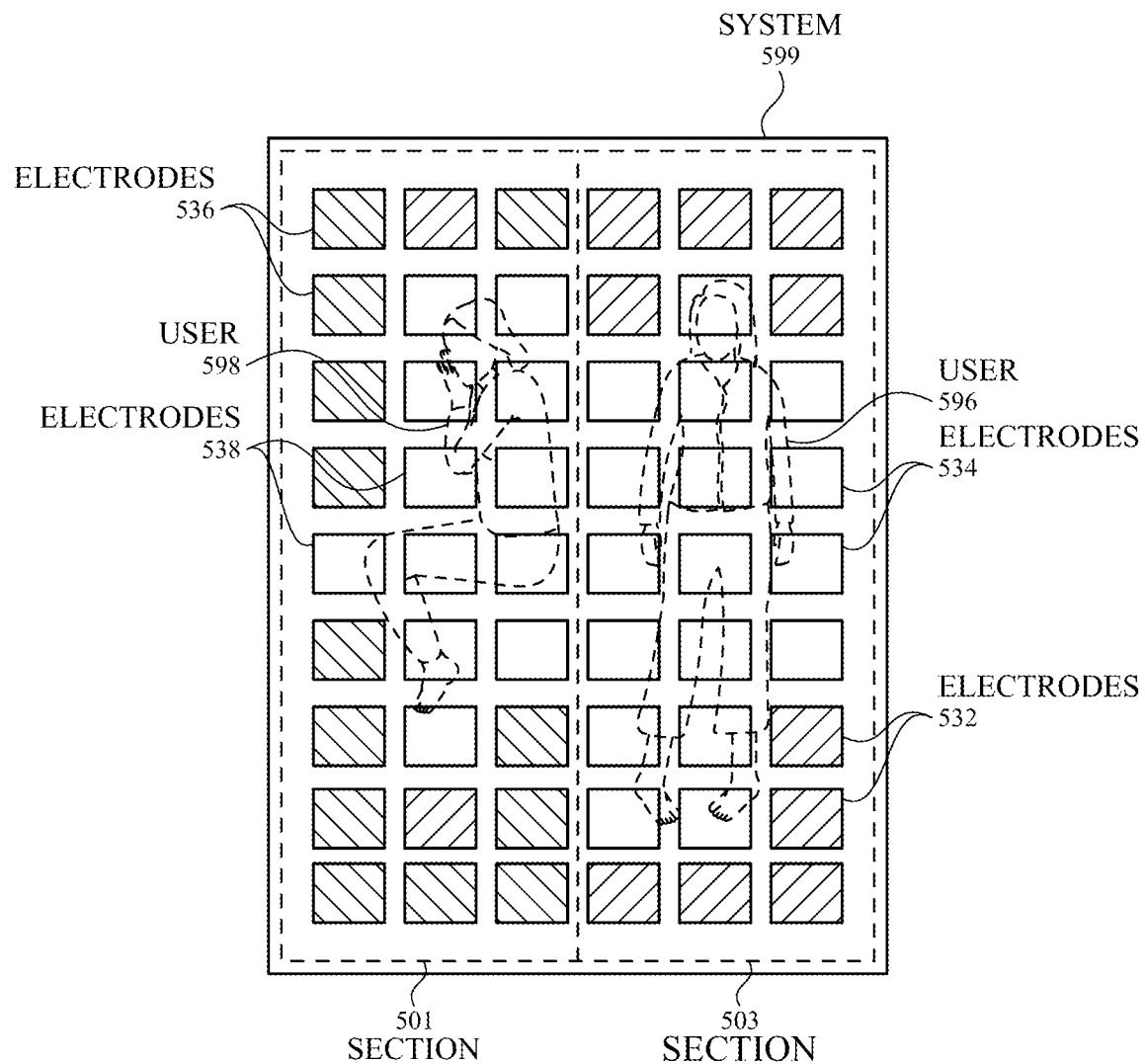
FIG. 5A illustrates a top view of an exemplary monitoring system including multiple sections according to examples of the disclosure.

In some examples, the monitoring system can include one or more switching matrices, where the switching matrices can be configured to partition (e.g., separate measurement information) the mat into multiple sections. FIG. 5A illustrates a top view of an exemplary monitoring system including multiple sections according to examples of the disclosure. System 599 can include a plurality of electrodes, such as plurality of electrodes 532, plurality of electrodes 534, plurality of electrodes 536, and plurality of electrodes 538. Multiple users, such as user 596 and user 598, can be positioned on system 599. System 599 can determine that there are multiple users and can partition system 599 into multiple sections, such as section 501 and section 503. In some examples, measurements in one section, such as section 501, can be taken independently from measurements in another section, such as section 503. In some examples, the plurality of sections can be specified at the time of manufacture. In some examples, the size, number, and/or shape of the plurality of sections can be dynamically configured using one or more switching matrices. For example, system 599 can associate user 598 with section 501 and user 596 with section 503. For capacitance measurements, system 599 can couple section 501 to a first drive and sense circuitry using a switching matrix and can couple section 503 to a second drive and sense circuitry using the same or another switching matrix. The system can be configured to capture a plurality of images, where each image can include a matrix of measurement values that represent the position of the user within a given section. Additionally, a plurality of measurements of electrical signals can be taken, such as a measurement of electrical signals in section 501 that can be separate and independent from the measurement of electrical signals in section 503. System 599 can associate each measurement with a given user or a given section and can perform analysis specific to that user or section.

Figures 1, 5B:
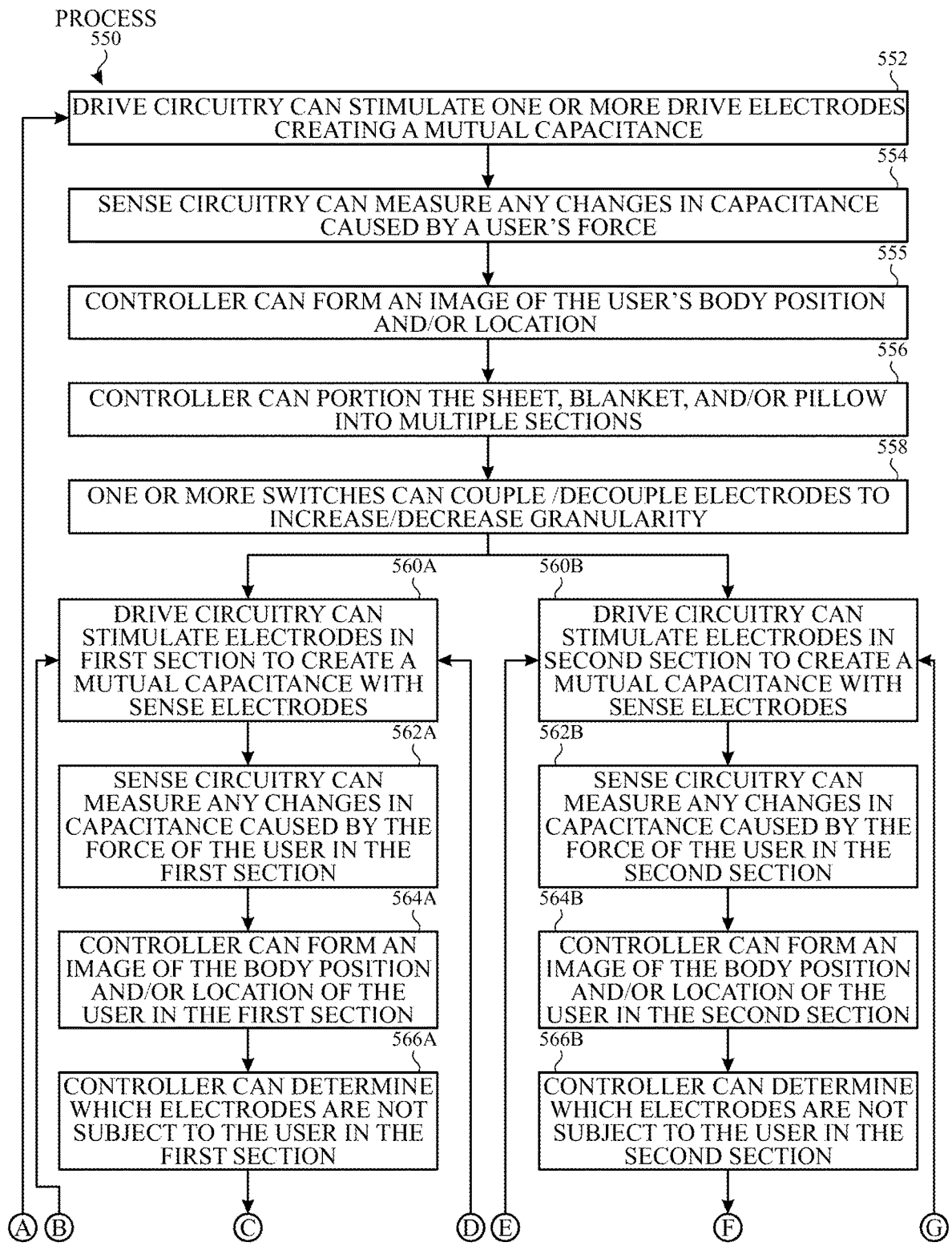
Figures 2, 5B:
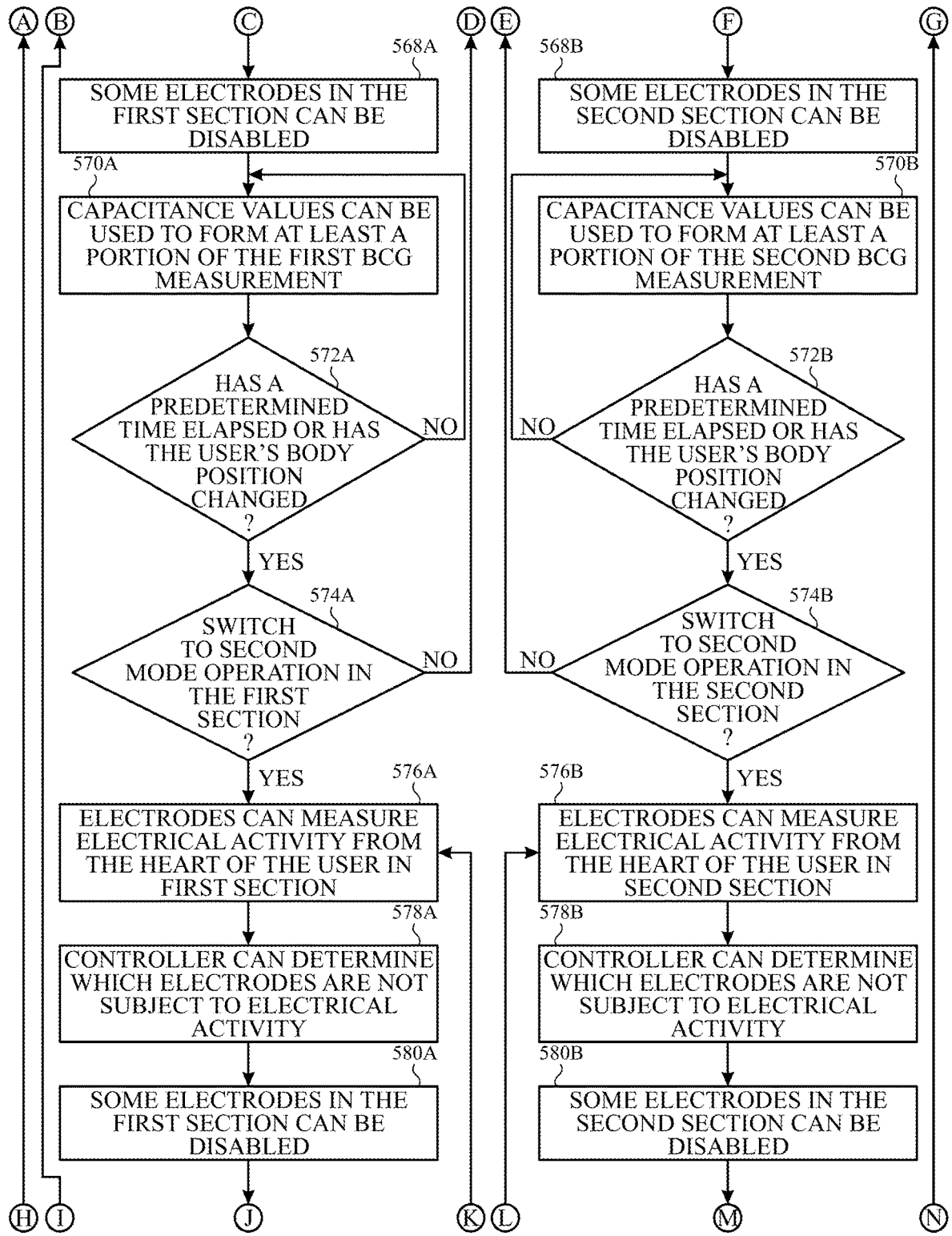
Figures 3, 5B:
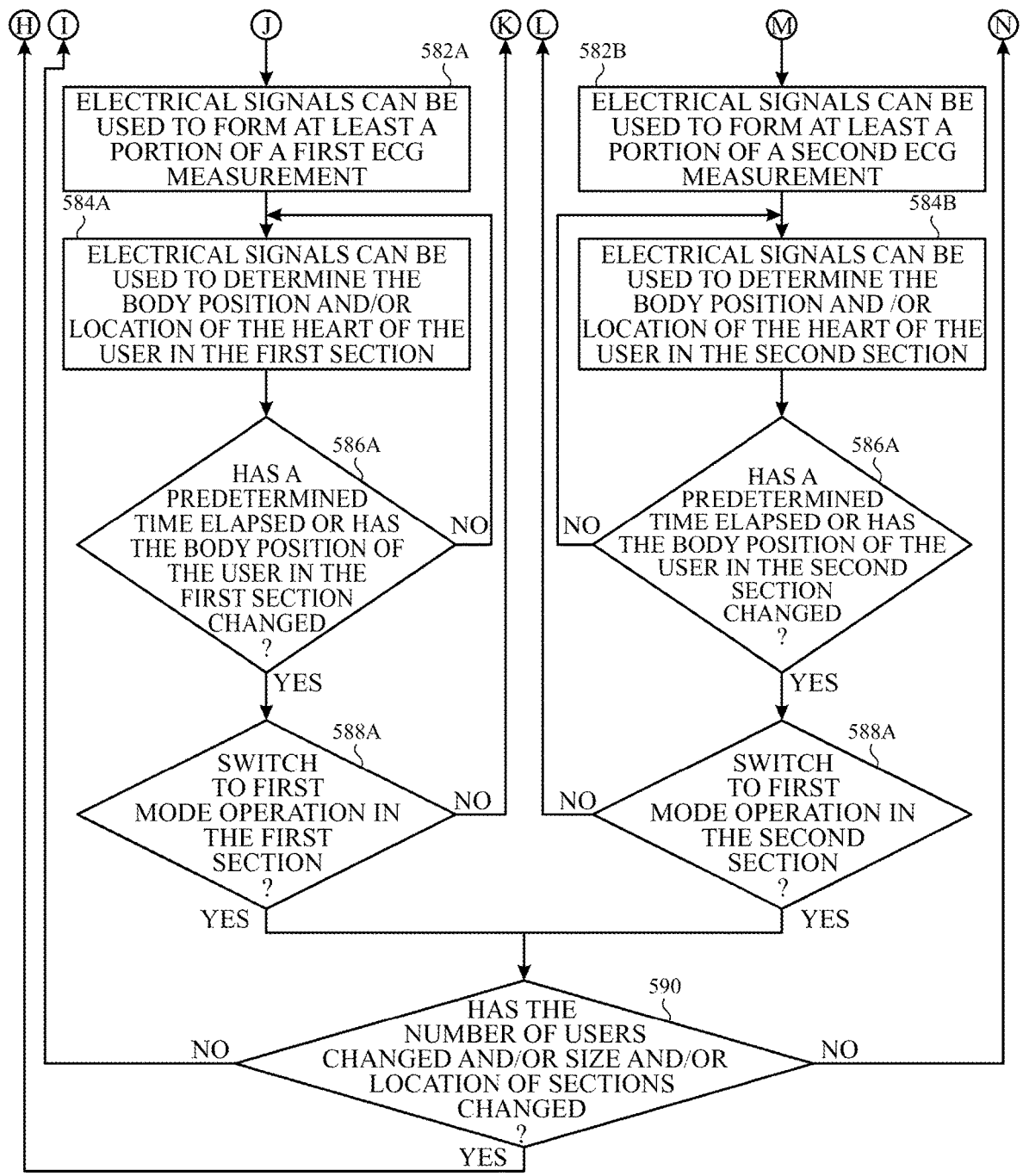

FIGS. 5B-1 to 5B-3 illustrate an exemplary process flow for dynamically partitioning the mat into multiple sections according to examples of the disclosure. Drive circuitry can stimulate one or more drive electrodes creating a mutual capacitance with one or more sense electrodes (step 552 of process 550). In some examples, all of the drive electrodes can be stimulated to allow the monitoring system to partition the entire mat. Sense circuitry can be coupled to one or more sense electrodes. Sense circuitry can measure any changes in capacitance caused by the user's force causing changes in the distances between the drive and sense electrodes (step 554 of process 550). Controller can form an image of the user's body position and/or location on the mat (step 555 of process 550). Based on the image, the system can determine that there are multiple users located on the mat, and the controller can partition the mat into multiple sections (step 556 of process 550). In some examples, one or more switching matrices can couple (or decouple) two or more electrodes to decrease (or increase) the granularity (step 558 of process 550). For example, increased granularity for discerning the boundaries of the body position and/or locations of the multiple users may not be needed, for example, when the users are spatially separated far apart (e.g., more than one electrode not subjected to either user's body can be located between users).

In some examples, the measurements of each section can be taken independently. Each section can operate in multiple modes: one mode (i.e., first mode) for measuring capacitance values and another mode (i.e., second mode) for measuring electrical signals. In some examples, the mode of operation of a given section can be independent from the other section(s).

During a first mode for a first section (e.g., section 501 illustrated in FIG. 5A), drive circuitry can stimulate one or more drive electrodes (e.g., electrodes 536 and electrodes 538 illustrated in FIG. 5A) in the first section to create a mutual capacitance with one or more sense electrodes in the first section (step 560A of process 550). Sense circuitry can be coupled to one or more sense electrodes in the first section. Sense circuitry can measure any changes in capacitance caused by the force of the user (e.g., user 598) that can change the distance between the drive and sense electrodes associated with the first section (step 562A of process 550). A controller or processor coupled to sense circuitry can form an image of the user's body position and/or location in the first section (step 564A of process 550). The controller or processor can determine which drive and sense electrodes are not affected by the user's force in the first section (step 566A of process 550) and can disable or disconnect the drive and/or sense electrodes (e.g., electrodes 536 illustrated in FIG. 5A) in the first section to conserve power, for example (step 568A of process 550). The measured capacitance values can be used to form at a least a portion of a first BCG measurement associated with the first section (step 570A of process 550). Operation of the first section in the first mode can be repeated after a predetermined time interval and/or when the user's body position and/or location in the first section changes (step 572A of process 550). In some examples, operation of the first section in the first mode can be repeated after operation of the first section in the second mode has been completed (step 574A of process 550). In some examples, operation of the first section in the first mode can depend on operation of the second section.

During operation of the first section (e.g., section 501 illustrated in FIG. 5A) in the second mode, one or more electrodes (e.g., electrode 538 illustrated in FIG. 5A) can be configured to measure electrical impulses from the heart of the user (e.g., user 598) located in the first section (step 576A of process 550). In some examples, the difference in electrical potentials between multiple electrodes can be measured. The controller or processor can determine which electrodes in the first section are not affected by the electrical signals of the user's heart (step 578A of process 550) and can disable or disconnect the electrodes to conserve power, for example (step 580A of process 550). The measured electrical signals can be used to form at least a portion of a first ECG measurement (step 582A of process 550). In some examples, the electrical signals can be used to determine the user's body position, the user's body location, the location of the user's heart, or a combination thereof (step 584A of process 550). In some examples, step 564A (and/or step 552 and step 554) can be used to form a rough estimate or coarse image of the user's body position and/or location, and step 584A can be used to form a more detailed or finer image of the user's body position and/or location. Operation of the first section in the second mode can be repeated after a predetermined time interval and/or when the body position and/or location of the user in the first section change (step 586A of process 550). In some examples, operation of the first section in the second mode can be repeated after operation of the first section in the first mode has been completed (step 588A of process 550). In some examples, operation of the first section in the second mode can depend on operation of the second section.

At the same time or at a time different from operating the first section, the second section (e.g., section 503 illustrated in FIG. 5A) can operate in the first mode. Drive circuitry can stimulate one or more drive electrodes (e.g., electrodes 532 and electrode 534 illustrated in FIG. 5A) in the second section to create a mutual capacitance with one or more sense electrodes in the second section (step 560B of process 550). Sense circuitry can be coupled to one or more sense electrodes in the second section. Sense circuitry can measure any changes in capacitance caused by the force of the user (e.g., user 596) that can change the distance between the drive and sense electrodes associated with the second section (step 562B of process 550). A controller or processor coupled to sense circuitry can form an image of the user's position in the second section (step 564B of process 550). The controller or processor can determine which drive and sense electrodes are not affected by the user's force in the second section creating separations between drive and sense electrodes (step 566B of process 550) and can disable or disconnect the drive and/or sense electrodes (e.g., electrodes 532 illustrated in FIG. 5A) in the second section to conserve power, for example (step 568B of process 550). The measured capacitance values can be used to form at a least a portion of a second BCG measurement associated with the second section (step 570B of process 550). Operation of the second section in the first mode can be repeated after a predetermined time interval and/or when the user's body position and/or location in the second section changes (step 572B of process 550). In some examples, operation of the second section in the first mode can be repeated after operation of the second section in the second mode has been completed (step 574B of process 550). In some examples, operation of the second section in the first mode can depend on operation of the second section.

During operation of the second section (e.g., section 503 illustrated in FIG. 5A) in the second mode, one or more electrodes (e.g., electrode 534 illustrated in FIG. 5A) can be configured to measure electrical impulses from the heart of the user (e.g., user 596) located in the second section (step 576B of process 550). In some examples, the differences in electrical potential between multiple electrodes can be measured. The controller or processor can determine which electrodes in the second section are not affected by the electrical signals of the user's heart (step 578B of process 550) and can disable or disconnect the electrodes to conserve power, for example (step 580B of process 550). The measured electrical signals can be used to form at a least a portion of a second ECG measurement (step 582B of process 550). In some examples, the electrical signals can be used to determine the user's body position, the user's body location, the location of the user's heart, or a combination thereof (step 584B of process 550). In some examples, step 564B (and/or step 552 and step 554) can be used to form a rough estimate or coarse image of the user's body position and/or location, and step 584B can be used to form a more detailed or finer image of the user's body position and/or location. Operation of the second section in the second mode can be repeated after a predetermined time interval and/or when the body position and/or location of the user in the second section changes (step 586B of process 550). In some examples, operation of the second section in the second mode can be repeated after operation of the second section in the first mode has been completed (step 588B of process 550). In some examples, operation of the second section in the second mode can depend on operation of the first section.

If any one of the number of users, the size of one or more sections, and the locations of one or more sections changes (step 590 of process 550), the system can return to selecting the number of sections and partitioning the system into the selected number of sections. Although FIG. 5B illustrates step 590 as after step 588A and step 588B, examples of the disclosure can include selecting the number of sections and partitioning the system into the selected number of sections at any step in the process.

At any time, the controller can utilize other (e.g., predetermined) information to discern between users and to form the sections. For example, if two users are contacting each other or in close proximity to each other, the controller may not be able to discern whether one or more electrodes are measuring one user, the other user, or both. The controller can associate the measurement information (e.g., stored in a database or in memory) to characteristics of the human anatomy. For example, if the overall measurement image does not match the outline of one user, the controller may determine that more than one user can be utilizing the system. The controller may attempt to match the measurement image to differing combinations of user positions and/or may use other measured information (e.g., location of a user's heart based on the intensity of the electrical signals) to discern between the multiple users.

Figure 5C:
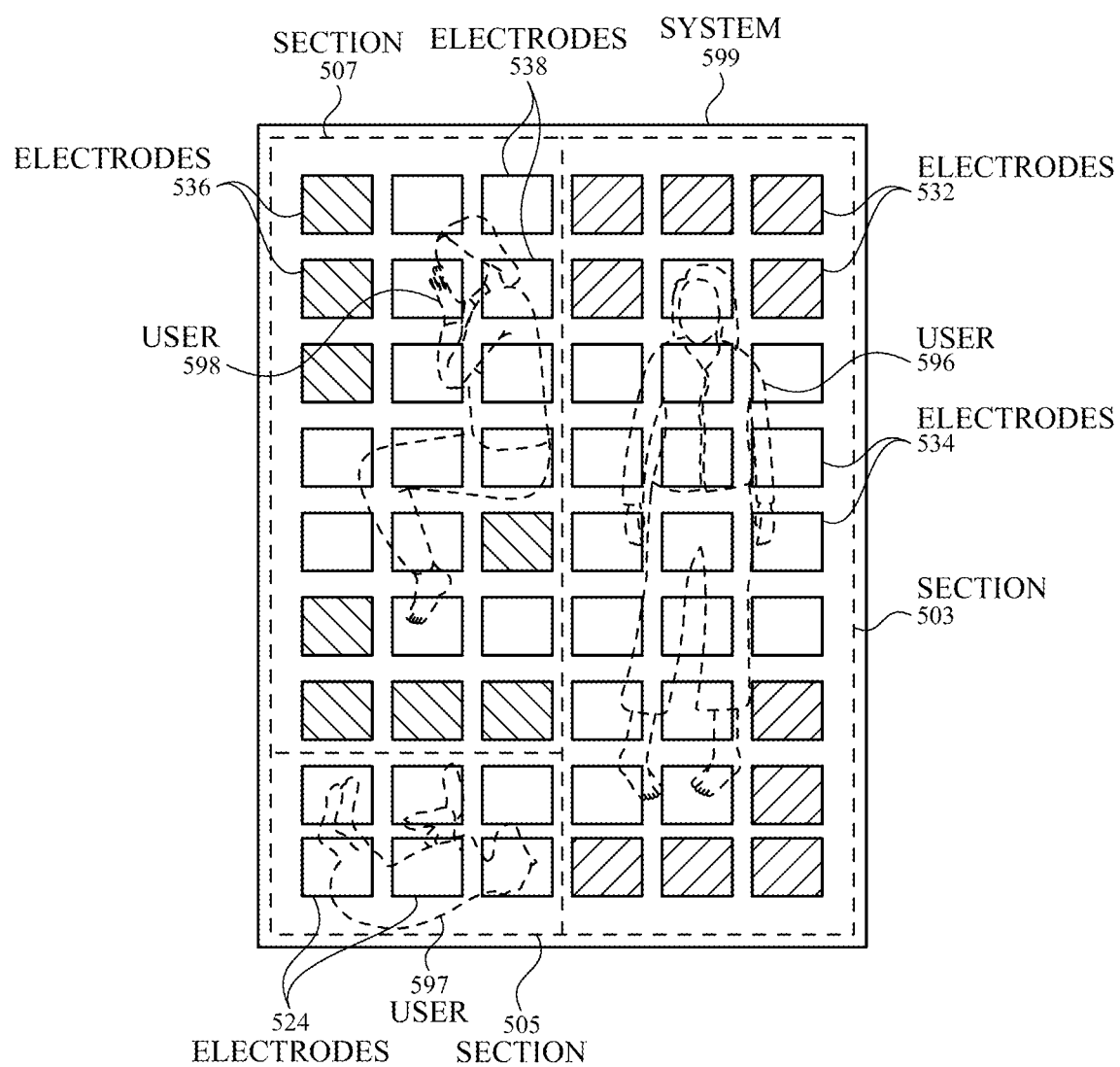
FIG. 5C illustrates a top view of an exemplary monitoring system including multiple sections according to examples of the disclosure.

Although FIG. 5A illustrates the monitoring system being partitioned into two sections, examples of the disclosure can include any number of sections including, but not limited to, one or greater than two sections. In some examples, the monitoring system can be capable of further partitioning selected sections. FIG. 5C illustrates a top view of an exemplary monitoring system including multiple sections according to examples of the disclosure. Multiple users, such as user 596, user 597, and user 598, can be located on system 599. System 599 can be capable of detecting the body position and/or locations of the multiple users and can be capable of partitioning the system into a plurality of sections, such as section 503, section 505, and section 507. In some examples, system 599 can select less than all of the sections to further partition into multiple sections, where the partitioning can be dynamic. For example, user 596 and user 598 can be located on system 599. System 599 can detect the presence of multiple users and can dynamically partition into two sections (e.g., section comprising the left side of system 599 and section 503). User 598 located in the left section can change body position and/or location. For example, user 598 can move closer to the upper edge of system 599 to make room for user 597, as shown in FIG. 5C. System 599 can detect the change in body position and/or location of user 598 and can dynamically partition left section into multiple sections, such as section 505 and section 507. In some examples, dynamically partitioning a section can include measuring the capacitance values and/or electrical signals using any or all of the techniques previously discussed. In some examples, while dynamically partitioning the left section into multiple sections, the size, shape, and/or location of section 503 can be maintained. In some examples, maintaining section 503 can include omitting capacitance and/or electrical measurements to determine the size, shape, and/or location of section 503 and/or the body position and/or location of user 599. In some examples, one or more sections can be inactivated if, for example, analysis of the user (e.g., user 597) is not desired.

Figure 6A:
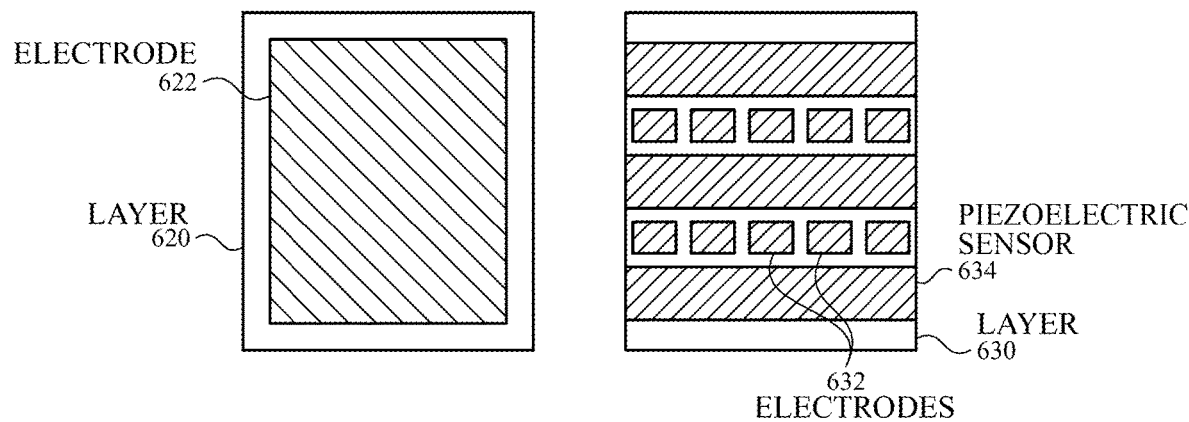
FIGS. 6A-6B illustrate top and perspective views of layers included in an exemplary mat according to examples of the disclosure.
Figure 6B:
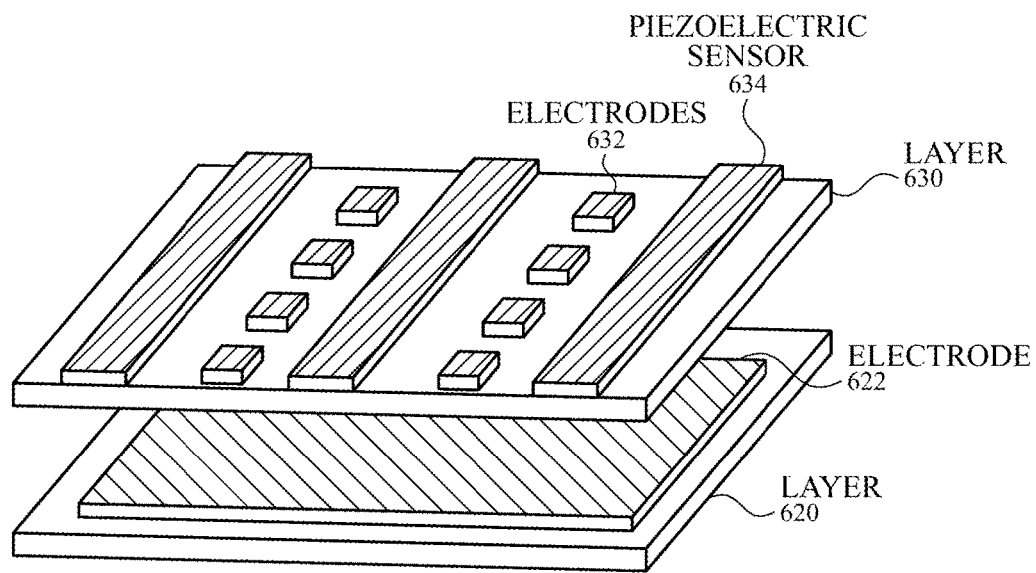

FIGS. 6A-6B illustrate top and perspective views of layers included in an exemplary mat according to examples of the disclosure. The exemplary mat can include layer 620 and layer 630. The design and/or operation of layer 630, plurality of electrodes 632, and electrode 622 can include the design and/or operation of layer 230, plurality of electrodes 232, and electrode 222, respectively, as discussed above. In some examples, the exemplary mat can include an additional layer (not shown) configured to provide support or electrical insulation from one or more materials or layers (e.g., the mattress). In some examples, the additional layer can include one or more electrodes (not shown).

Layer 630 can further include one or more piezoelectric sensors 634. Piezoelectric sensors 634 can include a sensor capable of generating one or more electrical signals in response to one or more changes in material properties (e.g., pressure or force). Examples of the disclosure can include piezoresistive sensors. The user's heartbeat can create mechanical impulses, which can change the properties of piezoelectric sensors 634. The piezoelectric measurement can form at least a portion of a BCG measurement. In some examples, piezoelectric sensors 634 can be located in areas of mat with greater strain than other areas. System 699 can include any number, size, and/or shape of piezoelectric sensors 634. In some examples, piezoelectric sensors 634 can include sections of rigid material physically connected together by flexible material. The rigidity of a piezoelectric sensor and the material between piezoelectric sensors can be adjusted. In some examples, piezoelectric sensors 634 can be interleaved with one or more rows of plurality of electrodes 632. In some examples, some of piezoelectric sensors 634 can be activated, and some of the piezoelectric sensors 634 can be deactivated at any given time based on the location of the user. For example, activated piezoelectric sensors can be located directly under (or in the immediate periphery of) the user, whereas deactivated piezoelectric sensors can be located elsewhere.

Figure 6C:
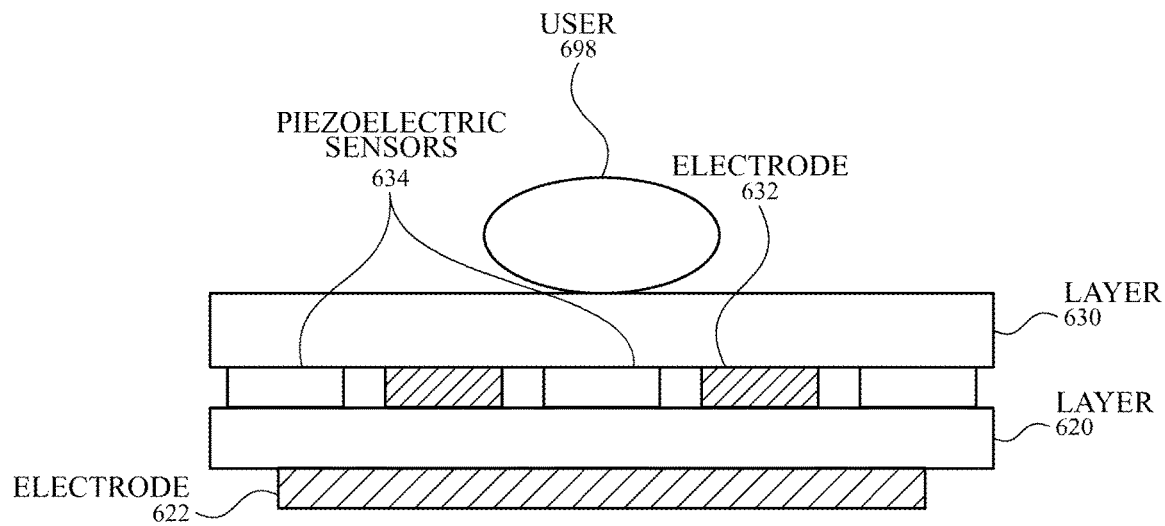
FIGS. 6C-6D illustrate cross-sectional views of an exemplary mat according to examples of the disclosure.
Figure 6D:
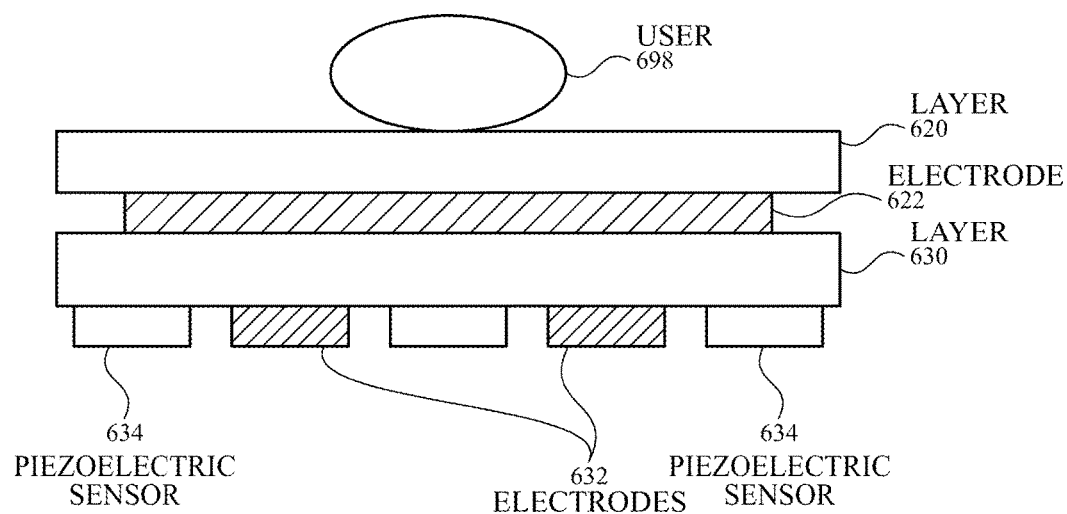

FIGS. 6C-6D illustrate cross-sectional views of an exemplary mat according to examples of the disclosure. The exemplary mat can be configured with any number of layers and/or arrangement of layers relative to the other layers. For example, as illustrated in FIG. 6C, layer 620 can be located on one side of layer 630, and user 698 can be located on the other side of layer 630. Plurality of electrodes 632 and plurality of piezoelectric sensors 634 can be located between layer 620 and layer 630. Electrode 622 can be located on the opposite side of layer 620 than plurality of electrodes 632. In some examples, as illustrated in FIG. 6D, layer 630 can be located on one side of layer 620, and user 698 can be located on the other side of layer 620. Electrode 622 can be located between layer 620 and layer 630. Plurality of electrodes 632 and plurality of piezoelectric sensors 634 can be located on the opposite side of layer 630 than electrode 622.

Electrode 622, plurality of electrodes 632, and plurality of piezoelectric sensors 634 can be configured with one or more functionalities. The design and/or operation of layer 630, plurality of electrodes 632, and electrode 622 can include the design and/or operation of layer 230, plurality of electrodes 232, and electrode 222, respectively, as discussed above. In some examples, plurality of electrodes 632 can be configured as multifunctional sensors capable of measuring capacitance during one mode and measuring electrical signals during another mode. In some examples, some of the plurality of electrodes 632 can be configured to measure capacitance and others of the plurality of electrodes 632 can be configured to measure electrical signals. In some examples, the monitoring system can include one or more switching matrices (not shown) configured to couple or decouple together sections of electrode 622 (not shown), two or more of the plurality of electrodes 632, and/or two or more piezoelectric sensors 634.

Figures 1, 6E:
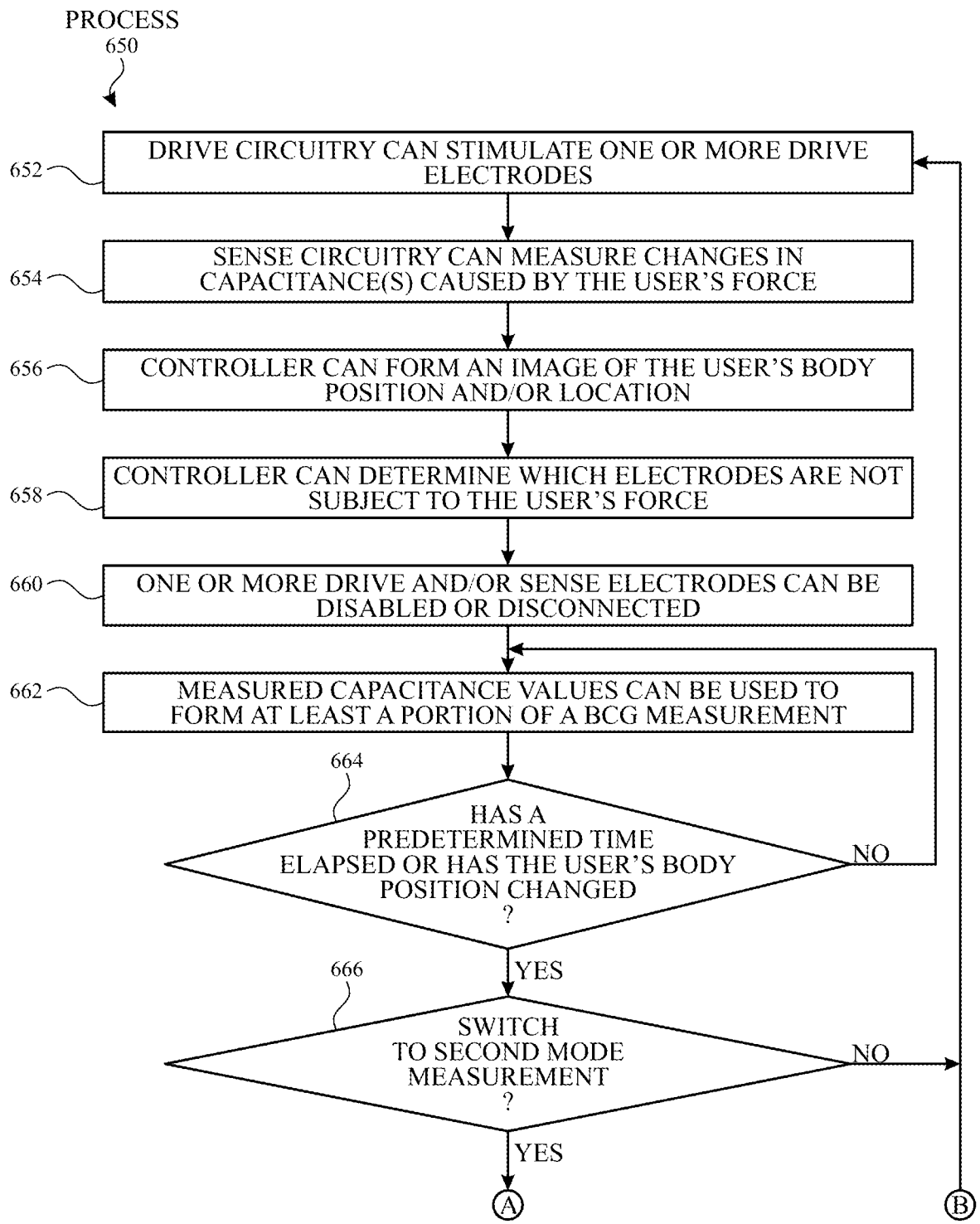
Figures 2, 6E:
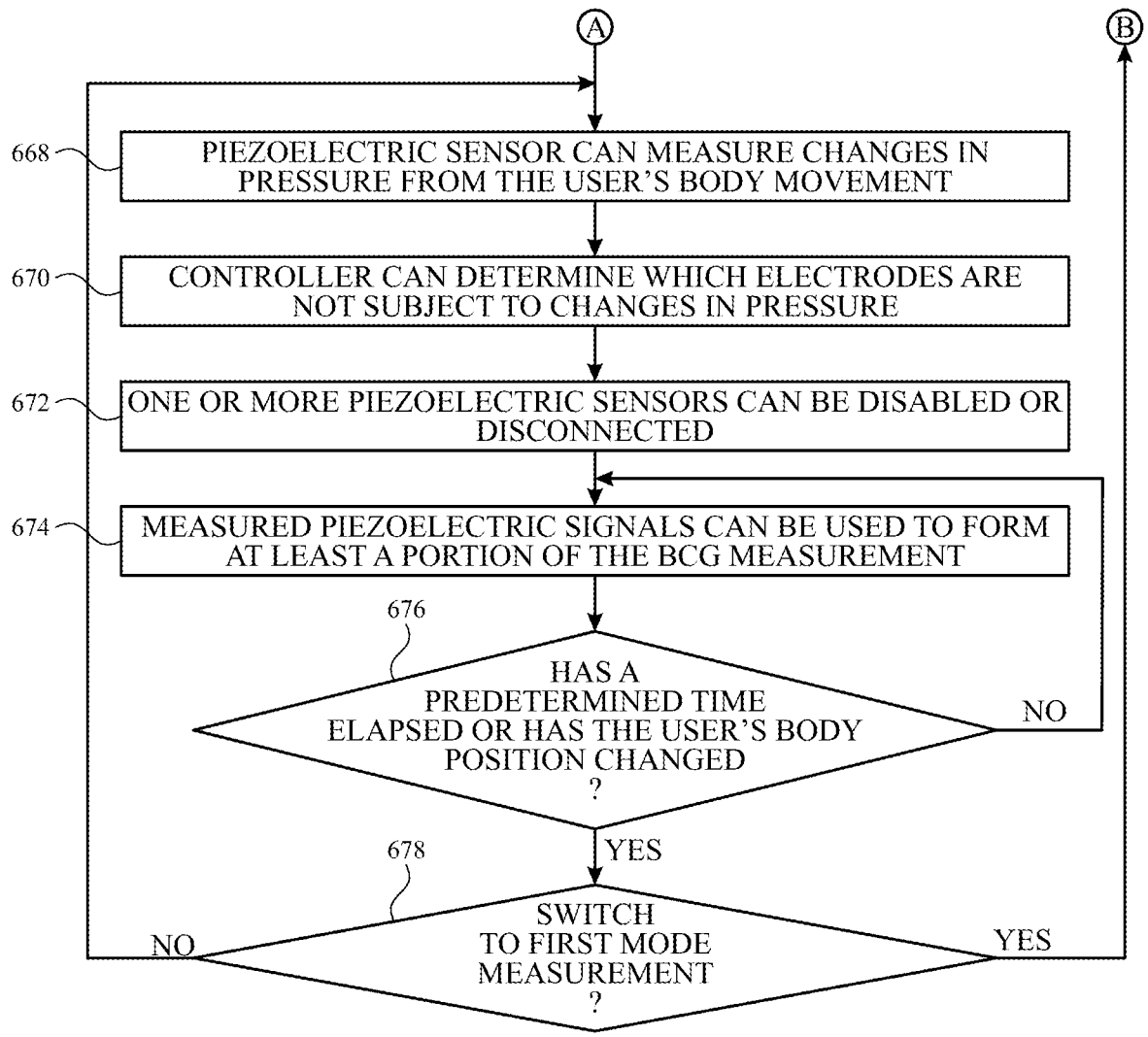

In some examples, the monitoring system can operate in multiple modes: a first mode for measuring capacitance, a second mode for measuring electrical signals, and a third mode for measuring changes in pressure. FIGS. 6E-1 and 6E-2 illustrate an exemplary process flow for capacitive, electrical, and piezoelectric measurements according to examples of the disclosure. During the first mode, drive circuitry can stimulate one or more drive electrodes creating a mutual capacitance with one or more sense electrodes (step 652 of process 650). Sense circuitry can be coupled to one or more sense electrodes. Sense circuitry can measure any changes in capacitance caused by the user's force that can change the distance between the drive and sense electrodes (step 654 of process 650). A controller or processor coupled to sense circuitry can form an image of the user's body position and/or location on the mat (step 656 of process 650). The controller or processor can determine which drive and/or sense electrodes are not affected by the user's force or body weight (step 658 of process 650) and can disable or disconnect the drive and/or sense electrodes to conserve power, for example (step 660 of process 650). The measured capacitance values can be used to form at least a portion of a BCG measurement (step 662 of process 650). The first mode can be repeated after a predetermined time interval and/or when the user's body position and/or location change (step 664 of process 650). In some examples, the first mode can be repeated after the second mode has been completed (step 666 of process 650).

During the second mode, one or more piezoelectric sensors can be configured to measure the changes in pressure on the sensors from the user's body movement (step 668 of process 650). The controller or processor can determine which piezoelectric sensors are not affected by change in pressure due to the user's body movement (step 670 of process 650) and can disable or disconnect the piezoelectric sensors to conserve power, for example (step 672 of process 650). In some examples, the controller or processor can compare the strain of all or some of the piezoelectric sensors; can enable the piezoelectric sensors located in areas of the mat with greater strain than in other areas; and can disable the piezoelectric sensors located in the other areas. The measured piezoelectric signals can be used to form at a least portion of the BCG measurement (step 674 of process 650).

In some examples, the electrodes and piezoelectric sensors can be configured to measure the same type of information, but at different levels of granularity. For example, BCG information can be used to determine the user's body movement. Mutual capacitance measurements (i.e., step 654) can be used to form a rough estimate or coarse determination of the user's body movement, and the piezoelectric measurements (i.e., step 658) can be used for a more accurate determination of the user's body movement. Although a user's breathing can cause a motion artifact, the breathing motion can different from gross motion due to the user moving or stirring. Being able to discriminate gross motion from breathing can lead to a more accurate analysis. In some examples, the mutual capacitance measurements can be used to measure displacement of the user's body, while the piezoelectric measurements can be used to measure the velocity of the user's body.

The third mode can be repeated after a predetermined time interval and/or when the user's body position and/or location change (step 676 of process 650). In some examples, the second mode can be repeated after the first mode has been completed (step 678 of process 650). Although FIG. 6E illustrates the controller beginning with the first mode measurement, examples of the disclosure can include beginning with the second mode measurement or beginning with both the first and second mode measurements. Although FIG. 6E illustrates the controller performing the first and second mode measurements sequentially, examples of the disclosure can include performing the first and second mode measurements concurrently.

Figure 7A:
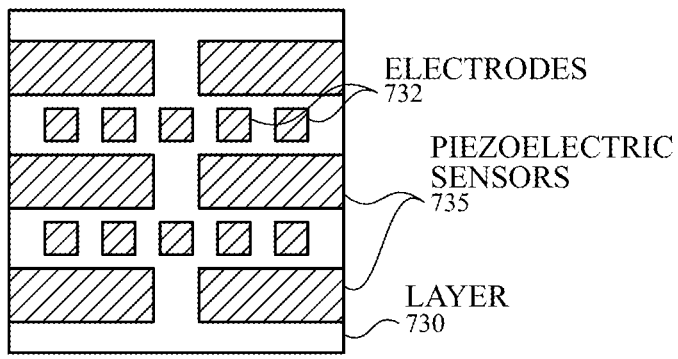
FIGS. 7A-7B illustrate top views of exemplary layers included in a mat according to examples of the disclosure.
Figure 7B:
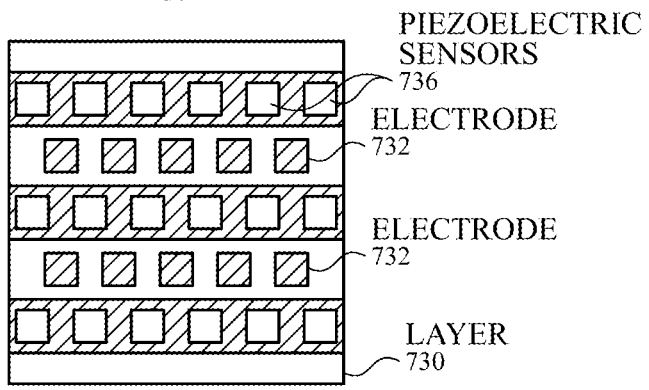

In some examples, monitoring system can include a plurality of piezoelectric sensors. FIGS. 7A-7B illustrate top views of exemplary layers included in a mat according to examples of the disclosure. Piezoelectric sensors can include any size, size, and/or resolution. For example, piezoelectric sensors 735 can be rectangular and/or have a length greater than electrodes 732, as illustrated in FIG. 7A. Layer 730 can be configured such that piezoelectric sensor 735 on one side can be configured for one user, and piezoelectric sensor 735 on the other side can be configured for another user. In some examples, the piezoelectric sensors 735 can be electrically isolated from each other allowing independent measurements to be taken for different users. In some examples, some of piezoelectric sensors 735 can be enabled, and some of piezoelectric sensors 735 can be disabled. When the user moves in a direction perpendicular to the long axis of the piezoelectric sensors 735, the enabled and disabled piezoelectric sensors 735 can change. In some examples, piezoelectric sensors 735 enabled on one side of the mat can be longitudinally displaced from the piezoelectric sensors 735 enabled on the other side. Layer 730 can further include a plurality of electrodes 732.

In some examples, piezoelectric sensors 736 can have the same size as electrodes 732, as illustrated in FIG. 7B. Layer 730 can include a plurality of electrodes 732 and a plurality of piezoelectric sensors 736. Given the smaller size and greater number of piezoelectric sensors (e.g., compared to the mat illustrated in FIG. 7A), the resolution of the piezoelectric measurement can be greater. In some examples, each piezoelectric sensor 736 can include sections of rigid material that can be physically connected to by flexible material. The rigidity of a piezoelectric sensor and the material between piezoelectric sensors can be adjusted. Plurality of piezoelectric sensors 736 can be located in any arrangement including, but not limited to, one or more rows of piezoelectric sensors 736 running across the mat or a matrix of rows and columns of piezoelectric sensors. In some examples, each of the piezoelectric sensors 736 can be electrically isolated and independently controlled from the other piezoelectric sensors 736. The monitoring system can be configured to form an image representative of the changes in pressure across the mat.

Figure 7C:
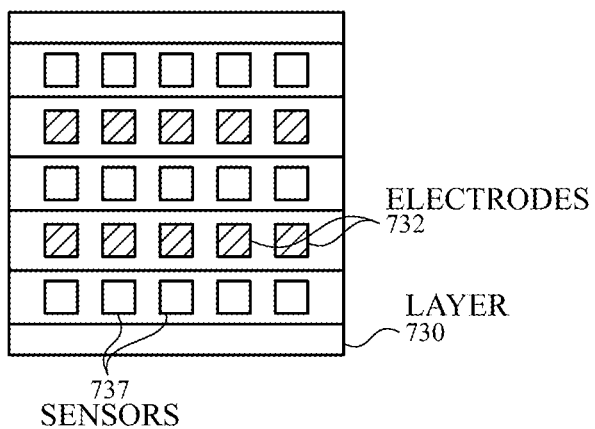
FIGS. 7C-7D illustrate top and cross-sectional views of an exemplary mat including electrodes disposed on piezoelectric sensors according to examples of the disclosure.
Figure 7D:
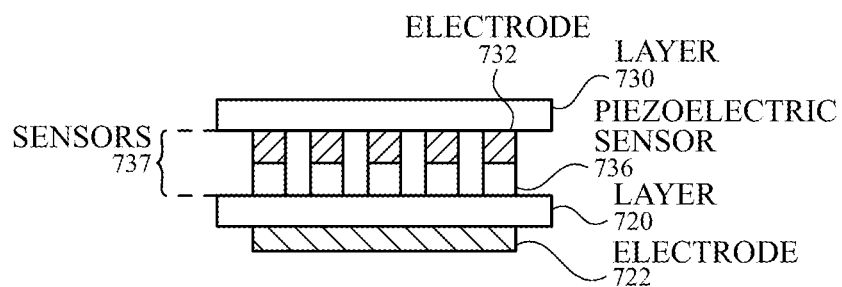

In some examples, one or more electrodes can be disposed on one or more piezoelectric sensors. FIGS. 7C-7D illustrate top and cross-sectional views of an exemplary mat including electrodes disposed on piezoelectric sensors according to examples of the disclosure. The exemplary mat can include layer 720 and layer 730. Layer 720 can include electrode 722. Layer 730 can include a plurality of sensors 737. Plurality of sensors 737 can include one or more electrodes 732 and one or more piezoelectric sensors 736. Sensors 737 can be capable of measuring capacitance values between electrode 722 and electrode 733, measuring changes in pressure from piezoelectric sensor 736, and/or measuring electrical signals from electrode 722 and/or electrode 732. The mat can be configured with every other row including sensors 737 (i.e., electrodes 732 disposed on piezoelectric sensors 736) and the other rows including only electrodes 732, as illustrated in FIG. 7C.

Figure 7E:
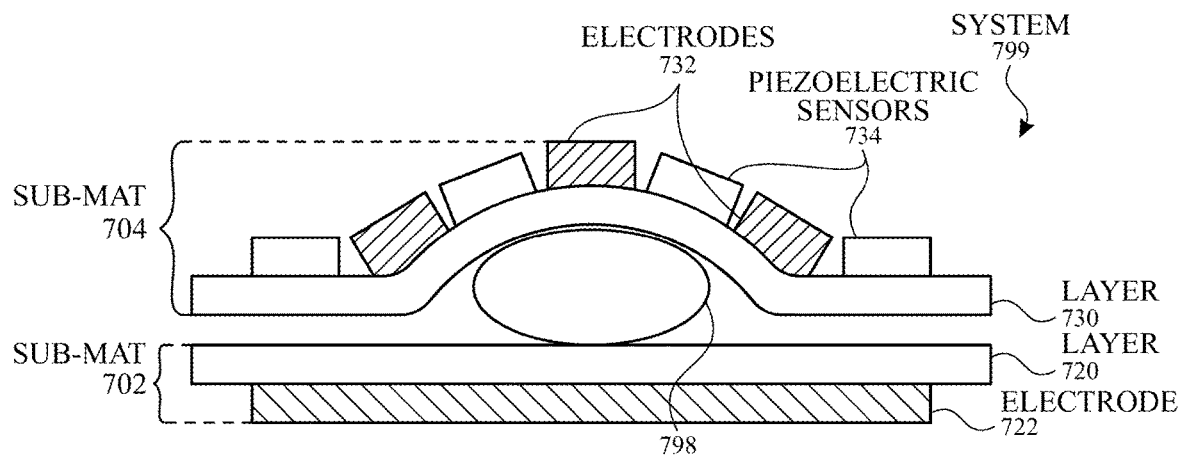
FIGS. 7E-7G illustrate cross-sectional views of exemplary mats according to examples of the disclosure.
Figure 7F:
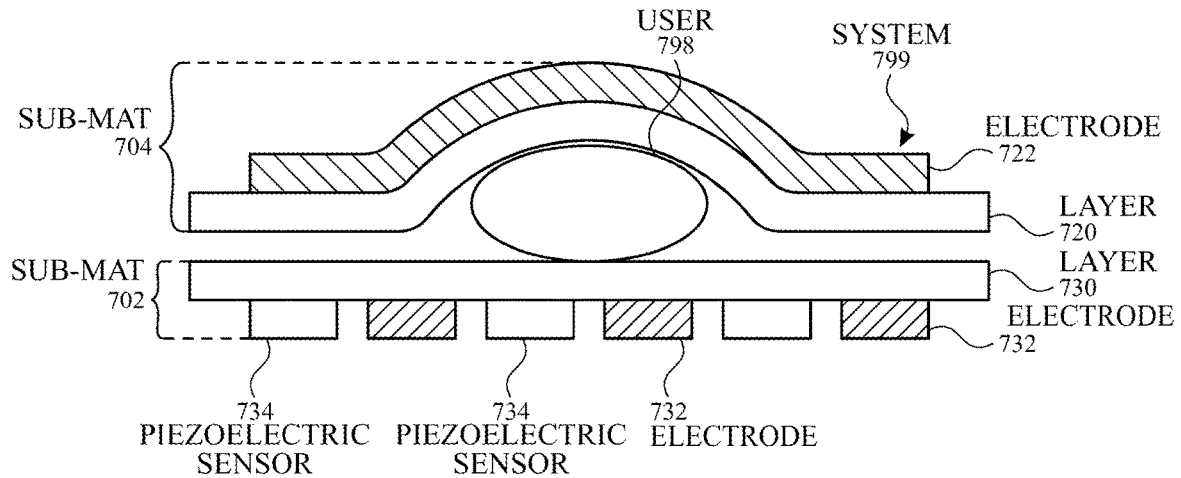
Figure 7G:
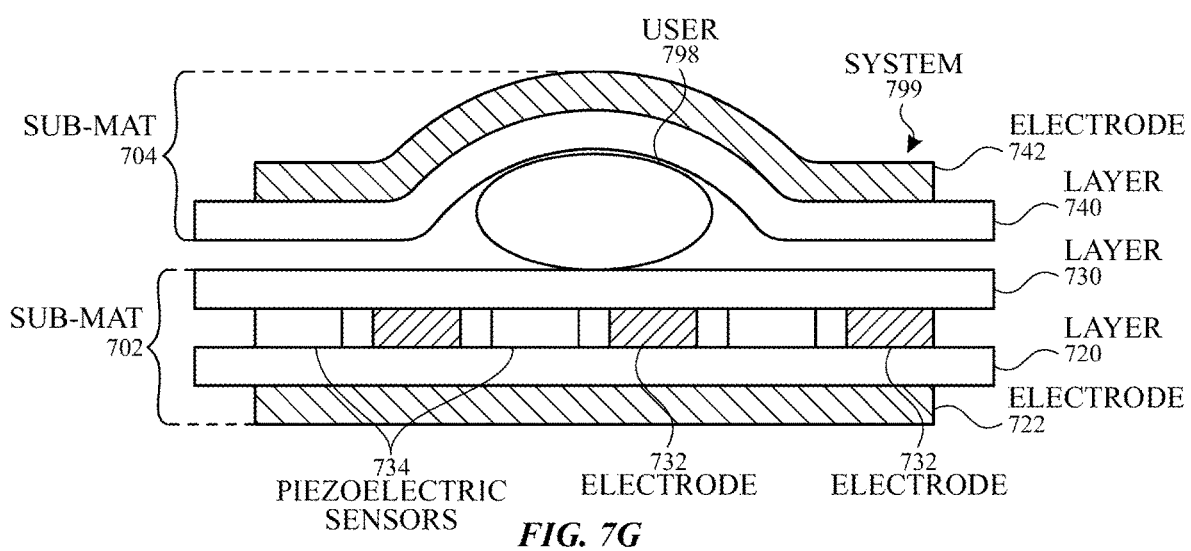

FIGS. 7E-7G illustrate cross-sectional views of exemplary mats according to examples of the disclosure. In some examples, as illustrated in FIG. 7E, system 799 can include sub-mat 702 and sub-mat 704 with user 798 located between sub-mat 702 and sub-mat 704. Sub-mat 702 can include layer 720 and electrode 722. In some examples, electrode 722 can be deposited on a substantial (e.g., 75%) area of layer 720. Electrode 722 can be continuous (i.e., a discrete piece of material). Sub-mat 704 can include layer 730, a plurality of electrodes 732, and a plurality of piezoelectric sensors 734. Electrode 722, plurality of electrodes 732, or both can include any conductive material including, but not limited to, silver, copper, gold, aluminum, steel, brass, bronze, and graphite. In some examples, electrode 722 and plurality of electrodes 732 can include the same materials.

Electrode 722 and plurality of electrodes 732 can be configured with one or more functionalities. The design and/or operation of layer 730, plurality of electrodes 732, and electrode 722 can include the design and/or operation of layer 330, plurality of electrodes 332, and electrode 322, respectively, as discussed above. Additionally, the design and/or operation of piezoelectric sensors 734 and piezoelectric sensors 736 can include the design and/or operation of piezoelectric sensors 634, as discussed above.

In some examples, electrode 722 can include one or more sections of conductive material electrically coupled together for capacitance and/or BCG measurements. In some examples, electrode 722 can include a plurality of electrodes and can be further configured as sensing electrodes capable of sensing electrical signals for ECG measurements. In some examples, plurality of piezoelectric sensors 734 can be configured to measure changes in pressure/force caused by the mechanical impulses from the user's blood acceleration. In some examples, plurality of electrodes 732 can be configured as multifunctional sensors capable of measuring capacitance during one mode and measuring electrical signals during another mode. In some examples, some of the plurality of electrodes 732 can be configured to measure capacitance and others of the plurality of electrodes 732 can be configured to measure electrical signals. In some examples, system 799 can include one or more switching matrices (not shown) configured to couple or decouple together sections of electrode 722 (not shown), two or more of the plurality of electrodes 732, and/or two or more piezoelectric sensors 734.

In some examples, sub-mat 702 can include a switching matrix (not shown). The switching matrix can be configured to electrically couple one or more electrodes included in the plurality of electrodes 732 together and/or one or more piezoelectric sensors included in the plurality of piezoelectric sensors 734 together. The system can be capable of dynamically switching one or more electrodes utilized for the capacitance measurements. For example, in a first mode, user 798 can be located between sub-mat 702 and sub-mat 704. Electrode 722 can be configured as a sense electrode, and the plurality of electrodes 732 can be configured as drive electrodes. Changes in capacitance values can be due to the user's body parts increasing the separations between the sense and drive electrodes. In a second mode, sub-mat 704 can be removed from system 799 or located a certain distance away. The separation between sub-mat 704 from sub-mat 702 can prevent electrode 722 from capacitively coupling to plurality of electrodes 732, or the measured capacitance values can be below a predetermined threshold.

The switching matrix can electrically couple together the plurality of electrodes 732 and/or electrically couple together the plurality of piezoelectric sensors 734. The electrically coupled electrodes 732 can be configured as a drive electrode, and electrode 722 can be configured as a sense electrode. Changes in capacitance values can be due to the user's body weight applying a force that can change the distance between the sense and drive electrodes. When sub-mat 704 is returned back to system 799 and located a close enough distance such that electrode 722 can capacitively couple to the plurality of electrodes 732, system 799 can remain in the second mode or switch to the first mode.

Although FIG. 7E illustrates layer 730 located closer to user 798 than plurality of electrodes 732 and plurality of piezoelectric sensors 734 and layer 720 located closer to user 798 than electrode 722, examples of the disclosure can include plurality of electrodes 732 and plurality of piezoelectric sensors 734 located closer to user 798 than layer 730, electrode 722 located closer to user 398 than layer 720, or both. In some examples, sub-mat 702 and/or sub-mat 704 can include a layer (not shown) configured to provide support or electrical insulation from one or more materials or layers (e.g., the mattress), for example. In some examples, as illustrated in FIG. 7F, plurality of electrodes 732 and the plurality of piezoelectric sensors 734 can be included in sub-mat 702 along with layer 730. Additionally or alternatively, electrode 722 and layer 720 can be included in sub-mat 704.

In some examples, capacitance values can be measured between sub-mats, between a layer in the sub-mat, or both. FIG. 7G illustrates a cross-sectional view of an exemplary mat according to examples of the disclosure. In some examples, electrode 722 and electrode 742 can be configured as sense electrodes, and plurality of electrodes 732 can be configured as drive electrodes. System 799 can be configured such that stimulating some of the plurality of electrodes 732 can create a mutual capacitance with electrode 722, and stimulating others of the plurality of electrodes 732 can create a mutual capacitance with electrode 742. In this manner, the individual or combination of the measured capacitance values can be used to determine more information about the user's sleep. For example, the user 798 can be positioned with its back contacting sub-mat 702 and fingers contacting only sub-mat 704. Movement of the user's fingers may not be detected by electrodes located in sub-mat 702 due to the low change in pressure that can be associated with finger movements and the distance from the user's fingers and the electrodes located in sub-mat 702. However, fingers can be contacting or in close proximity to sub-mat 704, so one or more electrodes, such as electrode 742, included sub-mat 704 can be capable of detecting the user's finger movements. In some examples, electrodes included in sub-mat 702 can be configured to measure larger changes in body movements, and electrodes included in sub-mat 704 can be configured to measure smaller changes in body movements.

Figure 8A:
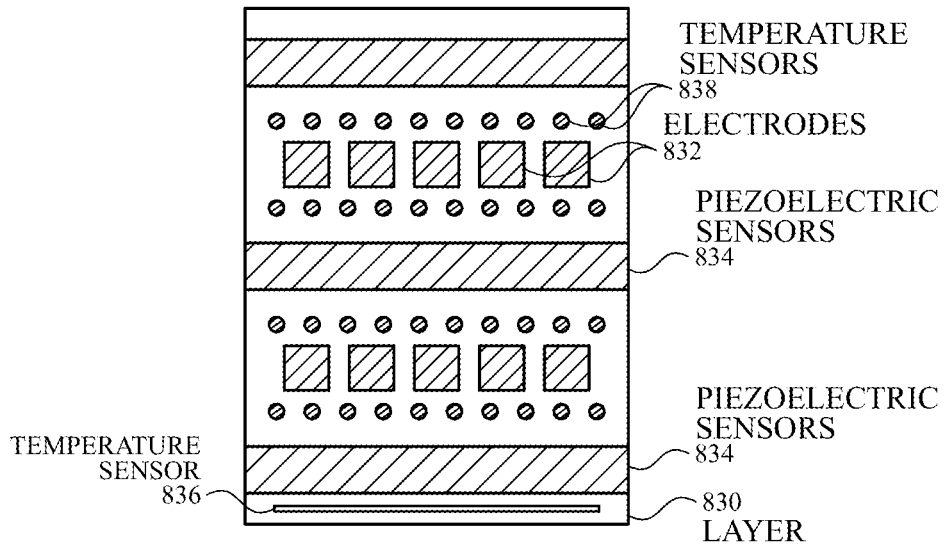
FIG. 8A illustrates a top view of an exemplary layer of a mat including a plurality of electrodes, a plurality of piezoelectric sensors, and a plurality of temperature sensors according to examples of the disclosure.

In some examples, the mat can include one or more temperature sensors. FIG. 8A illustrates a top view of an exemplary layer of a mat including a plurality of electrodes, a plurality of piezoelectric sensors, and a plurality of temperature sensors according to examples of the disclosure. Layer 830 can include a plurality of electrodes 832, a plurality of piezoelectric sensors 834, and a plurality of temperature sensors 838. Plurality of electrodes 832 can be configured for measuring capacitance values and/or electrical signals. The design and/or operation of plurality of electrodes 832 and plurality of piezoelectric sensors 834 can include the design and/or operation of plurality of electrodes 232 and plurality of piezoelectric sensors 634, respectively, as discussed above.

Plurality of temperature sensors 838 can be any type of sensor capable of measuring temperature including, but not limited to, a resistance thermometer, a thermistor, and a thermocouple. In some examples, one or more of the plurality of temperature sensors 838 can be located on the same layer as one or more of electrodes 832 and piezoelectric sensors 834. In some examples, the system can include one or more temperature sensors, such as temperature sensor 836, configured to measure the temperature of the room. In some examples, temperature sensors 836 can be in addition or instead of temperature sensors (e.g., temperature sensors 139 illustrated in FIG. 1) located in the control system (e.g., control system 140). Although FIG. 8A illustrates three different types of sensors (i.e., electrodes, piezoelectric sensors, and temperature sensors), examples of the disclosure can include some, but not all, of the different types of sensors.

Figure 8B:
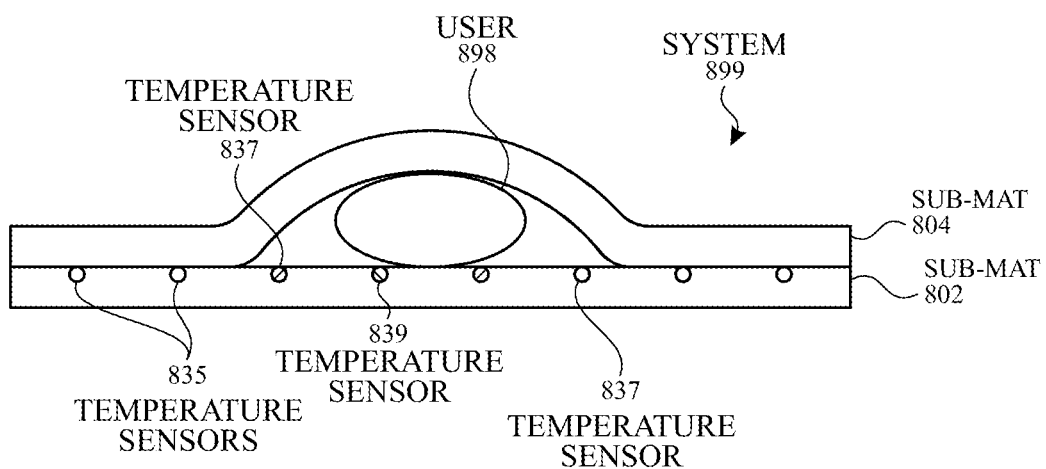
FIGS. 8B-8C illustrate cross-sectional and top views of the monitoring system including temperature sensors according to examples of the disclosure.
Figure 8C:
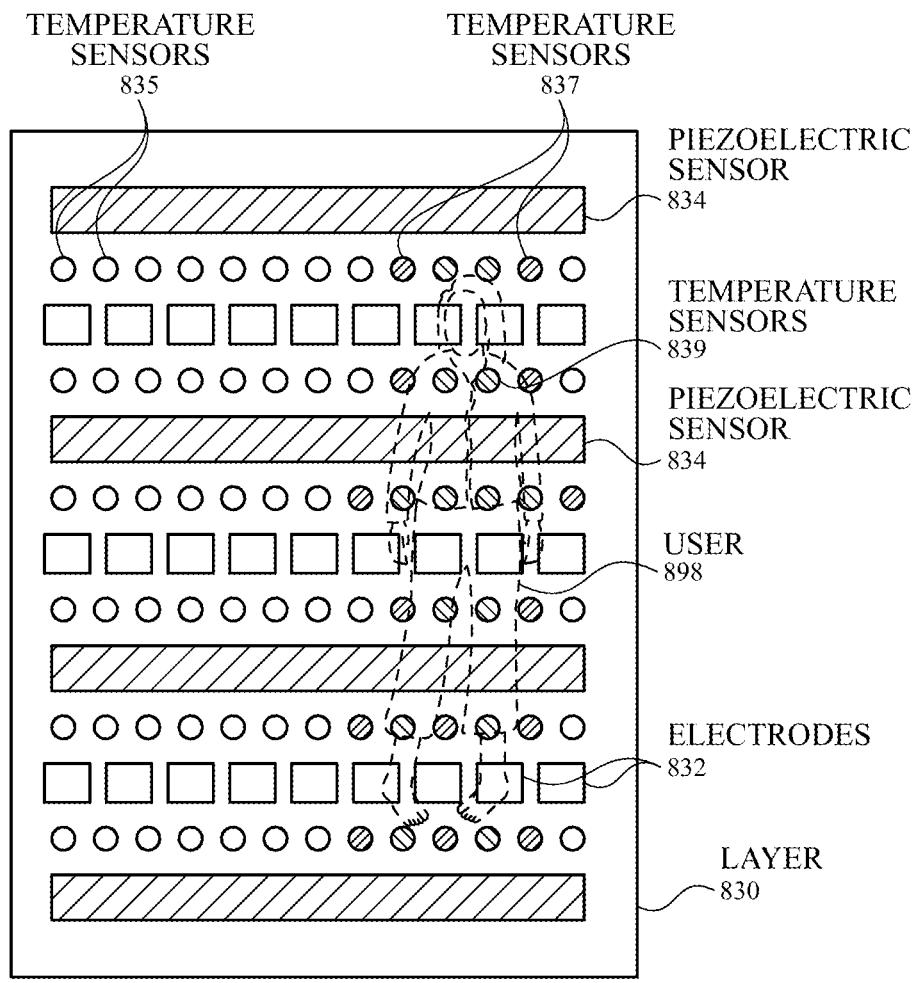

FIGS. 8B-8C illustrate cross-sectional and top views of the monitoring system including temperature sensors according to examples of the disclosure. The plurality of temperature sensors (e.g., plurality of temperature sensors 838 illustrated in FIG. 8A) can include multiple sets of temperatures sensors, such as plurality of temperature sensors 835, plurality of temperature sensors 837, and plurality of temperature sensors 839. In some examples, each set can include the same type of temperature sensor. In some examples, temperature measurements from each set can be utilized in a different manner (discussed below). In some examples, plurality of temperature sensors 835 can be located in areas outside of where user 898 can be located.

Plurality of temperature sensors 837 can be configured to measure the temperature of the local ambient (i.e., the space between the sub-mats 802). In some examples, plurality of temperature sensors 837 can be located in close proximity to, but not directly below user 898. In some examples, plurality of temperature sensors 837 can be located at or in close proximity to where sub-mat 804 contacts sub-mat 802 (as illustrated in FIG. 8B). Plurality of temperature sensors 839 can be configured to measure the temperature of user 898. By measuring the temperatures of both user 898 and the local ambient, the monitoring system can associate the temperatures in the sleep analysis of the user (discussed below).

In some examples, system 899 can be capable of determining the location of user 898 to disable or disconnect the temperature sensors (e.g., plurality of temperature sensors 835) not affected by the user's body temperature or not within close proximity to the user's body. In some examples, plurality of temperature sensors 839 can be located below user 898. In some examples, system 899 can be configured to dynamically change which temperature sensors are not associated with the user, which temperature sensors are associated with the temperature of user 898, and which temperature sensors are associated with the local ambient. Any of the temperature sensors (e.g., temperature sensors 935, temperature sensors 937, and temperature 939) can be coupled together using one or more switches.

Figure 8D:
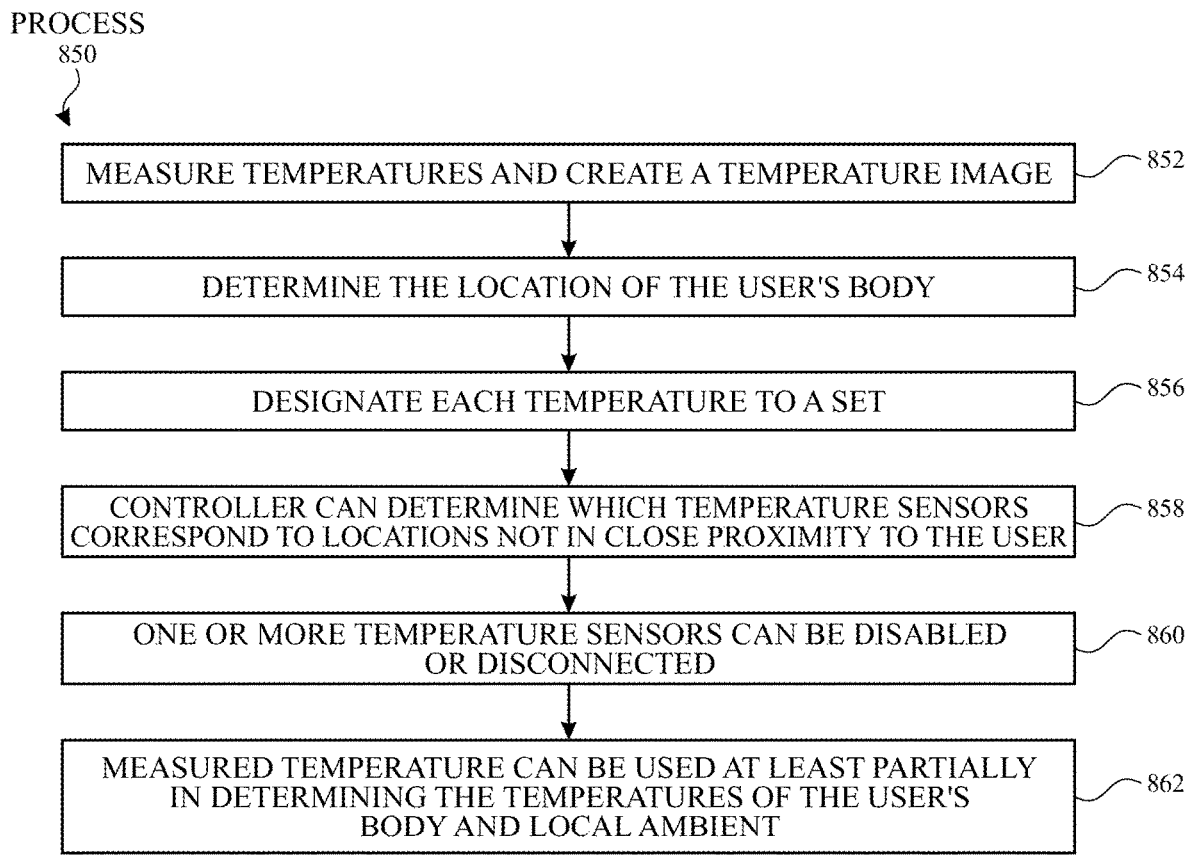
FIG. 8D illustrates an exemplary process flow for temperature measurements according to examples of the disclosure.

FIG. 8D illustrates an exemplary process flow for temperature measurements according to examples of the disclosure. In some examples, the monitoring system can measure temperatures across the mat and can create a temperature image (step 852 of process 850). The monitoring system can determine the location of the user's body (step 854 of process 850). In some examples, the monitoring system can utilize the temperature image to associate boundaries of the user's body to differences in temperature. In some examples, determining the location of the user's body can include any of the capacitance measurements, electrical measurements, piezoelectric measurements, or any combination thereof. For example, plurality of temperature sensors 835 and plurality of temperature sensors 837 can have different temperatures than plurality of temperature sensors 839 due to the differences in temperature between locations where the user is not located (measured by plurality of temperature sensors 835 and plurality of temperature sensors 837) and locations where the user is located (measured by the plurality of temperature sensors 839). Based on the different temperatures, the monitoring system can determine where the user's body is located. In some examples, plurality of temperature sensors 837 can have different temperatures than plurality of temperature sensors 835 due to the gap between sub-mat 802 and sub-mat 804 (as illustrated in FIG. 8B), and monitoring system can further uses these differences to determine the user's body location and/or to associate the temperature sensors in the sleep analysis of the user.

In some examples, the monitoring system can assign each temperature sensor to a certain set (step 856 of process 850), where each set can correspond to a type of area (e.g., locations not in close proximity to the user, locations in close proximity to the user, locations underneath the user) of the mat. A controller coupled to the temperature sensors can determine which temperature sensors correspond to locations not in close proximity to the user (step 858 of process 850) and can disable or disconnect those temperature sensors to conserve power, for example (step 860 of process 850). The measured temperatures can be used at least partially in determining the temperatures of the user's body and local ambient (step 862 of process 850). Examples of the disclosure can include measuring capacitance values, electrical signals, and/or piezoelectric signals at the same time or at different times than measuring the temperatures.

Figure 9:
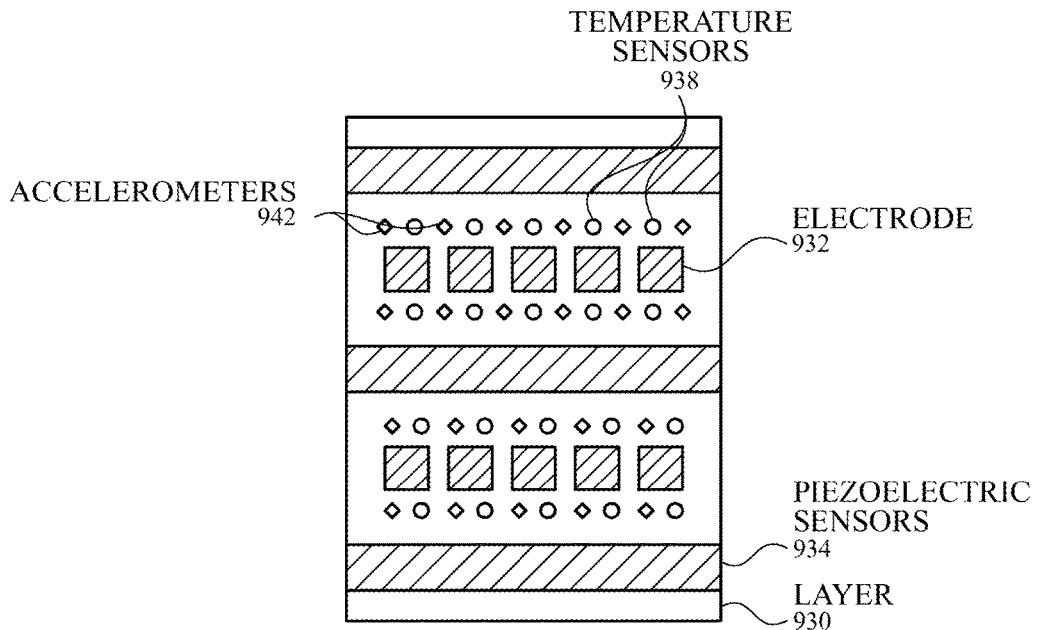
FIG. 9 illustrates a top view of an exemplary layer of a mat including a plurality of electrodes, a plurality of piezoelectric sensors, a plurality of temperature sensors, and a plurality of accelerometers according to examples of the disclosure.

In some examples, the mat can include one or more accelerometers. FIG. 9 illustrates a top view of an exemplary layer of a mat including a plurality of electrodes, a plurality of piezoelectric sensors, a plurality of temperature sensors, and a plurality of accelerometers according to examples of the disclosure. Layer 930 can include a plurality of electrodes 932, a plurality of piezoelectric sensors 934, a plurality of temperature sensors 938, and a plurality of accelerometers 942. The design and/or operation of plurality of electrodes 932 and plurality of piezoelectric sensors 934 can include the design and/or operation of plurality of electrodes 232 and plurality of piezoelectric sensors 634.

Plurality of accelerometers 942 can any type of device configured for measuring acceleration or vibrations. In some examples, the plurality of accelerometers can be configured to measure velocity of the user's body. In some examples, one or more of the plurality of accelerometers 942 can be located on the same layer as one or more of electrodes 932, piezoelectric sensors 934, and plurality of temperature sensors 938. In some examples, the monitoring system can include one or more accelerometers that can be located in areas (e.g., structure of bed 110 illustrated in FIG. 1) of the monitoring system different from the sub-mats. By including one or more separate accelerometers in a location different from the sub-mats, the controller can be capable of including or utilizing the measurement from the one or more separate accelerometers to differentiate the acceleration measurements from the other measurements (e.g., capacitive, electrical, and piezoelectric).

In one or more of the exemplary monitoring systems described above, the monitoring system can be configured to measure impedance cardiography (ICG). The ICG measurement can be used to measure the impedance and the total electrical conductivity of the user's body. The ICG measurement can be used at least partially to measure the heart rate, heart rate variability, respiratory rate, and/or respiratory rate variability. In some examples, one or more electrodes can be configured for an ICG measurement by measuring the change in impedance due to the user's electrical conductivity.

Figure 10A:
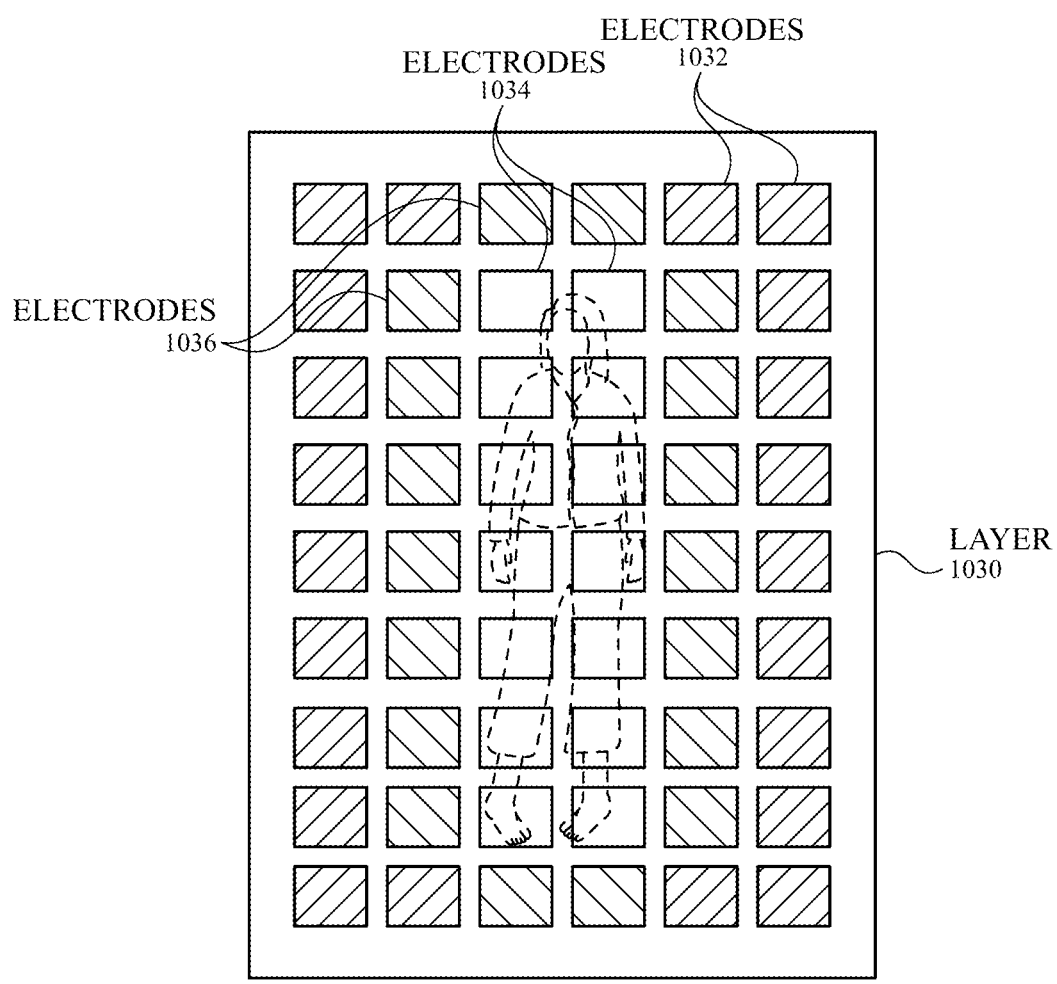
FIG. 10A illustrates a top view of an exemplary layer included in a mat configured for ICG measurements according to examples of the disclosure.
Figure 10B:
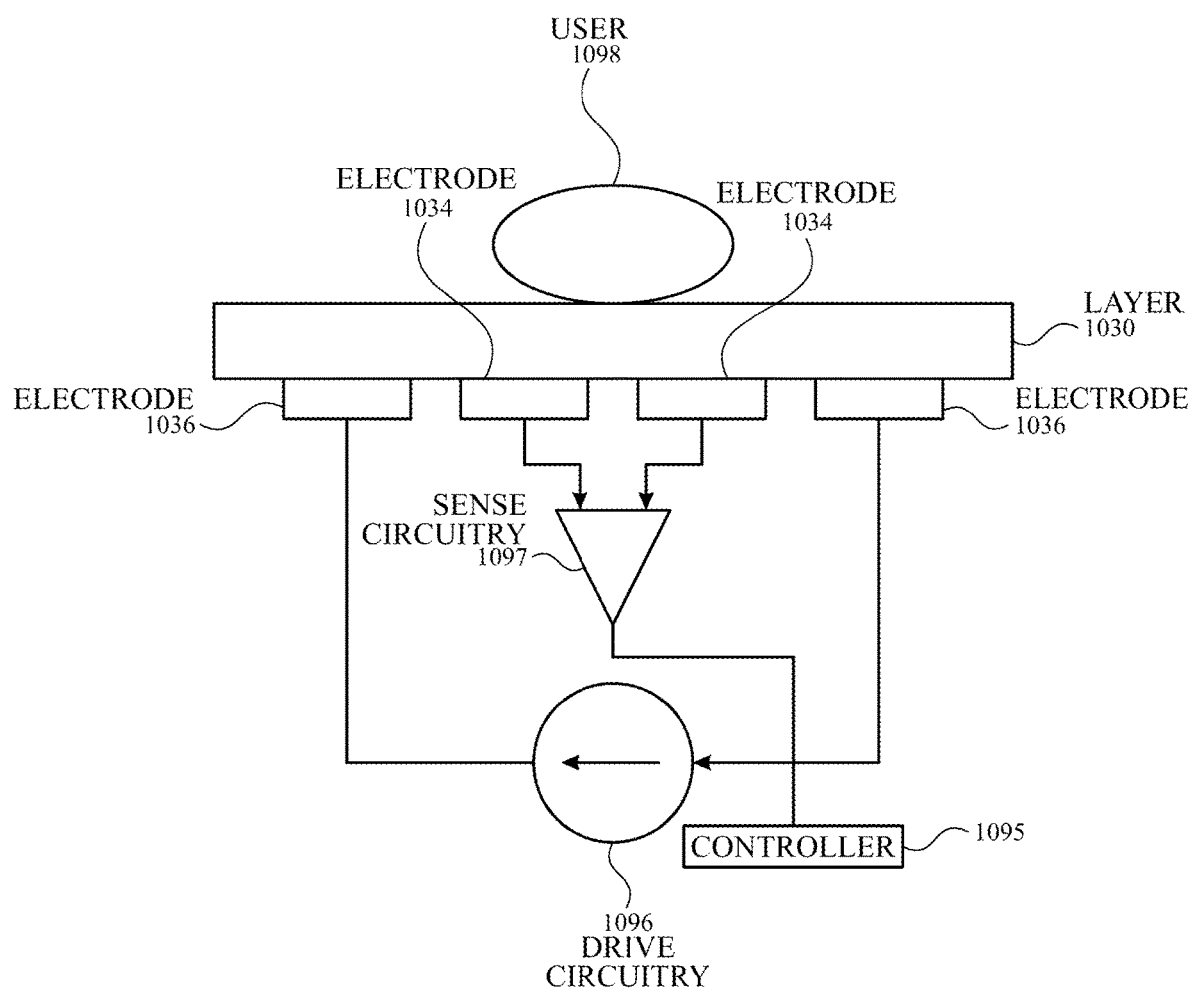
FIG. 10B illustrates a corresponding circuit diagram according to examples of the disclosure.

FIG. 10A illustrates a top view of an exemplary layer included in a mat configured for ICG measurements, and FIG. 10B illustrates a corresponding circuit diagram according to examples of the disclosure. System 1099 can include layer 1030 and a plurality of electrodes, such as plurality of electrodes 1032, plurality of electrodes 1034, and plurality of electrodes 1036. Plurality of electrodes 1034 can be located directly under the body of user 1098. Plurality of electrodes 1036 can be located in the immediate periphery (i.e., adjacent to the electrodes located directly under the body of the user) of the user's body. Plurality of electrodes 1032 can be located in the periphery of the mat. In some examples, one or more electrodes can be located in both the immediate periphery of the user's body and the periphery of the mat. Plurality of electrodes 1032, plurality of electrodes 1036, or both can be coupled to drive circuitry 1096. Drive circuitry 1096 can be configured to drive current through the electrodes coupled to it. Plurality of electrodes 1034 can be coupled to sense circuitry 1097. Sense circuitry 1097 can be configured to measure changes in impedances and transmit the measured impedance values to controller 1095.

In some examples, one or more of plurality of electrodes 1032, plurality of electrodes 1034, and plurality of electrodes 1036 can be configured for capacitive, electrical, or impedance measurement during one operation mode and can be configured for another (e.g., capacitive, electrical, or impedance) measurement during another operation mode. In some examples, drive circuitry for capacitive measurements can be the same as drive circuitry for impedance measurements. In some examples, drive circuitry for capacitive measurements can be different from drive circuitry for impedance measurements. In some examples, the frequency for stimulating the electrodes for impedance measurements can be included in a narrow band. In some examples, the frequency for stimulating the electrodes for impedance measurements can include 50 Hz.

Figure 10C:
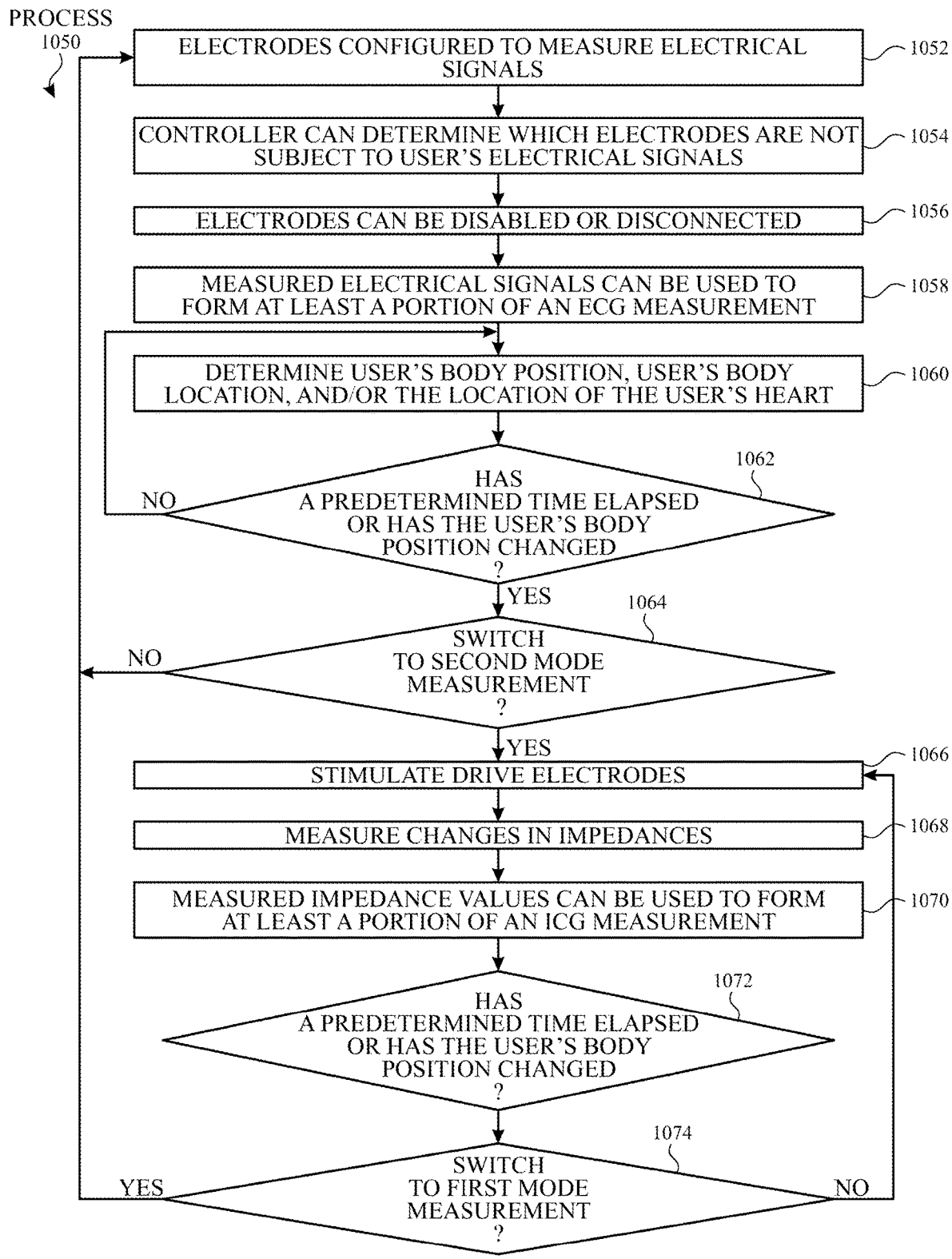
FIG. 10C illustrates an exemplary process flow configured for impedance measurement according to examples of the disclosure.

FIG. 10C illustrates an exemplary process flow configured for impedance measurement according to examples of the disclosure. In some examples, the monitoring system can operate in multiple modes: one mode (i.e., first mode) for measuring electrical signals and another mode (i.e., second mode) for measuring changes in impedances. During the first mode, one or more electrodes can be configured to measure the user's electrical signals (step 1052 of process 1050). In some examples, the difference in electrical potential between multiple electrodes can be measured. The controller or processor can determine which electrodes are not affected by the user's electrical signals (step 1054 of process 1050) and can disable or disconnect the electrodes to conserve power, for example (step 1056 of process 1050). In some examples, the controller can select the electrodes located underneath the user's body for electrical measurements. The measured electrical signals can be used to form at least a portion of an ECG measurement (step 1058 of process 1050). In some examples, the electrical signals can be used to determine the user's body position, user's body location and/or location of the user's heart (step 1060 of process 1050). In some examples, step 1052 can be used to form a rough estimate or coarse image of the user's body position and/or location, and step 1060 can be used to form a more detailed or finer imager of the user's body position and/or location. The second mode can be repeated after a predetermined time interval and/or when the user's body position and/or location change (step 1062 of process 1050).

In some examples, the second mode can be repeated after the first mode has been completed (step 1064 of process 1050).

During the second mode, one or more electrodes can be coupled to drive circuitry. The drive electrodes can be stimulated with a stimulation frequency (step 1066 of process 1050). In some examples, the difference in impedance between multiple electrodes can be measured. In some examples, the controller can select the electrodes (e.g., electrodes 1036 illustrated in FIG. 10A) located in the immediate periphery of the user's body as the drive electrodes. In some examples, the controller can select the electrodes (e.g., electrodes 1032 illustrated in FIG. 10A) located in the periphery of the mat as the drive electrodes. One or more sense electrodes can be coupled to sense circuitry (e.g., sense circuitry 1097 illustrated in FIG. 10B). Sense circuitry can measure the changes in impedances (step 1068 of process 1050). The measured impedance values can be used to form at a least a portion of an ICG measurement (step 1070 of process 1050). The second mode can be repeated after a predetermined time interval and/or when the user's body position and/or location change (step 1072 of process 1050). In some examples, the second mode can be repeated after the first mode has been completed (step 1074 of process 1050).

Figure 11A:
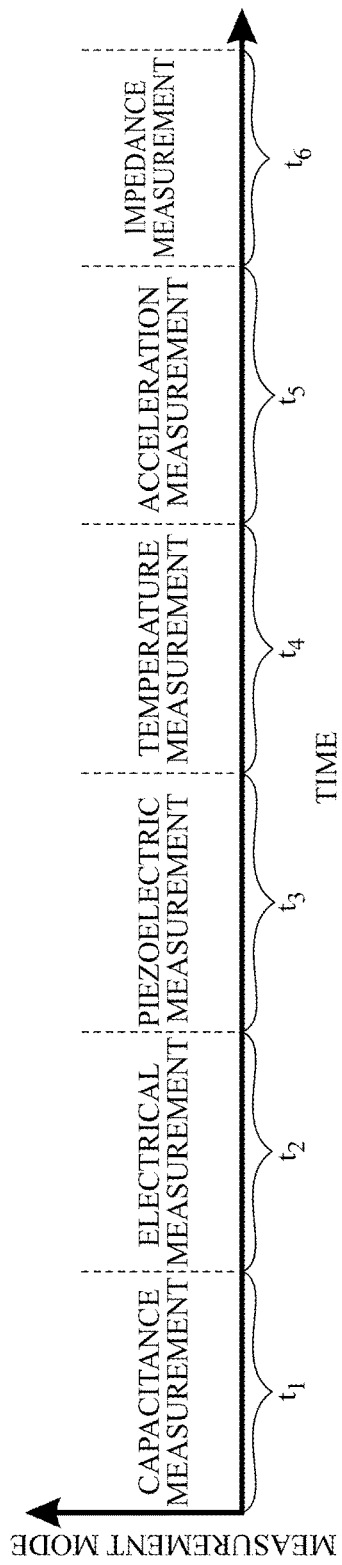
FIGS. 11A-11C illustrate measurement modes over time for a monitoring system according to examples of the disclosure.
Figure 11B:
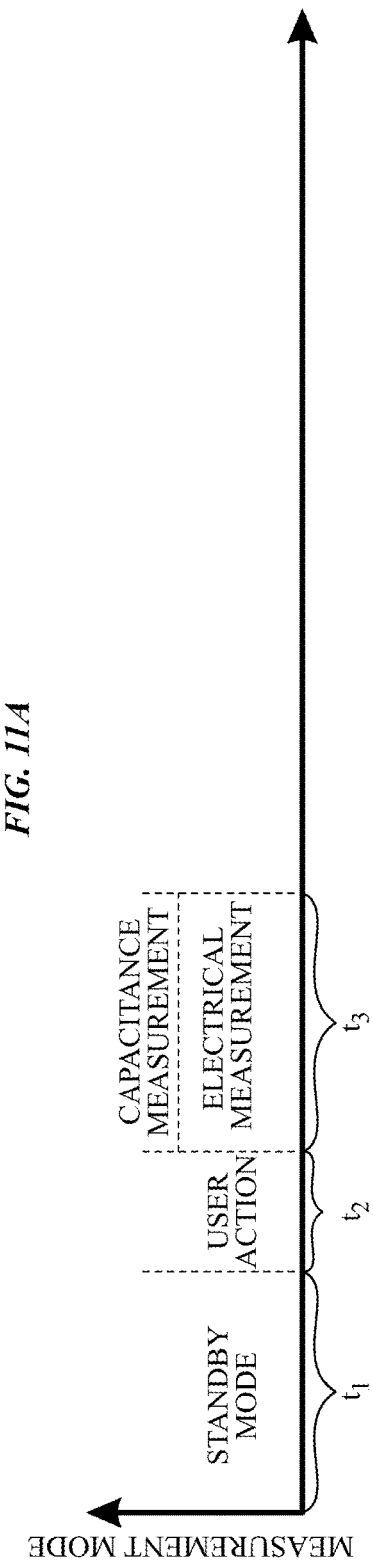
Figure 11C:
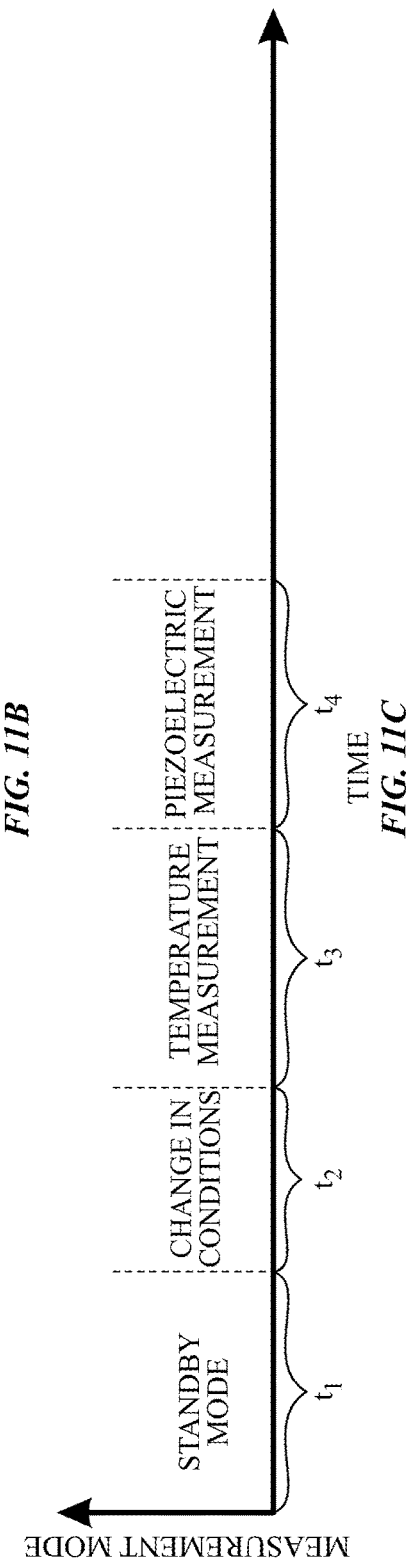

The monitoring system can be configured in one or more measurement modes at a given time. For example, as illustrated in FIG. 11A, the monitoring system can be configured to time multiplex and cycle between the different measurement modes (e.g., capacitance measurement in t1, electrical measurement in t2, piezoelectric measurement in t3, temperature measurement in t4, acceleration measurement in t5, and impedance measurement in t6). In some examples, as illustrated in FIG. 11B, the monitoring system can be configured for one or more measurements responsive to the user's action. For example, the system can be in a standby mode during t1. The user's body position can move (i.e., user action during time t2), and the monitoring system can be configured for capacitive and electrical measurements, in response to the user action, during time t3. In some examples, as illustrated in FIG. 11C, the monitoring system can be configured for one or more first measurements responsive to one or more changes in conditions. For example, the monitoring system can be configured for periodically measuring the temperature of the room using a control panel (e.g., control panel 140 illustrated in FIG. 1) during standby mode in time t1. The monitoring system can determine that the temperature of the room increased above a predetermined threshold during time t2 (i.e., change in conditions). In response to the change in temperature, the monitoring system can measure the temperature of the local ambient and the user's body temperature during time t3. In some examples, one or more second measurements can be performed conditioned upon the one or more first measurements. If the temperature of the local ambient and/or the user's body temperature increased to greater than another predetermined threshold, then the user may have transitioned to a different sleep state, which may have affected the user's respiratory rate and respiratory rate variability. The monitoring system can be configured for piezoelectric measurements during time t4 to measure the user's respiratory rate and respiratory rate variability.

The monitoring system can be further configured to provide analysis to the user by giving the user feedback regarding the consistency, quality, and duration of the user's sleep. For example, the system can correlate disruption of one user's sleep with movement and/or position of another user in the bed. The monitoring system can provide feedback based on the movement and/or position of other users in the bed and can help the users analyze and troubleshoot their sleep.

In some examples, the system can correlate disruption of a user's sleep to one or more room conditions (e.g., room temperature, ambient lights, and environmental sounds). In some examples, the correlation can be used to adjust the temperature of the room through the control system and/or adjust the temperature of the local ambient through active heating or cooling of the mat. In some examples, the monitoring system can determine that the thermal comfort of multiple users can be different, and active heating and/or cooling can be used to accommodate the differences in thermal comfort. In some examples, the monitoring system can communicate one or more non-system components (e.g., window blinds) to enhance the ambient conditions. In some examples, the monitoring system can include one or more actuators in the mat or in communication with the mat. The one or more actuators can be configured to, for example, wake up one or more users based on the user's sleep state, duration of sleep, and/or time of day.

In some examples, the monitoring system can compare present sleep analysis and measurements with historical sleep analysis and measurements. The monitoring system can notice a change in sleep patterns over the course of time and can alert the user or provide feedback.

As discussed above, examples of the disclosure can include measuring a plurality of vital signs for one or more users. Additional information can be used to improve the delivery of measured information, analysis, or any other content that may be of interest to the users. In some examples, the measured information, analysis, or other content may include personal information that may uniquely identify the user or may be used to contact or locate the user. Such personal information can include geographic information, demographic information, telephone numbers, email addresses, mailing addresses, home addresses, or other identifying information. In some examples, the use of such personal information can be used to the benefit of the user. For example, the personal information can be used to deliver to the user the measured information, analysis, or other content. Use of personal information can include, but is not limited to, enabling timely and controlled delivery of the content.

The disclosure also contemplates that an entity that may be using (e.g., measuring, collecting, analyzing, disclosing, transferring, and/or storing) the personal information will comply with well-established privacy policies and/or privacy practices. These privacy policies and/or privacy practices can be generally recognized as meeting (or exceeding) industry or governmental requirements for private and secure personal information and should be implemented and consistently used. For example, personal information should be collected for legitimate and reasonable purposes and should not be shared (e.g., sold) outside of those purposes. Furthermore, collected personal information should occur only after receiving the informed consent of the user(s). To adhere to privacy policies and/or privacy practices, entities would take any steps necessary for safeguarding and securing outside access to the personal information. In some examples, entities can subject themselves to third party evaluation(s) to certify that the entities are adhering to the well-established, generally recognized privacy policies and/or privacy practices.

In some examples, the user(s) can selectively block or restrict access to and/or use of the personal information. The monitoring system can include one or more hardware components and/or one or more software applications to allow the user(s) to selective block or restrict access to and/or use of the personal information. For example, the monitoring system can be configured to allow users to "opt in" or "opt out" of advertisement delivery services when collecting personal information during registration. In some examples, a user can select which information (e.g., home address) to withhold from the advertisement delivery services.

Although examples of the disclosure can include monitoring systems and method for measuring vital signs with the use of the user's personal information, examples of the disclosure can also be capable of one or more functionalities and operation without the user's personal information. Lack of all or a portion of the personal information may not render the monitor systems and methods inoperable. In some examples, content can be selected and/or delivered to the user based on non-user specific personal (e.g., publicly available) information.

A system for determining one or more physiological signals of a user is disclosed. The system can comprise: a first one or more electrodes configured to measure one or more electrical signals; a second one or more electrodes configured to capacitively couple to the first one or more electrodes; and logic configured to: detect a plurality of changes in capacitive coupling between the first one or more electrodes and the second one or more electrodes; determine at least one or more of one or more positions, one or more body motions, and one or more locations of the user based on the plurality of changes in capacitive coupling; detect the one or more electric signals; and determine one or more physiological signals based at least in part on the plurality of changes in capacitive coupling and the one or more electrical signals. Additionally or alternatively, in some examples, the first one or more electrodes are located within a first portion of the system, and the second one or more electrodes are located within a second portion of the system, the second portion is at least partially physically separated from the first portion. Additionally or alternatively, in some examples, the first portion is included in a sheet, and the second portion is included in a blanket. Additionally or alternatively, in some examples, the system further comprises: one or more switches configured to electrically couple at least two of the first one or more electrodes together or at least two of the second one or more together, wherein the logic is further configured to associate a decrease in each of the plurality of changes in capacitive coupling to an increase in gap due to a body of the user physically separating the first one or more first electrodes from the second one or more electrodes. Additionally or alternatively, in some examples, the system further comprises: a first section with a first granularity; a second section with a second granularity capable of being different from the first granularity; and one or more switches configured to couple or decouple the first one or more electrodes together, the second one or more electrodes together, or both to dynamically change one or more of the first and second granularities.

A method for determining one or more physiological signals of a user is disclosed. The method can comprise: stimulating a first one or more electrodes; coupling a second one or more electrodes to sense circuitry, the second one or more electrodes configured to capacitively coupling to the first one or more electrodes; detecting a plurality of changes in capacitive coupling at the second one or more electrodes; determining at least one of more of one or more positions, one or more body motions, and one or more locations of the user based on the plurality of changes in capacitive coupling; detecting one or more electrical signals using the second one or more electrodes; and determining one or more physiological signals based on at least in part to the plurality of changes in capacitive coupling and the one or more electrical signals. Additionally or alternatively, in some examples, the method further comprises: forming electrocardiography information from at least the one or more electrical signals, wherein the one or more physiological signals include one or more of a heart rate, heart rate variability, a respiratory rate, and respiratory rate variability. Additionally or alternatively, in some examples, the method further comprises: forming ballistocardiography information from at least the plurality of changes in capacitive coupling, wherein the one or more physiological signals include one or more of a heart rate, heart rate variability, a respiratory rate, and respiratory rate variability. Additionally or alternatively, in some examples, the method further comprises: determining gross motion based on the plurality of changes in capacitive coupling; and determining fine body movements based on the one or more electrical signals. Additionally or alternatively, in some examples, the method further comprises: determining that a change in capacitive coupling between at least one of the first one or more electrodes and at least one of the second one or more electrodes is less than a predetermined threshold; electrically coupling the first one or more electrodes together; stimulating a third one or more electrodes, the third one or more electrodes configured to capacitively couple to the first one or more electrodes; coupling the first one or more electrodes to sense circuitry; and detecting a second plurality of changes in capacitive coupling at the first one or more electrodes. Additionally or alternatively, in some examples, the method further comprises: dynamically changing a granularity of at least a section of the system by electrically coupling or decoupling at least two of the first one or more electrodes, at least two of the second one or more electrodes, or both. Additionally or alternatively, in some examples, the method further comprises: associating a first of the plurality of changes in capacitive coupling, a first of the one or more electrical signals, or both to a first user; and associating a second of the plurality of changes in capacitive coupling, a second of the one or more electrical signals, or both to a second user. Additionally or alternatively, in some examples, the method further comprises: determining one or more temperature values with a plurality of temperature sensors; and refining the determination of the at least one of the one or more positions, one or more body motions, one or more locations, or both of the user based on the one or more temperature values. Additionally or alternatively, in some examples, the method further comprises: determining one or more temperature values with a plurality of temperature sensors; associating a first set of the one or more temperature values to a local ambient; and associating a second set of the one or more temperature values to a temperature of the user.

A system for determining one or more physiological signals of a user is disclosed. The system comprises: a plurality of electrodes configured to operate in at least one operation mode, wherein the operation modes comprise: capacitance measurement mode, electrical measurement mode, and impedance measurement; one or more piezoelectric sensors configured to measure one or more mechanical impulses; and logic further configured to: determine one or more values, the one or more values being one or more of changes in capacitive coupling, electrical signals, and impedance using the plurality of electrodes, determine at least one or more of the one or more positions, one or more body motions, and one or more locations of the user based on the one or more values; determine one or more mechanical impulses using the one or more piezoelectric sensors; and determine the one or more physiological signals based at least in part on the one or more values and the one or more mechanical impulses. Additionally or alternatively, in some examples, the one or more piezoelectric sensors include one or more sections of rigid material physically connected with flexible material. Additionally or alternatively, in some examples, the one or more piezoelectric sensors are arranged in one or more rows, one or more columns, or both of piezoelectric sensors, each piezoelectric sensor capable of being independently controlled. Additionally or alternatively, in some examples, the one or more piezoelectric sensors are interleaved with the plurality of electrodes. Additionally or alternatively, in some examples, at least some of the plurality of electrodes are disposed on the one or more piezoelectric sensors. Additionally or alternatively, in some examples, the system further comprises: a plurality of temperature sensors configured to measure one or more temperatures. wherein the plurality of temperature sensors are arranged in one or more rows, one or more columns, or both of temperature sensors, and further wherein the plurality of temperature sensors are interleaved with at least one of the plurality of electrodes and the one or more piezoelectric sensors. Additionally or alternatively, in some examples, the system further comprises: one or more accelerometers configured to measure one or more acceleration values, wherein the one or more accelerometers are arranged in one or more rows, one or more columns, or both of accelerometers, and wherein the one or more accelerometers are interleaved with at least one of the plurality of electrodes, the one or more piezoelectric sensors, and the one or more temperature sensors. Additionally or alternatively, in some examples, the system further comprises: one or more accelerometers configured to measure one or more acceleration values, wherein at least one of the one or more accelerometers is located on a frame of a bed. Additionally or alternatively, in some examples, the system further comprises: one or more actuators configured to provide motion or vibration to the system. Additionally or alternatively, in some examples, the system further comprises: a transceiver configured for communicating with one or more components separate and distinct from the system. Additionally or alternatively, in some examples, the system includes one or more of a sheet, blanket, and pillow.

A method for determining one or more physiological signals of a user is disclosed. The method can comprise: stimulating a first one or more electrodes; coupling a second one or more electrodes to sense circuitry, the second one or more electrodes configured to capacitively couple to the first one or more electrodes; detecting a plurality of changes in capacitive coupling at the second one or more electrodes; determining movement information of the user based on the plurality of changes in capacitive coupling, the determination having a first granularity; detecting one or more mechanical impulses with one or more piezoelectric sensors; and determining movement information of the user based on the one or more mechanical impulses, the determination having a second granularity greater than the first granularity.

A method of analyzing a sleep of a user is disclosed. The method can comprise: operating a monitoring system in at least two operation modes, the operation modes comprising: capacitance measurement mode, electrical measurement mode, piezoelectric measurement mode, temperature measurement mode, acceleration measurement mode, impedance measurement mode, and standby mode. Additionally or alternatively, in some examples, at least two operation modes are operated concurrently. Additionally or alternatively, in some examples, the operation modes alternate. Additionally or alternatively, in some examples, the method further comprises: detecting one or more changes in conditions associated with the system; and dynamically switching to one or more operating modes based on the one or more changes in conditions.

While various examples have been described above, it should be understood that they have been presented by way of example only, and not by way of limitation. Although examples have been fully described with reference to the accompanying drawings, the various diagrams can depict an exemplary architecture or other configuration for this disclosure, which is done to aid in the understanding of the features and functionality that can be included in the disclosure. The disclosure is not restricted to the illustrated exemplary architectures or configurations, but can be implemented using a variety of alternative architectures and configurations. Additionally, although the disclosure is described above in terms of various examples and implementations, it should be understood that the various features and functionality described in one or more of the examples are not limited in their applicability to the particular example with which they are described. They instead can be applied alone or in some combination, to one or more of the other examples of the disclosure, whether or not such examples are described, whether or not such features are presented as being part of a described example. Thus, the breadth and scope of the present disclosure should not be limited by any of the above-described examples.

What is claimed is:

1. A bed sensing system for monitoring physiological parameters of a user, the bed sensing system comprising:
   a flexible sensing structure configured for placement across a bed and comprising:
   an array of capacitive sensors;
   an array of temperature sensors; and
   a processor configured to:
      determine a location of the user using the array of capacitive sensors;
      select a subset of the array of temperature sensors based on the determined location of the user;
      receive one or more signals from the subset of the array of temperature sensors, the one or more signals indicating temperatures across a portion of the flexible sensing structure corresponding to the subset of the array of temperature sensors; and
      determine one or more temperature based physiological parameters of the user using the one or more signals.

2. The bed sensing system of claim 1, wherein the processor is configured to:
   receive temperature measurements from one or more temperature sensors that are not in the subset of the array of temperature sensors; and
   determine a temperature of an ambient environment using the one or more temperature sensors.

3. The bed sensing system of claim 1, wherein the processor is configured to:
   determine that the user changed position;
   determine an updated position of the user using the array of capacitive sensors;
   select a second subset of the array of temperature sensors based on the updated position of the user; and
   determine one or more temperature based physiological parameters of the user using the second subset of the array of temperature sensors.

4. The bed sensing system of claim 1, wherein determining the one or more temperature based physiological parameters comprises determining a temperature image of the user using the subset of the array of temperature sensors.

5. The bed sensing system of claim 1, wherein:
the flexible sensing structure further comprises piezoelectric sensors; and
the processor is configured to determine the one or more physiological parameters of the user using the piezoelectric sensors.

6. The bed sensing system of claim 1, wherein:
the flexible sensing structure further comprises accelerometers; and
the processor is configured to determine the location of the user, one or more physiological parameters of the user, or both using the accelerometers.

7. The bed sensing system of claim 1, wherein:
the array of capacitive sensors comprises a first set of electrodes positioned along a first layer of the flexible sensing structure and a second set of electrodes positioned along a second layer of the flexible sensing structure; and
electrodes in the first set of electrodes are configured to capacitively couple with electrodes in the second set of electrodes.

8. The bed sensing system of claim 7, wherein the processor is configured to determine the one or more physiological parameters of the user using the array of capacitive sensors.

9. The bed sensing system of claim 8, wherein the one or more physiological parameters comprise a electrocardiogram (ECG) measurement.

10. A system for monitoring a user located in a bed, the system comprising:
a flexible sensing structure configured for placement across the bed and comprising:
an array of capacitive sensors;
an array of temperature sensors; and
a processor configured to:
determine a location of the user with respect to the flexible sensing structure using the array of capacitive sensors;
in a first mode of operation:
select a subset of the array of temperature sensors corresponding to the determined location of the user with respect to the flexible sensing structure; and
determine a temperature of the user using the subset of the array of temperature sensors; and
in a second mode of operation:
select a subset of the array of capacitive sensors based on the determined location of the user; and
determine a physiological parameter of the user using the subset of the array of capacitive sensors.

11. The system of claim 10, wherein the array of capacitive sensors and the array of temperature sensors are positioned on a same layer of the flexible sensing structure.

12. The system of claim 10, wherein:
in the first mode of operation the processor is configured to generate a temperature image of the user; and
in the second mode of operation the processor is configured to determine one or more cardiac parameters of the user.

13. The system of claim 12, wherein the one or more cardiac parameters comprise at least one of a ballistocardiograph (BCG) measurement, a electrocardiogram (ECG) measurement or both.

14. A system for monitoring physiological parameters of a user, the system comprising:
a flexible sensing structure configured for placement across a bed and comprising:
an array of electromechanical sensors; and
an array of temperature sensors; and
a processor configured to:
determine a location of the user using the array of electromechanical sensors;
select a subset of the array of temperature sensors based on the determined location of the user;
receive one or more signals from the subset of the array of temperature sensors, the one or more signals indicating temperatures across a portion of the flexible sensing structure corresponding to the subset of the array of temperature sensors; and
determine one or more temperature based physiological parameters of the user using the one or more signals.

15. The system of claim 14, wherein the processor is further configured to generate a temperature image from one or more first signals using the array of temperature sensors.

16. The system of claim 15, wherein the processor is further configured to update the determined location of the user based on the temperature image.

17. The system of claim 14, wherein the array of electromechanical sensors comprises a set of electrodes configured to measure one or more electrical parameters of the user.

18. The system of claim 17, wherein:
the set of electrodes comprises one or more first electrodes and one or more second electrodes;
the one or more first electrodes are located on a first layer of the flexible sensing structure; and
the one or more second electrodes are located on a second layer of the flexible sensing structure.

19. The system of claim 14, wherein:
the array of electromechanical sensors comprises one or more piezoelectric sensors; and
the processor is configured to determine the one or more physiological parameters using the one or more piezoelectric sensors.

20. The system of claim 14, wherein the array of electromechanical sensors comprises one or more accelerometers configured to measure acceleration, vibrations, or both.

21. The system of claim 20, wherein the one or more accelerometers are located on a same layer of the flexible sensing structure as the array of temperature sensors.

* * * * *